US008323884B2

(12) United States Patent
Ryan

(10) Patent No.: US 8,323,884 B2
(45) Date of Patent: Dec. 4, 2012

(54) ISOLATED SNARE YKT6 GENOMIC POLYNUCLEOTIDE FRAGMENTS FROM CHROMOSOME 7 AND THEIR USES

(75) Inventor: James Ryan, Augusta, GA (US)

(73) Assignee: Ryogen LLC, Suffern, NY (US)

( * ) Notice: Subject to any disclaimer, the term of this patent is extended or adjusted under 35 U.S.C. 154(b) by 244 days.

(21) Appl. No.: 12/533,130

(22) Filed: Jul. 31, 2009

(65) Prior Publication Data

US 2009/0324626 A1 Dec. 31, 2009

Related U.S. Application Data

(60) Division of application No. 10/642,946, filed on Aug. 18, 2003, now Pat. No. 7,588,915, which is a continuation of application No. 09/957,956, filed on Sep. 21, 2001, now abandoned.

(60) Provisional application No. 60/234,422, filed on Sep. 21, 2000.

(51) Int. Cl.
*C12Q 1/68* (2006.01)
*C12P 21/06* (2006.01)
*C07H 21/00* (2006.01)
*C07H 21/02* (2006.01)
*C07H 21/04* (2006.01)

(52) U.S. Cl. .......... 435/6; 435/69.1; 435/91.1; 435/455; 536/23.1; 536/23.2; 536/23.5; 536/24.31

(58) Field of Classification Search ............ 435/6, 91.1, 435/91.4, 455, 19.1; 536/23.1, 23.5, 24.1, 536/24.31, 23.2
See application file for complete search history.

(56) References Cited

U.S. PATENT DOCUMENTS

| | | | |
|---|---|---|---|
| 5,541,060 A | 7/1996 | Bell | |
| 5,624,803 A | 4/1997 | Noonberg | |
| 5,972,334 A | 10/1999 | Denney | |
| 6,783,961 B1 * | 8/2004 | Edwards et al. | 435/91.1 |
| 6,812,339 B1 | 11/2004 | Venter | |
| 2002/0048763 A1 | 4/2002 | Penn | |
| 2003/0077808 A1 | 4/2003 | Rosen | |
| 2003/0204075 A9 * | 10/2003 | Wang | 536/24.3 |
| 2007/0015162 A1 | 1/2007 | Rosen | |
| 2007/0031842 A1 | 2/2007 | Rosen | |
| 2007/0048818 A1 * | 3/2007 | Rosen et al. | 435/69.1 |

FOREIGN PATENT DOCUMENTS

| | | |
|---|---|---|
| WO | WO9520678 | 8/1995 |
| WO | WO0058467 | 10/2000 |

OTHER PUBLICATIONS

Sulston et al, Genome Res., vol. 8, No. 11, pp. 1097-1108 (1998).*
Tanizawa et al., Mol. Endocrinol., vol. 6, No. 7, pp. 1070-1081 (1992).*
The Sangre Centre et al., Genome Res., vol. 8, No. 11, pp. 1097-1108 (1998).*
U.S. Appl. No. 09/957,956 Non-Final Office Action Dec. 4, 2002.
U.S. Appl. No. 09/957,956 09/957,956 Non-Final Office Action May 21, 2003.
U.S. Appl. No. 10/642,946 Non-Final Office Action Oct. 17, 2006.
U.S. Appl. No. 10/642,946 Non-Final Office Action Oct. 26, 2007.
U.S. Appl. No. 10/642,946 Non-Final Office Action Mar. 25, 2008.
U.S. Appl. No. 10/642,946 Non-Final Office Action Oct. 16, 2008.
U.S. Appl. No. 10/642,946 Notice of Allowance Apr. 28, 2009.
U.S. Appl. No. 60/231,498, filed Sep. 8, 2000 Venter (priority for US Patent 6,812,339).
Table 1 of U.S. Appl. No. 60/231,498.
Table 2 of U.S. Appl. No. 60/231,498.
Table 3 of U.S. Appl. No. 60/231,498.
Table 4 of U.S. Appl. No. 60/231,498.
Table 5 of U.S. Appl. No. 60/231,498.
Table 6 of U.S. Appl. No. 60/231,498.
Table 7 of U.S. Appl. No. 60/231,498.
Table 8 of U.S. Appl. No. 60/231,498.
Table 9 of U.S. Appl. No. 60/231,498.
Table 10 of U.S. Appl. No. 60/231,498.
Table 11 of U.S. Appl. No. 60/231,498.
Table 12 of U.S. Appl. No. 60/231,498.
Table 13 of U.S. Appl. No. 60/231,498.
Table 14 of U.S. Appl. No. 60/231,498.
Table 15 of U.S. Appl. No. 60/231,498.
Table 16 of U.S. Appl. No. 60/231,498.
Table 17 of U.S. Appl. No. 60/231,498.
Table 18 of U.S. Appl. No. 60/231,498.
Table 19 of U.S. Appl. No. 60/231,498.
Table 20 of U.S. Appl. No. 60/231,498.
Table 21 of U.S. Appl. No. 60/231,498.
Table 22 of U.S. Appl. No. 60/231,498.
Table 23 of U.S. Appl. No. 60/231,498.
Table 24 of U.S. Appl. No. 60/231,498.
Table 25 of U.S. Appl. No. 60/231,498.
Ahmed, PNAS 96: 14795-14800. 1999.
Altschul, Nucleic Acids Res. 25: 3389-3402. 1997.
Burge, J. Mol. Biol. 268: 78-94. 1997.
EMBL database Accession No. Q9UES0 May 1, 2000 SNARE protein Ykt6 (Fragment) *Homo sapiens*.
Layne, J. Biol. Chem. 273:15654-15660. 1998.
Maestrini, Hum. Mol. Gen. 2: 761-766. 1993.
McNew, J. Biol. Chem. 272: 17776-17783. 1997.
Muise, Biochem J. 343: 341-345. 1999.
Nuttal, Bone 27: 177-184. 2000.
Ohno, Biochem Biophys Res Comm 228: 411-414. 1996.
Skidgel, TIPS 9: 299-304. 1988.

(Continued)

*Primary Examiner* — Jane Zara
(74) *Attorney, Agent, or Firm* — Cheryl H. Agris

(57) ABSTRACT

The invention is directed to isolated genomic polynucleotide fragments that encode human SNARE YKT6, human glucokinase, human adipocyte enhancer binding protein (AEBP1) and DNA directed 50 kD regulatory subunit (POLD2), vectors and hosts containing these fragments and fragments hybridizing to noncoding regions as well as antisense oligonucleotides to these fragments. The invention is further directed to methods of using these fragments to obtain SNARE YKT6, human glucokinase, AEBP1 protein and POLD2 and to diagnose, treat, prevent and/or ameliorate a pathological disorder.

16 Claims, No Drawings

OTHER PUBLICATIONS

Waterston, R.H. GenBank Accession No. AC006456.3 (gi: 21322189) Submitted Jan. 28, 1999, bases 1-75609.
Waterston, R.H. GenBank Accession No. AC006454.2 (gi:4337283) Submitted Jan. 28, 1999, bases 1-151965.
Zhang, Genomics 29: 179-186.1995.
Non-Final Office Action MAy 21, 2010 U.S. Appl. No. 12/533,105.
Non-Final Office Action Jun. 15, 2010 U.S. Appl. No. 12/533,164.
Sequence Alignment Non-final Office Action May 21, 2010 U.S. Appl. No. 12/533,105.
Sequence Alignment Non-final Office Action Jun. 15, 2010 U.S. Appl. No. 12/533,164.
Perez "Characterization of the 5'-flanking region of the gene encoding the 50 kDa subunit of human DNA polymerase δ" Biochem Biophys Acta 1493: 231-236. 2000.
Waterston 1999 GenBank AccNo. AC0006456.2 gi:4337283 submitted Mar. 5 1999 bases 1-151965.
Final Office Action Nov. 29, 2010 U.S. Appl. No. 12/533,105.
Final Office Action Dec. 29, 2010 U.S. Appl. No. 12/533,164.
Stoffel et al. "Human glucokinase gene: Isolation, characterization, and identification of two missense mutations linked to early-onset non-insulin-dependent (type 2) diabetes mellitus." Proc. Natl. Acad. Sci. USA 89: 7698-7702. 1992.
U.S. Appl. No. 12/533,087 Non-final Office Action Apr. 6, 2011.
U.S. Appl. No. 12/533,087 Final Office Action Oct. 4, 2011.
U.S. Appl. No. 12/533,087 Notice of Allowance/Allowability Jan. 12, 2012.
U.S. Appl. No. 12/533,105 Non-final Office Action Mar. 5, 2012.
U.S. Appl. No. 12/533,164 Non-final Office Action Mar. 2, 2012.

* cited by examiner

SEQUENCE LISTING

```
<160> NUMBER OF SEQ ID NOS: 8

<210> SEQ ID NO 1
<211> LENGTH: 198
<212> TYPE: PRT
<213> ORGANISM: Homo sapiens

<400> SEQUENCE: 1

Met Lys Leu Tyr Ser Leu Ser Val Leu Tyr Lys Gly Glu Ala Lys Val
1               5                   10                  15

Val Leu Leu Lys Ala Ala Tyr Asp Val Ser Ser Phe Ser Phe Phe Gln
            20                  25                  30

Arg Ser Ser Val Gln Glu Phe Met Thr Phe Thr Ser Gln Leu Ile Val
        35                  40                  45

Glu Arg Ser Ser Lys Gly Thr Arg Ala Ser Val Lys Glu Gln Asp Tyr
    50                  55                  60

Leu Cys His Val Tyr Val Arg Asn Asp Ser Leu Ala Gly Val Val Ile
65                  70                  75                  80

Ala Asp Asn Glu Tyr Pro Ser Arg Val Ala Phe Thr Leu Leu Glu Lys
                85                  90                  95

Val Leu Asp Glu Phe Ser Lys Gln Val Asp Arg Ile Asp Trp Pro Val
            100                 105                 110

Gly Ser Pro Ala Thr Ile His Tyr Pro Ala Leu Asp Gly His Leu Ser
        115                 120                 125

Arg Tyr Gln Asn Pro Arg Glu Ala Asp Pro Met Thr Lys Val Gln Ala
    130                 135                 140

Glu Leu Asp Glu Thr Lys Ile Ile Leu His Asn Thr Met Glu Ser Leu
145                 150                 155                 160

Leu Glu Arg Gly Glu Lys Leu Asp Asp Leu Val Ser Lys Ser Glu Val
```

165                 170                 175
Leu Gly Thr Gln Ser Lys Ala Phe Tyr Lys Thr Ala Arg Lys Gln Asn
            180                 185                 190

Ser Cys Cys Ala Ile Met
        195

<210> SEQ ID NO 2
<211> LENGTH: 464
<212> TYPE: PRT
<213> ORGANISM: Homo sapiens

<400> SEQUENCE: 2

Met Pro Arg Pro Arg Ser Gln Leu Pro Gln Pro Asn Ser Gln Val Glu
1               5                   10                  15

Gln Ile Leu Ala Glu Phe Gln Leu Gln Glu Glu Asp Leu Lys Lys Val
            20                  25                  30

Met Arg Arg Met Gln Lys Glu Met Asp Arg Gly Leu Arg Leu Glu Thr
        35                  40                  45

His Glu Glu Ala Ser Val Lys Met Leu Pro Thr Tyr Val Arg Ser Thr
    50                  55                  60

Pro Glu Gly Ser Glu Val Gly Asp Phe Leu Ser Leu Asp Leu Gly Gly
65                  70                  75                  80

Thr Asn Phe Arg Val Met Leu Val Lys Val Gly Glu Gly Glu Glu Gly
                85                  90                  95

Gln Trp Ser Val Lys Thr Lys His Gln Thr Tyr Ser Ile Pro Glu Asp
            100                 105                 110

Ala Met Thr Gly Thr Ala Glu Met Leu Phe Asp Tyr Ile Ser Glu Cys
        115                 120                 125

Ile Ser Asp Phe Leu Asp Lys His Gln Met Lys His Lys Lys Leu Pro
    130                 135                 140

Leu Gly Phe Thr Phe Ser Phe Pro Val Arg His Glu Asp Ile Asp Lys
145                 150                 155                 160

Gly Ile Leu Leu Asn Trp Thr Lys Gly Phe Lys Ala Ser Gly Ala Glu
                165                 170                 175

Gly Asn Asn Val Val Gly Leu Leu Arg Asp Ala Ile Lys Arg Arg Gly
            180                 185                 190

Asp Phe Glu Met Asp Val Val Ala Met Val Asn Asp Thr Val Ala Thr
        195                 200                 205

Met Ile Ser Cys Tyr Tyr Glu Asp His Gln Cys Glu Val Gly Met Ile
    210                 215                 220

Val Gly Thr Gly Cys Asn Ala Cys Tyr Met Glu Glu Met Gln Asn Val
225                 230                 235                 240

Glu Leu Val Glu Gly Asp Glu Gly Arg Met Cys Val Asn Thr Glu Trp
                245                 250                 255

Gly Ala Phe Gly Asp Ser Gly Glu Leu Asp Glu Phe Leu Leu Glu Tyr
            260                 265                 270

Asp Arg Leu Val Asp Glu Ser Ser Ala Asn Pro Gly Gln Gln Leu Tyr
        275                 280                 285

Glu Lys Leu Ile Gly Gly Lys Tyr Met Gly Glu Leu Val Arg Leu Val
    290                 295                 300

Leu Leu Arg Leu Val Asp Glu Asn Leu Leu Phe His Gly Glu Ala Ser
305                 310                 315                 320

Glu Gln Leu Arg Thr Arg Gly Ala Phe Glu Thr Arg Phe Val Ser Gln
                325                 330                 335

Val Glu Ser Asp Thr Gly Asp Arg Lys Gln Ile Tyr Asn Ile Leu Ser

```
              340             345             350
Thr Leu Gly Leu Arg Pro Ser Thr Thr Asp Cys Asp Ile Val Arg Arg
            355             360             365

Ala Cys Glu Ser Val Ser Thr Arg Ala Ala His Met Cys Ser Ala Gly
            370             375             380

Leu Ala Gly Val Ile Asn Arg Met Arg Glu Ser Arg Ser Glu Asp Val
385             390             395             400

Met Arg Ile Thr Val Gly Val Asp Gly Ser Val Tyr Lys Leu His Pro
            405             410             415

Ser Phe Lys Glu Arg Phe His Ala Ser Val Arg Arg Leu Thr Pro Ser
            420             425             430

Cys Glu Ile Thr Phe Ile Glu Ser Glu Glu Gly Ser Gly Arg Gly Ala
            435             440             445

Ala Leu Val Ser Ala Val Ala Cys Lys Lys Ala Cys Met Leu Gly Gln
            450             455             460

<210> SEQ ID NO 3
<211> LENGTH: 1158
<212> TYPE: PRT
<213> ORGANISM: Homo sapiens

<400> SEQUENCE: 3

Met Ala Ala Val Arg Gly Ala Pro Leu Leu Ser Cys Leu Leu Ala Leu
1               5                   10                  15

Leu Ala Leu Cys Pro Gly Gly Arg Pro Gln Thr Val Leu Thr Asp Asp
            20                  25                  30

Glu Ile Glu Glu Phe Leu Glu Gly Phe Leu Ser Glu Leu Glu Pro Glu
            35                  40                  45

Pro Arg Glu Asp Asp Val Glu Ala Pro Pro Pro Glu Pro Thr Pro Arg
            50                  55                  60

Arg Val Arg Lys Ala Gln Ala Gly Gly Lys Pro Gly Lys Arg Pro Gly
65                  70                  75                  80

Thr Ala Ala Glu Val Pro Pro Glu Lys Thr Lys Asp Lys Gly Lys Lys
                85                  90                  95

Gly Lys Lys Asp Lys Gly Pro Lys Val Pro Lys Glu Ser Leu Glu Gly
            100                 105                 110

Ser Pro Arg Pro Pro Lys Lys Gly Lys Glu Lys Pro Pro Lys Ala Thr
            115                 120                 125

Lys Lys Pro Lys Glu Lys Pro Pro Lys Ala Thr Lys Lys Pro Lys Glu
            130                 135                 140

Glu Pro Pro Lys Ala Thr Lys Lys Pro Lys Glu Lys Pro Pro Lys Ala
145                 150                 155                 160

Thr Lys Lys Pro Pro Ser Gly Lys Arg Pro Pro Ile Leu Ala Pro Ser
                165                 170                 175

Glu Thr Leu Glu Trp Pro Leu Pro Pro Pro Ser Pro Gly Pro Glu
            180                 185                 190

Glu Leu Pro Gln Glu Gly Gly Ala Pro Leu Ser Asn Asn Trp Gln Asn
            195                 200                 205

Pro Gly Glu Glu Thr His Val Glu Ala Gln Glu His Gln Pro Glu Pro
            210                 215                 220

Glu Glu Glu Thr Glu Gln Pro Thr Leu Asp Tyr Asn Asp Gln Ile Glu
225                 230                 235                 240

Arg Glu Asp Tyr Glu Asp Phe Glu Tyr Ile Arg Arg Gln Lys Gln Pro
                245                 250                 255

Arg Pro Pro Pro Ser Arg Arg Arg Arg Pro Glu Arg Val Trp Pro Glu
```

```
                260             265             270
Pro Pro Glu Glu Lys Ala Pro Ala Pro Glu Glu Arg Ile Glu
        275             280             285
Pro Pro Val Lys Pro Leu Leu Pro Pro Leu Pro Pro Asp Tyr Gly Asp
        290             295             300
Gly Tyr Val Ile Pro Asn Tyr Asp Asp Met Asp Tyr Phe Gly Pro
305             310             315             320
Pro Pro Pro Gln Lys Pro Asp Ala Glu Arg Gln Thr Asp Glu Glu Lys
            325             330             335
Glu Glu Leu Lys Lys Pro Lys Lys Glu Asp Ser Ser Pro Lys Glu Glu
            340             345             350
Thr Asp Lys Trp Ala Val Glu Lys Gly Lys Asp His Lys Glu Pro Arg
            355             360             365
Lys Gly Glu Glu Leu Glu Glu Glu Trp Thr Pro Thr Glu Lys Val Lys
            370             375             380
Cys Pro Pro Ile Gly Met Glu Ser His Arg Ile Glu Asp Asn Gln Ile
385             390             395             400
Arg Ala Ser Ser Met Leu Arg His Gly Leu Gly Ala Gln Arg Gly Arg
            405             410             415
Leu Asn Met Gln Thr Gly Ala Thr Glu Asp Asp Tyr Tyr Asp Gly Ala
            420             425             430
Trp Cys Ala Glu Asp Asp Ala Arg Thr Gln Trp Ile Glu Val Asp Thr
            435             440             445
Arg Arg Thr Thr Arg Phe Thr Gly Val Ile Thr Gln Gly Arg Asp Ser
            450             455             460
Ser Ile His Asp Asp Phe Val Thr Thr Phe Phe Val Gly Phe Ser Asn
465             470             475             480
Asp Ser Gln Thr Trp Val Met Tyr Thr Asn Gly Tyr Glu Glu Met Thr
            485             490             495
Phe His Gly Asn Val Asp Lys Asp Thr Pro Val Leu Ser Glu Leu Pro
            500             505             510
Glu Pro Val Val Ala Arg Phe Ile Arg Ile Tyr Pro Leu Thr Trp Asn
            515             520             525
Gly Ser Leu Cys Met Arg Leu Glu Val Leu Gly Cys Ser Val Ala Pro
            530             535             540
Val Tyr Ser Tyr Tyr Ala Gln Asn Glu Val Val Ala Thr Asp Asp Leu
545             550             555             560
Asp Phe Arg His His Ser Tyr Lys Asp Met Arg Gln Leu Met Lys Val
            565             570             575
Val Asn Glu Glu Cys Pro Thr Ile Thr Arg Thr Tyr Ser Leu Gly Lys
            580             585             590
Ser Ser Arg Gly Leu Lys Ile Tyr Ala Met Glu Ile Ser Asp Asn Pro
            595             600             605
Gly Glu His Glu Leu Gly Glu Pro Glu Phe Arg Tyr Thr Ala Gly Ile
            610             615             620
His Gly Asn Glu Val Leu Gly Arg Glu Leu Leu Leu Leu Met Gln
625             630             635             640
Tyr Leu Cys Arg Glu Tyr Arg Asp Gly Asn Pro Arg Val Arg Ser Leu
            645             650             655
Val Gln Asp Thr Arg Ile His Leu Val Pro Ser Leu Asn Pro Asp Gly
            660             665             670
Tyr Glu Val Ala Ala Gln Met Gly Ser Glu Phe Gly Asn Trp Ala Leu
            675             680             685
```

-continued

```
Gly Leu Trp Thr Glu Glu Gly Phe Asp Ile Phe Glu Asp Phe Pro Asp
            690                 695                 700

Leu Asn Ser Val Leu Trp Gly Ala Glu Glu Arg Lys Trp Val Pro Tyr
705                 710                 715                 720

Arg Val Pro Asn Asn Asn Leu Pro Ile Pro Glu Arg Tyr Leu Ser Pro
                725                 730                 735

Asp Ala Thr Val Ser Thr Glu Val Arg Ala Ile Ile Ala Trp Met Glu
                740                 745                 750

Lys Asn Pro Phe Val Leu Gly Ala Asn Leu Asn Gly Gly Glu Arg Leu
            755                 760                 765

Val Ser Tyr Pro Tyr Asp Met Ala Arg Thr Pro Thr Gln Glu Gln Leu
770                 775                 780

Leu Ala Ala Ala Met Ala Ala Arg Gly Glu Asp Glu Asp Glu Val
785                 790                 795                 800

Ser Glu Ala Gln Glu Thr Pro Asp His Ala Ile Phe Arg Trp Leu Ala
                805                 810                 815

Ile Ser Phe Ala Ser Ala His Leu Thr Leu Thr Glu Pro Tyr Arg Gly
                820                 825                 830

Gly Cys Gln Ala Gln Asp Tyr Thr Gly Gly Met Gly Ile Val Asn Gly
            835                 840                 845

Ala Lys Trp Asn Pro Arg Thr Gly Thr Ile Asn Asp Phe Ser Tyr Leu
850                 855                 860

His Thr Asn Cys Leu Glu Leu Ser Phe Tyr Leu Gly Cys Asp Lys Phe
865                 870                 875                 880

Pro His Glu Ser Glu Leu Pro Arg Glu Trp Gly Asn Asn Lys Glu Ala
                885                 890                 895

Leu Leu Thr Phe Met Glu Gln Val His Arg Gly Ile Lys Gly Val Val
                900                 905                 910

Thr Asp Glu Gln Gly Ile Pro Ile Ala Asn Ala Thr Ile Ser Val Ser
            915                 920                 925

Gly Ile Asn His Gly Val Lys Thr Ala Ser Gly Gly Asp Tyr Trp Arg
930                 935                 940

Ile Leu Asn Pro Gly Glu Tyr Arg Val Thr Ala His Ala Glu Gly Tyr
945                 950                 955                 960

Thr Pro Ser Ala Lys Thr Cys Asn Val Asp Tyr Asp Ile Gly Ala Thr
                965                 970                 975

Gln Cys Asn Phe Ile Leu Ala Arg Ser Asn Trp Lys Arg Ile Arg Glu
            980                 985                 990

Ile Met Ala Met Asn Gly Asn Arg Pro Ile Pro His Ile Asp Pro Ser
            995                 1000                1005

Arg Pro Met Thr Pro Gln Gln Arg Arg Leu Gln Gln Arg Arg Leu
     1010                1015                1020

Gln His Arg Leu Arg Leu Arg Ala Gln Met Arg Leu Arg Arg Leu
     1025                1030                1035

Asn Ala Thr Thr Thr Leu Gly Pro His Thr Val Pro Pro Thr Leu
     1040                1045                1050

Pro Pro Ala Pro Ala Thr Thr Leu Ser Thr Thr Ile Glu Pro Trp
     1055                1060                1065

Gly Leu Ile Pro Pro Thr Thr Ala Gly Trp Glu Glu Ser Glu Thr
     1070                1075                1080

Glu Thr Tyr Thr Glu Val Val Thr Glu Phe Gly Thr Glu Val Glu
     1085                1090                1095

Pro Glu Phe Gly Thr Lys Val Glu Pro Glu Phe Glu Thr Gln Leu
     1100                1105                1110
```

-continued

Glu Pro Glu Phe Glu Thr Gln Leu Glu Pro Phe Glu Glu Glu
    1115                1120                1125

Glu Glu Glu Glu Lys Glu Glu Ile Ala Thr Gly Gln Ala Phe
1130                1135                1140

Pro Phe Thr Thr Val Glu Thr Tyr Thr Val Asn Phe Gly Asp Phe
    1145                1150                1155

<210> SEQ ID NO 4
<211> LENGTH: 469
<212> TYPE: PRT
<213> ORGANISM: Homo sapiens

<400> SEQUENCE: 4

Met Phe Ser Glu Gln Ala Ala Gln Arg Ala His Thr Leu Leu Ser Pro
1               5                   10                  15

Pro Ser Ala Asn Asn Ala Thr Phe Ala Arg Val Pro Val Ala Thr Tyr
            20                  25                  30

Thr Asn Ser Ser Gln Pro Phe Arg Leu Gly Glu Arg Ser Phe Ser Arg
        35                  40                  45

Gln Tyr Ala His Ile Tyr Ala Thr Arg Leu Ile Gln Met Arg Pro Phe
    50                  55                  60

Leu Glu Asn Arg Ala Gln Gln His Trp Gly Ser Gly Val Gly Val Lys
65                  70                  75                  80

Lys Leu Cys Glu Leu Gln Pro Glu Lys Cys Cys Val Val Gly Thr
                85                  90                  95

Leu Phe Lys Ala Met Pro Leu Gln Pro Ser Ile Leu Arg Glu Val Ser
            100                 105                 110

Glu Glu His Asn Leu Leu Pro Gln Pro Pro Arg Ser Lys Tyr Ile His
        115                 120                 125

Pro Asp Asp Glu Leu Val Leu Glu Asp Glu Leu Gln Arg Ile Lys Leu
    130                 135                 140

Lys Gly Thr Ile Asp Val Ser Lys Leu Val Thr Gly Thr Val Leu Ala
145                 150                 155                 160

Val Phe Gly Ser Val Arg Asp Asp Gly Lys Phe Leu Val Glu Asp Tyr
                165                 170                 175

Cys Phe Ala Asp Leu Ala Pro Gln Lys Pro Ala Pro Pro Leu Asp Thr
            180                 185                 190

Asp Arg Phe Val Leu Leu Val Ser Gly Leu Gly Leu Gly Gly Gly
        195                 200                 205

Gly Glu Ser Leu Leu Gly Thr Gln Leu Leu Val Asp Val Val Thr Gly
    210                 215                 220

Gln Leu Gly Asp Glu Gly Glu Gln Cys Ser Ala Ala His Val Ser Arg
225                 230                 235                 240

Val Ile Leu Ala Gly Asn Leu Leu Ser His Ser Thr Gln Ser Arg Asp
                245                 250                 255

Ser Ile Asn Lys Ala Lys Tyr Leu Thr Lys Lys Thr Gln Ala Ala Ser
            260                 265                 270

Val Glu Ala Val Lys Met Leu Asp Glu Ile Leu Leu Gln Leu Ser Ala
        275                 280                 285

Ser Val Pro Val Asp Val Met Pro Gly Glu Phe Asp Pro Thr Asn Tyr
    290                 295                 300

Thr Leu Pro Gln Gln Pro Leu His Pro Cys Met Phe Pro Leu Ala Thr
305                 310                 315                 320

Ala Tyr Ser Thr Leu Gln Leu Val Thr Asn Pro Tyr Gln Ala Thr Ile
                325                 330                 335

```
Asp Gly Val Arg Phe Leu Gly Thr Ser Gly Gln Asn Val Ser Asp Ile
                340                 345                 350

Phe Arg Tyr Ser Ser Met Glu Asp His Leu Glu Ile Leu Glu Trp Thr
            355                 360                 365

Leu Arg Val Arg His Ile Ser Pro Thr Ala Pro Asp Thr Leu Gly Cys
        370                 375                 380

Tyr Pro Phe Tyr Lys Thr Asp Pro Phe Ile Phe Pro Glu Cys Pro His
385                 390                 395                 400

Val Tyr Phe Cys Gly Asn Thr Pro Ser Phe Gly Ser Lys Ile Ile Arg
                405                 410                 415

Gly Pro Glu Asp Gln Thr Val Leu Leu Val Thr Val Pro Asp Phe Ser
            420                 425                 430

Ala Thr Gln Thr Ala Cys Leu Val Asn Leu Arg Ser Leu Ala Cys Gln
        435                 440                 445

Pro Ile Ser Phe Ser Gly Phe Gly Ala Glu Asp Asp Leu Gly Gly
    450                 455                 460

Leu Gly Leu Gly Pro
465

<210> SEQ ID NO 5
<211> LENGTH: 39000
<212> TYPE: DNA
<213> ORGANISM: Homo sapiens

<400> SEQUENCE: 5
ccagacatag gcaaggcgca aggtgataca gtaggcagcc accatggggg ccaggaggct      60
ccagcagagg ccacacaacc agcccagaat ccaggacaga gagctggaat ggagacaggg     120
aagccagata ccaggccaga ctggccaggt gctacaggcc tgtgggccag gccaggcttg     180
gggacttcgt cctgggtgtg aaggagacag gcacccctga ggccttccct ctgcatctcc     240
agcccaagct aagcgcaaac tcttaggttg gagtaaggag taacccctg ccaagtttct      300 cctgtcctca ggctccaccc accacctatg ctgcctggcc catggggca cacgctcagg      360 cccagcctgg gaaagcaact gcacctgcct gtgctatgct ggcccttctc agcctcaatg     420
ccctcctccc tccccgacgc accctcgtgg ccccgctgg gccccctgat gcaccctcat      480
gtctccatgg caacctgctc agagtgtggc cctgcccttg ctcccctcc acacctgtgt      540 cccaggcagt gccacggcac tttcctaaac agaaggatgg gcttcaaaac agtcccagac     600
actaaacaca cctgcatttt gggtccaagt aacttctgac aagacgagtg ccccctacaca    660 ctctcagtcc tatccactat gggcaaggag cctgaaggat cccccagaac tggctaaagc     720
cctcagtctc ctcctccacc ctgagcacct tcacgcggca gagtggccct ggatgtcagc    780
ttcttgctcc ccatggtctg cacctggaca ggtgctctca ggtgtgtggg tgggcaggtg    840
gcaggtccca agagccaggt gcaaagaatc taggccagtg cccacgagtg ctgcagtgtc    900
tgtccccagc atggtatcta gggctccact tgcctatcag ctgtaatcgg aggaggcttt    960
ccaggccagg cctcccccag gaaggctgca ggcactgcgg atcgtgcgcc ctcacatgca   1020
ttattcctga ggcccttctg cagatgccat cagggcagca actctgatga ggtattaggg   1080
cacagcacac agggctaagc caccctgtac tgggccaagc gctacaggca aaaaggacac   1140
caccgacggg catttcattc atcgcttta tttttatata tttttgagag ggagcctcac    1200
tctgtcgccc aggctggagt gcagtggcgc gatcttggct cactgcaact tctccctcct    1260
gggttcaagt gattctcctg cctcagcctc ccgagtagct gagattacag gtgcccgcca    1320
```

```
ccatgcccag ctaactttg tattttagta gacatggggt ttcaccatgt tggtcaggct     1380
ggtctcgaac tcccgacctc aaatgatctg cctacctcag cctcccaaag tgctgggatt    1440
acaggcatga gccactgcac ccggcccatt catcactttt aaatagcacc ctctgaacaa    1500
agctccctgg gccacatgac cctaagggtt accccatccc accccaaccc aggtctggca    1560
ggtcctcaga acaggaaaag ctgagcactg cccaaggctg cttgctgggc cagtcagaga    1620
ggtctctgcc ttccaggatc agaagtacag gctgaaagca gccttgggcc cgcctccctg    1680
ggaggctaca gaggcttcag agggttccct gaactcaaaa ccagatgtga gacttgaatt    1740
tgacttaccc ctggttcacc tcccaaccaa agcaggggtc agctttggct cctccaggaa    1800
ccaggaagct tccaggtacc ctgtggagcc ccctctgctc ctgaaaagtt gccacctgtg    1860
cttggtggga tgccaggtgg tctcagattg accctgggt cagcggtgag ggacaggaag     1920
cctacagcgg gatcaggatg gggatggggc ctcctgtccc atggctctgc agctatgagg    1980
cagctttcct agggtgggtc tcctggctgc agctaagacc aggcaacagg attcagcaat    2040
gacagggctt cttctactcc agggctccct cacctggtta acagcaaaaa agaaaataca    2100
gttcctgcta gcaaggtcta tagaaaggag gtgaaggagt caggcctgca gctacctctc    2160
ctggacagga gctggtcagg ataacttgga cccttgcatg cggcaggccc acaggcacac    2220
agcatgaggc cactctctcc cccgggggaa gggcttggtg aagaaaggat tcccctgaag    2280
cacaaagaaa gcacaggacc actgtgaaat ttcaagacaa ctttatccag acaggcgcct    2340
ctcaaataga acacagggaa gttaggcagc agttactaaa atacagtctc gccaaatgat    2400
ttacaacaga acacaacagg agcaggggat ctgtgggtgg ggctgggctg ggccctctat    2460
ctcacagggc ctgagtcaag ccagcccgcc ctgcaaggca ggggctgacc tgcaagcgga    2520
gatctcactt cctcttaccc caaattcata cctccatttt ccccgccccc atctctcccc    2580
agggtcctca gtgggaaag ggagaggtag catccctcgg atccaggccc actccactcc     2640
gtctccggca ccagtgggca ggctgagtct gggcctcaag gggccctggg cttagggtat    2700
ctatggcagt aggaaaatga catgdacagg ctcttcaggg gtaggctaaa gtcctctggc    2760
cagcagtacc cagagaaaat gggcagcagc aggtaaacca gccaggaggt ggagtcctct    2820
gaacccacag cagaccccac cctcctgccc agccctgcc cacattgggg gtcaggacca     2880
ctgagactct ggtcaggaca gtgggtgctc tcagcagtgt ggcaagctca gagcagagct    2940
cccaaggacc ataccacact ggttcaaaac ccataggtga caccatccca gcagaagctt    3000
ccatgggtgc tggatcccag ggctgcatcc tgagcacagg tgggcagact ggaacataac    3060
actaggaccc aagggatcca gaacatttta ggcccatctc ctgggctgct ccagcctgtt    3120
gccatgactt gggcagtgag tgggcctcct gccaggtggc agggcacagc ttagaccaaa    3180
cccttggcct ccccctctg cagctacctc tgaccaagaa ggaactagca agcctatgct     3240
ggcaagacca taggtggggt gctgggaatc ctcggggccg gctggcaccc actcctggtg    3300
ctcaagggag agacccactt gttcagatgc ataggcctca ggcggttcaa ggcagtctta    3360
gagccacaga gtcaaataaa aatcaatttt gagagaccac agcacctgct gctttgatcg    3420
tgatgttcaa ggcaagttgc aagtcaaggc aagtgtccca gaggccctgg gcagctgagt    3480
gcacctgtgt ttgatcttcc cctgatgatg gacactccca gctgaccatc caaacaccag    3540
gaaaacatcc ccctttcctg ggctcagttc ctagtctact tgctggtacg aacccaaccc    3600
acacactccc cgcccacaat gcagctcctt ccaaatcctc ccacaagcca cctttgtggg    3660
acttggaagc tgcttaggat gggccctgcc ctctgcggga agccaatcct agcagaaagg    3720
```

```
taagctaaac aacagtctca gaatctgaga cccagtgact gttcccccg ccccaggcct    3780
tgggcctgaa gtgggggcct gcctgtggcc tctgtggtgg gctcactccc accccaaca    3840
gtggccccag gagaggcttt cccaagagtc ttcaaactcc acccacccca gccctagcat    3900
cagggactcc ccacccccca ctggagtgtt aatatcatta atgtacaaat aagatccaaa    3960
gatataccaa agatcgagaa acagctggct ccgacctccc tcccacagag ccttcccagg    4020
gttagctgaa aaagagccct ttggcatcta cagaagccag tcggagttta tggtttcatt    4080
tgcccaaaaa tacaccttttg gggacctcaa attctttcca agaatcacta ccacacatat   4140
gaatttgaac attcgccacc cttccaccat ccatttctcg caggaacttc aaaataaaaa    4200
tggccagtct gcccccactc tggctcctcg tctatggctg tctcttcttt tccagggggct   4260
gcagttctga tgtgaatgat ggtgccattc cagcattggg cctctggcag gctgcatcac    4320
atgatggcac agcatgagtt ttgtttccgg gccttggaaa aaaacaaaga ggagctgaga    4380
aggaggactg acgaagtaag ggaagcccca atcctggcag gcgtggcaga gggagctcca    4440
caggacacag ccaggcagag aaactagcac tagaacaggg tgggggtgga ggccttgagg    4500
gaagctgtcc acaagcaatt cccatcacca agcacaaggc gggccccggc ttccaaaact    4560
agtctgggat cctttttcct ttcttttctc acccccatt aatgctatca aaaagtgagt    4620
aaaattccta cagttaggcc aggtacaaac aaaggaccaa taatacaaat gggattggca    4680
gaatatctta actttgcccc actcctgtct tcacacaatg ctatctgacc accacggtgg    4740
tgtttcttcc tagaagatgg tcctgaggac aacagatgtg gttcccactt gggatgtggt    4800
ttgtggggac cactgttgcc accttctctc ttgctttctg gtcacagact atcttcctaa    4860
tcccacctag ccatctccct ccaatgtgca catgaaagca aatgtgtgtg acagaccaa    4920
gtaaatttgt ccctatgact atccaaccat gggccaacag tgccatctcc acataggaag    4980
acatgagcac tgacctgaga gaaagcggca gtcagcagca cccatccttg tcaattaaat    5040
attttctgtc aaagggaaat taaaagctta agaacctctt caggaaggct gaattgcttg    5100
catcttaaag acttatgtct actcagcaga aagaggaata agattcaaca gtaaatctct    5160
ggtgatcaga acttgaacca gccttcctgg actgggagta ggagttcaga aatcagccag    5220
agcagcagag ggcagagcag aggcaggagt ggaacaaggc ctcggcccgc atcgactcca    5280
acggcgccca agtgaactgc ctccaaccac ctgggcctga ggcgctcacc ttaggctctt    5340
gccgcacaag gaatcatcca ccatgattca acagtctaag aaagacccgt tcatagtgga    5400
gagtgccaga agcagcaagc tgcgactgct ctctagagag aacacccagg aggcagcagg    5460
tgctgggtac tcacagtttt atagaaggct ttagactgtg ttcccagcac ctcggatttg    5520
gacaccaagt catctagctt ctcacctcgc tctaacagag actccatggt gttgtgctgg    5580
acaaaaaaga aaagagaatc cagctctgtt cagtacgtgc cctgacatga gcccctcata    5640
tttcagtcat gggggaaagt gccttacctg ggttcctctc caacacacac aaacttcacc    5700
tctaggtgtc gagactcggt ccaagaatag ttactgtcca agtggatgga acagaacctg    5760
gtgacattcc cgtgaaatct agaagatcta actgggatgt agcagacttc ccaaaaagct    5820
gtccccagca caggcttaga taaccagcac tccaggaaaa ctcatatata tatatacaca    5880
cacatttata tatacatttg tgtgtgtgtg tgtgtgtgca cgcacatgtg cgtgtgcatg    5940
gagctttgga aaaagagta gctgggcact atatgattgt actgggttgg agagtgaccc    6000
acaccgcacc ccccaacccc aaccgcatcc cagaaattaa catccccaga atctctgaat    6060
gtgaccatat ttagaaaatag ggtcttggca gatgtaacta gttaggaaga ggtaatactg    6120
```

```
gattagggtg gcatctaatt ccatgactga tgtcctggta agaaacggaa acacacacac      6180
agaaggtcac gtgacggcag aggcagagcc tgaagtgatg cacctctaat ccaaggaatg      6240
ccaaggatgg ccagcagcca ccagaggctg gagagaggcc tgggacagac actcagagcc      6300
ccaaaagaca ccagccaggc ccacagagct atctgttaaa agcaaatatt tgagggtttc      6360
tgttgacagc agccacagga aacaaaaggc ggtgggaaat ggctattgag cacttgatgt      6420
gaggcaagtc caaactgagc agcgctctga gtacagacac accagatttc agatgcaaac      6480
tcacacatgc ttcattagta agttttatac tgaaaaaaaa acaagtttta taccgattac      6540
atgttgaaaa aattgtattt ggatatactg cgttaagtaa aatatataat taaattaaat      6600
tctacctatt ttccttttat catttttaaaa tatggctcct agaaaattct aagttacaca      6660
catgccccaa atatataccca gacagcacta tgacagaaca tgtcctgcct tctaaatggg      6720
ctatgtccta aatgtcatca ctacaaactc tgacttagga aatgaaaaca ctgaccccat      6780 gggaagggt ctagagatgg agacctcaca agagccagca gctctgctgc cagggccctc       6840
aggaagcagc agctcgcttc tctcctcaga tggccactgc tgcagcagct agatgcacac      6900
atgaagcgcc atagaacaag gagccagcaa gaatgtcctt catccctaca cacagctgag      6960
cgactcaaat ttttaacaca gaaagttaac tgattcagat atgcacacca atcatctaga      7020
ttttacaact gcagctagat gaggctgggt gaataggact catccactcc ccaccgtggg      7080
gagaggagaa acagcgggtg tcccaggtgt catggtactc agactaggac ttgagcaaca      7140
gaaagagatg gcttgaggag aaaacggaga aatgccacct aggtggtaag aaagctcaca      7200
aggtttcaaa agacacagat accatgagac tttcacatct atcgttcatt ccaaagccac      7260
gttatttgga gtgcagtcag cacacctgtg tttgaagccc ctgggatgct ttttataaaa      7320
tgcaggttcc caggctccat cgcaggccaa caactccaac cccaggagac gctgatgtac      7380
acactaaagc tatgcctgtg taaatggtaa agctttgtat gtgggtttca atccactcca      7440
ggtatctatc aactgctgag catggtataa actaggcact gtatcatgag caggatggaa      7500
agatgtccca gtgctcatac gctggtcagg gagacatgta aacaagcagt gacaaaactg      7560
tgacatctgg tcagaaaggc ccaaccttca ggcgcctgtg tgtgagctgg gcaagaaagg      7620
gtataagaga gaacagggcc cagtcaggag actgtgagtt agtttgcact ttatcctggg      7680
gcggatctga gagctgctga agggttctaa gttgtgcaga tcaatgacta ctctctggtg      7740
gacagactgg aggtgagcag gaggcaaggg gaccacttag aggcaaaggc tgtaagagaa      7800
aaacctgaga aaaacagata gctgcttaca ttccacttgt atgcaaaaat ttaaaaaaaa      7860
agagttgaag caacagttac aaatcaggag atttcagctc aaaatgcagg gttctggctc      7920
ttttcaaagg ggcctatgtg acaaccctgg gcccatattc cagaagctgc cctgtggtca      7980
gtgcacggtg cttcaatctg ttcaccttca atgcaaacgc tgcaagggga ggcacctgtg      8040
gggtgtggag gcacccgaaa ccctaacaaa ggcaccaggg tggaatcca ggtcttcaga       8100 agccaaaccc taggaaccca gtaaatggtc agacaggcag tagccatgag gaagggagac      8160
ttgagggttc cactggttcc cagcttggtc ccctagaaac aatgggtgcc attaaccaag      8220
agaagggtat aggaaagaca gtctgatgcc cggggtgggg gaagggtgg gcaatcccac       8280 ttgctggaga gtgccgtggt tactattata ttaaaacgag gatggatctg tgcatgcctg      8340
gccagtggaa atcgcacccc cgcctcagtt cttgggcttg ctctccatct tcctgcttac      8400
cagaatgatt ttggtctcat ctagttcggc ctgcacttta gtcatgggat cagcttctcg      8460
tgggttctag gaaagagtga aaaataataa agtcaggact ggagtggcta cctgcaaaca      8520
```

-continued

```
aaacctaaaa ctgaggaagc tggacaaact ttcacaggtt aaaaaccaca gcctgggccg      8580
ggcacagtgg ctcacgcctg taatcccagc attttgggag gatgaggcgg gtggatcacc      8640
agagatcaag agttcgagac cagcctgacc aacatggtga aaccgtctct actaaaaata      8700
caaaaattag ccaggcgtgg tggcacatgc ctgtaatccc agctactcgg gaggctgagg      8760
caggagaatc gcttgaaccc aggaggtgca ggttgagtga gccgagattg cgccactgca      8820
ctccagcctg ggaaacagag tgagactcca actcaaaaaa caaaaaacaa aaaaaaaac      8880 ccacagcctg tttaacatgt aacagaaacc caaagcctgc ctagagcttg ggttccccgg      8940
tctgaacgta gattctctgt tttccaaaca gtaaggcttg agagaggaca ccagcatcag      9000
aagctgtcag aagtaattag accagaacta tcagggcagt tggctttttc agtttcacat      9060
ggattctggg ccacatggtg tctgctgaag cttcctttaa ccctacctgg tatctactga      9120
ggtgaccatc cagggctggg taatggattg tagcagggga tcctactggc cagtctatcc      9180
tgtcgacttg cttggagaat tcatctagta cctgcaagac aaaggagact caacaagcct      9240
cccactgtgc actcaccagt ggtctcaatg acagggcttc accoctgagc acctcaccct      9300 gaatgaggct ccttggcctt cacagcccag gaaggaggaa tgaggggggac atataatggc      9360 aacagagaaa atctaggcta aagttctttc caaatttta tcattaaaac atatcctaaa      9420
tattctgaga atcaaaagta tgcccagccc gagatgaacc tcacttgggg agtaataaag      9480
gtatttgaat tttaaactac agatttccag aaaaaagggg cactggtcct ctaattttcc      9540
aaagcaattt tttaaaaaag agaattaggt cccctagatt taagaaacca ccagattcca      9600
tgtgtttgga ggtattttgg tgctctgggg tataggatga agcctctgac ttcaaagagt      9660
taatattagt aattagcacc gtacgcaaaa aaatttaaag aatgcttagg tgctaagctc      9720
tgtggtgcaa ctgactgaca tcaaggtaga gggatgcagc aactgcagga ggcaatgggg      9780
agagtgaagg cattcaagag ggagactcct tgagcagaag cacaggggc gagaacacaa      9840 ggcacagctg tctccgaggg tcccatccca gagaatagat gctatgactc agtggcctag      9900
acccagctca catgagggac agcaccgggg aggaaaccca tacagggatg ccaaattgtc      9960
tcttgggttg cagggaaggg ggctgaaaaa tgtgttgact ttggacacat catttcatcc     10020
cttatgtctc agggactgcc atcaacccct gtcccagtcc ataaatgtgc ccattcatca     10080
tccaagtcca ggagaggcaa ataaaaaact caccttctcc agcaaggtaa aggccacccg     10140
ggatgggtat tcattgtcag caatgaccac acctgcaaga ctatcattcc ggacgtagac     10200
gtggcacaga tagtctaagg agacaagaga tcagacacat ggatgctgac atgagggctt     10260
cagacttctt ttaatccccc caaatcaaag catccaatgt taggccaaat gaagccactc     10320
ggaagctcaa tagctctggg caagtcttgt ggagaggctt agcagcacag cccaatgggc     10380
cacacacagg agcttggccc aacgcctgct ttaggaccag taaatacccca gaggcccagt     10440 atgcaaagcc agggcttaaa gaaacagcca gtggtgcaga aaacacaccc ttgacaacat     10500
ggccccagga gcatttccaa gtgtattcct taagctcggg tcaggccaag ctatatctta     10560
gggatctgga gcccttgggg ctctgtgctg ctcccaaact tagggaaccc tggacaagcc     10620
aagaggcctc tgcttctta aaaaatcttt tcagagcagc caaaagacag gaaattaccc     10680
cccagggcct cagtcttcca tattatagca acctgctggg tttgctccac tctggtgggt     10740
gactgggagt aggggggtta gtctagaaaa agattagcta ctgccagcta aggcctccag     10800
agcactgtgc taaatcctc atatgattga aaggtacagt tgtacaggtc ttccgcaaaa     10860
tattcacaat ccacaggatt gttcatttcc atcactttga aaggattcag agttgataca     10920
```

```
gctaaccata tccccaagga aagagaaatg taaggattac agcttacaaa taagaacctt    10980
cttgtcctta aggatctgac ccagaagatt ccaatgctaa acaacagaaa aacaaataaa    11040
agaggaggga atgatggtga gcccctgaaa tcagaaaaga gcagagataa atgagaacaa    11100
gaatgaggag gaggaagagg acaggggtt gtcaccaatg ctctccagat tttgtatacc     11160
atccccaatt aagattcaaa catggggtca aagtgcatac cctccaaaga aactgagaac    11220
ctggtcagtg gaggaattgt cttttaagtaa taaacgtggg aagggcaggc acagtttgaa   11280
gaacagagca agaacactga aatatttgtg atgcgatttc acttctatga tgttaatagc    11340
acagagatcc cacataaagt gtatatagtc aatcctgcct gtatcataac tgacatttat    11400
atcatcaatt cagtaactct atgtcacgtg acttgaggtt agcataagtg tgagatgatc    11460
tttgtcccta cctgatgaaa ctcatgtaac tcttctccctga tctgtctgta taacatacac   11520
atctaaataa atgcctaaac ctgaattatc agaagaaaa aatagttttt tcagattcct     11580
gatcaaaaaa tctacgatgc acagaataca tatagtacct caacagtgct agctggaaat    11640
ccttttttga ggggtctgca actctgaaga ggatagggaa gaatacgata tgaaggctgc    11700
ttactgctcc aaaagagtca gaccctaatc ttaaatgagt ctaagtttga gggcaatttt    11760
atctgggaag ctcagacttc aacagtgggc acagaattct gcataaatag gaaaaggaag    11820
aggtgggaaa gagagaacaa gctagaggag gagtagggtc ccagtagaaa ggagaaagct    11880
gggtgctatg tgaggtgagg catggcagcc aggccagcac acgcacagaa gttggagggt    11940
cttcttacct tgttctttga cagaagctct agtgcctttc gatgagcgct ccacaatcag    12000
ttgactcgtg aaggtcatga attcctgaac gctaagaaac acaaaatgta tttattgcct    12060
acttcttatc accttgtccc caacacagtg gaaagtgacc tctgggctta tacattaagt    12120
agacattgct tcttggtttc attcctttcc ctcccatccc tagtaacaaa cactctataa    12180
atgagcacaa atactgataa ttatgaatta tcatcaccat gaaagctcca tctgtttgct    12240
acctggctca ccaaaacagg tgaattttct gggggtttt tccacaggat acagtcaatt     12300
ttacattttg gtgaatgcat aatttggaat gcaatggaaa aacaagaggc aggtcctgct    12360
ctcaaggtcc caataacttc caagaagcag gacatttata agaactgcac tagaagaata    12420
gtgtgcaaaa actgtcaggc agaaatgcac aaccatttat ggctgtgtcc acatgacaga    12480 cccctcgcaat gccacataca cccatagtga gtgctggctc aggtctgctg gggctcgtcc    12540
acagaacgag cgcaagacac tctggatgga acaaaaggaa aactgctcat ccaagacaaa    12600
gaagtgggaa atggctcata caagggtga agggagaag gtccatcatg ggctcaacag      12660
agagatctat ccagaacaga acagtcacag gagatggtac agccagagga agaggtgctg    12720
acaaggagcc tccaactgag gatgtgatat aaagggcaac cagggccatc aaagcagggt    12780
gctcaaatgg gagtctgcag caggctccag cagagccata taggtaactg aaggcctgac    12840
tctgggcctg tgtgctgtgc ctccacatta aaaaaatcaa gatttgtgca acagttaaac    12900
gaggtaatac gtgtaaagca cttggaacaa tgcctgcaca cacagtatta cttgttaata    12960
tcttgaggga ctgaagtgat caaaataacc cctcagaaaa gaagacctca acaaggaag    13020 gctttgcagt aaacctagag acagcatttg agacacggct ataagagac aaggaagaa     13080 ctgcattgtg acagcatgta tacaaagacc aaaaaagctg ggaaactact ttttcaactt    13140
tggaatcggg taattatagg gcacaaagga cgtaagtaaa gcggtcttat aagaaaacaa    13200
gctcaggccg gacgtggtgg ctcaagcctg taatcctagc actttgggag gccaaggcag    13260
gcggatcact tgagctcagg agttcgagac cagcctggct aacatggtaa aaccccatct    13320
```

```
ctactaaaaa tacaaaaatt agccgggtgt ggtggtgcgc gcctgtaatc ccagctactt   13380
gggaggctga ggcaggagaa tcacttgaac ccaggaggcg gaggttgcag tgagctgaca   13440
ctgtgccact gcactccagc ctgggtgaca gagcaagact ccatctaaaa taaataaat   13500 aaataaataa atcagctggg acatgtgttg ttttaagaca tattagtaga gatgtccctt   13560
tagtgttgca gctgttagtc attggaaact agtgtgggca tcccaagcag gtgaggtata   13620
agtcctacaa gtgaaatctc tgagaatctt aagtactaat gggaaggaaa aaggaaaaag   13680
aatcagagcc aagttggcac caaaagttcc atctgagaaa agcaacaaca cagagcagtg   13740
aatgtaggcc atggtaaaga ctgcaaagac caagaacccc aagaaggagc taaaagataa   13800
tgcagcaatt ccgcttctgg gtaaatacca aaaaaatgcg agcagggtct tgaagagata   13860
tttgtacatc catgttcata gcagtatcat tcacaatggc tgaaatgtgg aagcaaccca   13920
ggtgtccact gacagatgaa cagataagca aaatgtggtg aataatacaa tggattattc   13980
agccttaaaa aggaaagaaa ttctgatata tgcaacaaga tgcatgagcc ttgaggacat   14040
tatgctacat gaaataagcc agacacacaa aaactatatg attccattta tctaaggtcg   14100
ccagaaaagt caaaatcaca gagacaaatt agaatggcag ttgccatggg ctgggggaga   14160
agggaatgtg tttaatagac acgaatttga taaaaaggag ttctggagac gattgacagt   14220
gatggctgca caacactatc aatctatttc atatcaatgc actcactaca cgcttaaaga   14280
tagtgaagat aaattttgtg taccatttta ccacaattaa aaatattttt ttaaaagaac   14340
tcaaagaagc agaaagtttc aacaaaataa cattttttt tttttacatc cagcaagtcc   14400
ttggcaaaga actctcatca agaaccagct gcactgaagc agggaaaaca gaatccaaac   14460
ggcagattcc atcagatttt gagacaagat gaccatagat accgaccatg tagggtcctc   14520
cttctttcgt gcctgagtca ccccaatccc tcccacgaat ggtctggaag tgtctgtgtt   14580
acttctaaca cgttccagca attaaagcgc cccagaaaca agtaaaagcc tgtaagccct   14640
acagatccca tgcttcattt gcatcttccg tgtggaatcc ttttgtacca ctagtgtcca   14700
actaaaaagc gttaaacctg gctttcagtt ctagctggtt gtgatataac ctcttggtac   14760
ctcagtgact tcacccatta aaacaaaca aaaaaaagta tatcactatc tctcatacag   14820
aattgttggg aagccccgca agaaaatcaa aatatggctc tcaagatgcg gcacccaagc   14880
tcccagagtc agaatcactg ggtgggaagt gttggtctaa aatataaata ccgaggcctc   14940
aatctactaa ttcagaacat cttggcatga agcttggaaa tctgcactac ttcacagtct   15000
ccttaaaatt tttacacgac agaaatttga aaaacactga gtagaaact atattctaga   15060 atggtataag ctcttaaaga gctaatgttg gttcctcaaa ggtagagtcc acggccagat   15120
tccattatag gagaccaagc ccggacagca gaccccgggc cctccccacc ccgcccgcc   15180 tctgactcgg acaccagcct tctcagaccc cgggcactcg gccaccccgc cctgccccta   15240
cccttggcct cctccaccct cccctcatcc ctccgccgac cccaggccca ctccgactcg   15300
gacccccacc ccagtcctct ccgcccgacc gccacggccc accagcctgt gccgctcacc   15360
tggatctctg gaaaaagctg aaggaagaca catcgtatgc ggctttgagc agcaccacct   15420
tggcctcgcc tttgtagagg acgctgaggc tgtacagctt catggctccg cgccctcagg   15480
ccgcccgcct gcccagctgc gggacccgtt ctcagggagc agcgcggccg ccgcccctcg   15540
ggaccgccgc cgcctaccgg cctctcagca gccggctgct gacggggcca ccgccggctt   15600
cctcctcctg gctcgcaatc cacttccgga tccggtcagc ctggttgagg gttctcatac   15660
tccggatgca gaaatgtgag cccggaagta caatgcagcg aggggcggga tgccacgcct   15720
```

```
cgcgtaagct tggcccctcc ctgctcgcca ggtggagtcg ggcgcgcggc gggataccgt   15780
actgtcttgt gctgggtggt gctgggcctc ccacagcggc ctgaacccttct tttttttt   15840 tttttctttt ctttctttt ttaaagtaag cattttttttt attattatac tttaagtttt    15900
agggtacatg tgcacaacgt gcaggtttgt tacatatgta tacatgtgcc atgttggtgt   15960
gctgcaccca ttaactcgtc atttagcatt aagtatatct cctaatgcta tccctccccc   16020 ctcccccac cccacaacag tccccggtgt gtgatgttcg ccttcctgtg tccatgtgtt    16080
cttattgttc aattcccacc tatgagtgag aacatgcggt gtttggtttt ttgtccttgc   16140
aatagtttgc tgagaatgat ggtttccagc ttcatccatg tccctacaaa ggacatgaac   16200
tcatcatttt ttatggctgc atagtattcc atggtgtata tgtgccacat tttaggagga   16260
gcttgtacca ttccttctga aactattcca atcaaaagaa aaagagagaa tcctccctaa   16320
ctcattttat gaggccagca tcatcctgat accaaagggt ggcagagaga gacacaacaa   16380
aaaaagaatt ttagaccaat atccttgatg aacattgaag caaaaatcct cagtaaaata   16440
ctggcaaacc gaatccagca acacatcaaa aagcttatcc accatgatca gtgggcttc    16500 atccctggga tgcaaggctg gttcaacata cgaaaatcag taaacgtaat ccagcatata   16560
aacagaacca agacaaaaa ccacatgatt atctcaatag atgcagaaaa ggcctttgac   16620
aaaattcaac aaccctcatg ctaaaaactc tcaataaatt aggtattgat gggacgtatc   16680 tcaaataat aagagctatc tatgacaaac ccacagccaa tatcatactg aatggacaaa    16740
aactggaagc attcccttttg aaaactggca caagactggg atgccctctc tcaccactcc   16800
ttttcaacat agtgttggaa gttctggcca gggcaatcag gtaggagaag gaaataaagg   16860
gtattcaatt aagaaaagag gaagtcaaat tgtccctgtt tgcagatgac atgattgtat   16920
atctagaaaa ccccatcgtc tcagcccaaa atctccttaa gctgataagc aacttcagca   16980
aagtctcagg atacaaaatc aatgtgcaaa aatcacaagc agtcttatac accaataaca   17040
gacagagagc caaatcatga gtgaactccc attcacaatt gcttcaaaga gaataaaata   17100
cctaggaatc caacttacaa gggatgtgaa ggacctcttc aaggagaact acaaacgact   17160
gctcaatgaa ataaaagagg atacaaacaa atggaagaac attccatgct catgggtagg   17220
aagaatcagt atcgtgaaaa tggccatact gcccaaggta atttatagat tcaatgccat   17280
ccctatcaag ctaccaatga ctttcttcac agaattggaa aaaactaaag ttcatatgga   17340
accaaaaaag agcccgcatt gccaagtcaa tcctaagcca aagaacaaa gctggaggca    17400 tcacactacc tgacttctaa ctatactaca aggctacagt aaccaaaaca gcatgctact   17460
ggtaccaaaa cagagatata gagcaatgga acagaacaga gccctcagaa ataatgccgc   17520
atatctacaa gcatctgatc tttgacaaac ctgacaaaaa caagcaatgg ggaaaggatt   17580
ccctatttaa taaatggtgc tgggaaaact ggctagccat atgtagaaag ctgaaactgg   17640
atcccttcct tacaccttat acaaaaatta attcaagatg gattaaagac ttacatgtta   17700
gacctaaaac cataaaaacc ctagaagaaa acctaggcaa taccattcag acataggca   17760 tgggcaagga cttcatgtct aaaacaccaa agcaatggc aacaaagcc aaaattgaca     17820 aatgggatct aattaaacta aagagcttct gcacagcaaa agaaactacc atcagagtga   17880
acaggcaacc tacagaatgg gagaaaattt ttgcaaccta ctcatctgac aaagggctaa   17940
tatccagaat ctacaatgaa ctcaaacaaa tttacaagaa aaaacaaac acccccatca    18000 acaaatgggc gaaggatatg aacagacact tctcaaaaga agacatttat gtagccaaaa   18060
aacacatgaa aaaatgctca tcatcactgg ccatcagaga aatgcaaatc aaaaccacaa   18120
```

```
tgagatacca tctcacacca gttagaatgg tgatcattaa aaagtcagga acaacaggt   18180 gctggagagg atgtggagaa ataggaacac ttttacactg ttcgtgggac tgtaaactag   18240
ttcaaccatt gtggaagtca gtgtggcgat tcctcaggga tctagaactg gaaataccat   18300
ttgacccagc catcccatta ctaggtatat acccaaagga ttataaatca tgctgctata   18360
aggacacatg cacacgtatg tttattgtgg cactgttcac aatagcaaag acttggaacc   18420
aacccaaatg aacccttctt tttgcttgcg ttgttgaaag aaggcaagtc tatggatagg   18480
aatgagtgag gcacagctcc ctgaggatgc catatcttgc ccgtttcttg tgtattaagt   18540
gacatcacgt gttaccaaac taaaccggct gcatttgcct gcgcacaaca taaaaccaaa   18600
cacccaagca ttggattttt gtagcaagaa agatgtattg ccaagcagcc ttgcaagggg   18660
acagaagacg ggctcaaatc tgtctcccaa tacttgcttc gcagcagtag atttaaggga   18720
gagattttgg aagtggagtt tcgggctgga cggtgattgg ctgaaacgaa gaagtgttta   18780
gaaaatctct tggtcatgag ctgttgcttc ttcatgctgc ttcaagggtc acatgcagat   18840
tcaggaggtg gtataaaaca agctgtggga atttgggctg tgacatcaaa gggccgctcc   18900
tcgggctagt aagtctatttt tgcacaggct ccagtcagcc atattggttc caacctgttc   18960
cagcaagttg tataagcaga ggggattata gcaaactgtt tccttatcgg ctgccctgca   19020
agacaagctc aagatttctg ttagttacca gtttctttaa ccctgtcggg cacagtttca   19080
catgtaatca gaaaggaact tgcaagacac atacaactga aagaaacttg gtctttggaa   19140
gttgtcagta aggtcacaaa gttgtgatgc tagaagcagc cgtatctgag attatgggaa   19200
agagatgata tattggaaaa acaacagcat cactttaaac attactctaa atcaaggttt   19260
ctcaaccttg gcactattga catttttgggt tagatagttc tttcttgttg ggagactgcc   19320
ctgtacattg tgtaggcagc atctcaggcc tttgtagaaa tgtcagtacc aacccacccc   19380
ctccccactg cacaatcaaa aacgtcaaaa tgtcctttgg gagcagtagt tttgagaaac   19440
attgctttgc agatatatat gtttgtttgt ttgttttgct ttgtgacagg gtcttactct   19500
gttgcccagg cagaagtgca atggtgtgat cccactcact gcaacctctg cctcccaggt   19560
tcaagcgatt ctcatgcctc agcctcccga gtagctggga ttacaggaat gcatccatac   19620
acgcggctaa ttttttgtatt tttaatagag atgggatttc accatgttgg ccaggctggt   19680
ctgaaactcc tggcctcatg tgatccaccc acctcgacct cccaaattgc tgggattaca   19740
agcttaagcc actgcgccca gctgagaaac attgctttaa ataatctgtg gtgaaaggaa   19800
gttcccacca cctgcccact cactcagtac ctctgtcacc aaccctcttc cctgggtgtt   19860
tccaagtaca gagggtggaa agggcttttc cacatttccc ctgtttttggt agtaaacatt   19920 aggaacagcc attggccgtg gctaggctca gccacccaca gatatggaca cagtagtctg   19980
acaagctggg ttgctgggtg ctatcagtcc aggctcaact gcttgcactg acaccatttc   20040
cctataggag gcaggtgaga gccatttctg aggaaagtct ctggagcccc tcttccttcc   20100
actgaaagtt gtgcaaaaag atcaggaaga cagcgcttgg atggaataaa tttcagtgta   20160
tccacttgac acattatagt ggctgtccca aagtttacct tatgccaagt actttccatg   20220
tgccacatca tttaatcctc acaaaaacag gggaaaatat tattgccacc ctacagacat   20280
agagactgag attcaatttta aggagatggt tggtaaggga cagagttggg gttcagatgt   20340
caacagtgaa atgcttaaca aactgtcatg cagcccactc ctggcaactc ttcctgctcc   20400
tctctggcct cactcagcct ctactgttcc aggaagcctc attcatagtc atgtggttgc   20460
agacttccca agctcactgt gttaccaaaa agcaagacct gccttctgct gcatcgcccc   20520
```

```
agctgtcacc caacttggat tcagtcccag cactgacaca tcacaaaatc acaaaagtga   20580
gcaaaccatt acctccctga gtctccttt gtttttatct ataaaactag aaaaatattc   20640
tttccatagg aatgttgttg gaaataataa aacattatat tacaagctct agtcattgtt   20700
gatgtttaac aggtaacagt gataattatt tgtcttctca ttaatgaaga aaaggattat   20760
taatcataga gggtggaagg catctatggg aagtagagat ttgaagatag gctaaaaccc   20820
aagtaaggcc tctagattag ataatagtat tgtatctatt ttaatttcct gctttccatc   20880
actgtgccat ggttatataa gagaagtctt tgtttatagg aaatatacac aagaatttag   20940
aagtaaaggg acattgtgtc tgcaacttac tcttacaggg tgtgtgtgtg tgtgtgtgtg   21000
tgtgtgtgtg agagagagag agagacagag agagagagag acagagagaa agagaatgat   21060
aaagcaaata caggaatcag gatgaagcgt atctgtttgt ttgttttgct ttgtgatagg   21120
gtcttgctct gttgcccagg caggagtgca atggtgtgat cccgctcact gcaacctctg   21180
cctcccaggt tcaagcgatt ctcatgcttg tattgttctt gcacctgttc tgcaagtaca   21240
acattgtggg aatggaaaat gcaggaaatg ggcagtaagg ctatgaacga agcccgcaca   21300
ggagtgtggg tagcagagtt ctctagtcca ggctcccacc tgaggtgctg ggacctagaa   21360
gaaaagcctc tctgcagaca gaactggagt taacgctgtc cacgataaat ggcccaggcc   21420
ctgttaagtt tgccccattg agcaaaacaa gtacccaccc gcctttgcag ccttgcctag   21480
ctcacataag gtgccagccc ttgctgtaca gcagaacctt tggggagctg gacaaaagcc   21540
tatcaaggag cataccccca ggaagcccag tccaggtggg gagcccagcc acacaatggc   21600
ccttgccccc acacctcctc attcagtcag ctaaggccat ggcagctgag ctgcctccac   21660
agctcatata ggaaaagggt gtggaaaggg gccaccaatg tggtcaggcc tccatggcct   21720
gagtaggtca ccaagcctca ggtgcacaga cttgatgtca tcaatcaggg tctgtcagca   21780
cacctagccc tcaggaacac tgctccccac tgcaacccca caccaaggca tcctgggctc   21840
cctctgggtt ctccaggccc cagggaagac agacagagtc tgccaccaaa ggtttgagct   21900
ctgccactgg ctacgaagca ataggggatg tcagagcaag ggaggaacag gacaggagta   21960
tacgtgggca ggaagggatt acagccaagg aagacaggag gcaggtgccc tgattttgag   22020
gctgtgcccc agcagggct tcccagaagc tgtatttgtc ctaagacacc cctctgcagc   22080 tgagggcta gagatggata tgtagctgtg ttaggccatt cttgcattgc tataaagaaa   22140
tacctgagac caggtaattt ataaagaaaa gaggtttcat tggttcacag ttctgctggc   22200
tttgcaagag gcatggtgct ggcatctgct cagcctttga ggaggcctca ggaaacttac   22260
agtcatggcg gaaggcaaag gggaagcagg cacatcacac agtggaagca ggagtgagag   22320
agagagaggc actgggaggt gccacacttt taaacaacca gatctcgtgt gaactcagag   22380
caagagctga ctcatcacca aggggatggc ccaagccatt catgagggat ccaccccat   22440 gactcagaca cctcccacca ggccccacct ccaatattgg ggattacaat tcagatgaga   22500
tttggtgggg acacatatcc aaaccatatc agttatcagt agccatactg gatgaatgcc   22560
aggaacttag aattaggaca catggtcatt taggcaagtg gcttgtcctg tcaatggtac   22620
cctgatagtc gtggggttgc cccgtacaaa aagcgagagg aagtctacag agctgtcaaa   22680 gagggggcagg tggaaaggcc tgcagaggag tccctgctc cacaaccagg cgtgcacctc   22740
ccacatcctc ggggctgtag gccccacatg agagcagaaa gaaggatgca gaggaaggcc   22800
aagaacacaa ggtgtgccct tggaaaggct gggcacacca aacacaacct aataaacaac   22860
agcaatgagc acacagggaa agtactcaca gggaaaccat catgaactag aggctgatcc   22920
```

```
cacaccctgc cacatggggc cccaggcccc agcctatcaa ccagtggtcc ttattgccac    22980
agcgattggt ctttggatag gcacctgatg caagcttcag ccaatcaaca ggccactcag    23040
ctggccatca gtaggccatc caatcagagc aaagcccagg actttcttcg actcttaaga    23100
aaagagaagc aaagtaactg gcacagattg gagaggatca aggaaccccg agctggatac    23160
atacaaactt tggggttaaca tggatgatta aatacatatg tttatgtgaa ccacctccca    23220
aatatgctcc actataatga cacaagacaa agggcagggg gagaccaatt gcaaggtggc    23280
gcaaatgaga gatgctacca agggtggcgg gggagagagg ggagcagttg tcaagttagg    23340
aggcaacagg ctgagggaca gggaccagca gacggggagg gaggggctga agcagaagtg    23400
tccagtgtct ggagggatgg ggccagaaag gcaaggggca tcctgaagaa gctatacctg    23460
gggagggcag ctctctcccc acctgctccc caattcatca gccaggaatg ccccatccac    23520 cccacccag ggaggaggac agaggacttt cgtttgggag cattgaatgg ttcagagatt    23580
ctgcaactct gcggtcccca actaaactgc tcattgtttc aagcagtccc tgttgggtaa    23640 atgtcccca ttgtaaccgg actcggattc caccgcttga agccaaata caagaggaga    23700 ggtttggtgg gaggaaaagt ggttttaact agagccagca aaccaagaag atggtgaatt    23760
gttgttttaa agcattcaat tatctcaaat tttaaaattt atcataggat tctgaaagga    23820
aaacttggta tgggacatac gtgggagcag tgcagggtac agggtctatg tgtcttgatc    23880
caatggctgt cttgagtatc acctatcctg aggtctggtt ggtgttatct ttccttcggc    23940
cagatggtgg tgggtgaatt gtttcgactc ccctaagtt ggaggattcc gcagggttc    24000 cgtgtctggt ttttgtttca agattagccc ctggaattcc caaataagca tagagttaga    24060
taagcgggca tggtgcaaag gagtgtctag tgggaaaggg agagaagcag agtttcaaag    24120
tacatttcaa ggttacattt taagactaaa gaaaaagcct taaaatgcat ttttaaagct    24180
gatttaatgc ttggctacac taggctgtgg ccagtgtgca gtgtggctgc tcttggatca    24240
ggtgatgttt catcagctgt gtccagggag ggcagggcca tgtggcagaa cctgggacct    24300
ctgtgtgagg gactaccttg gccctgtcc ttagcaggaa gctatggtaa ggaaccctta    24360
gggagacatt aaattgggga gaccgtccct gccaatcctt taacctcccc agcctcagcg    24420
acctcagttg gaaagtggtg gtaataatac taccactgac caggtgtggt ggccagacat    24480
tccacacttt ggcttcagcc gctccctccc cactctactg taatcccagc actttgggag    24540
gaagaggtag gcggaacctg aggtctggag ttgagaccag cctggtcaac atggtgaaac    24600
cccatatcta ctaaaaagaa agtacaaaaa attagccagg tgcagtggca cacgtgtgtg    24660
gtcccagcta ctcgtgggtc tgaggcatga aaattgtttg agcctgggag gcagaggttc    24720
cattgagtgg agatcgagcc actgcactcc agcctgggtg atagaacgag attctgtctc    24780
aaaaaaataa aaataaaata ataataataa taccactgcc tgccacacta agattgtctg    24840
attagatgac agaatgaatg caaaagtact ttgtgaatca taaatgtttt catcaatatt    24900
agttataatg acaattgctc cttctcctaa taaatgtatt gcctttcttt aggaataaat    24960
ataacaagaa atgtgtaaga tatatatgag aaaaataata aaattcacct gaaggacata    25020
aaagaagacc aaaataaatg aaacaacaca tacttctaga tgagaaaact caatattata    25080
aagaggttag ttctctaaaa tgaatcccta aacccacaaa gtcaatgtat ttccaatgaa    25140
attgtcaaca gcattatttt ccgaagtggg atgagtagtg ctaagattta taagaaagcc    25200
aacattccag agcagtgggg aagggattgc ttcaccacca aatagccata ttagagattc    25260
ccttgcacca tacccaaacc accatctccc aggacccggg agagcagaaa agaggaatga    25320
```

```
gaagaaaggc gaggatgtga ggtgtgccct cataatggcg gtgcacgcag cacaagcaat    25380
tgcagaaaga ctaaagtact gaacaaatag aaaacttgga aaaatattag aaggaaatgt    25440
gggagaacat ttttgcaatt tggggattgg aaacggtttt cttaacaaga tataaaaacc    25500
ccaaaacaag aaaacaaagg ttgaaattca taaaaactag atacttctgt atgatgaaag    25560
acacgattaa tcaagttgtt aagtttagca atagactagg ggagatatca tagtatattt    25620
aacagacaaa ggattaatag atactacaga tgaaatataa aatagtttct ccaagtccat    25680
aggcagaaga taatccaata gcaacatagt taagtaatgt aaacaaatca tccttagaag    25740
aagaaatgca atcaccaaga aacacatgaa aaggtgtcca gcattttgca attcaagcaa    25800
caatgaggtg acagatcggc aaaaaactca taaagattta tcatctgaag gattggccaa    25860
gataaagcca aacttctcgt gttggcagaa gaaactggtg aagccatgtg aagaggccac    25920
gtggtcctgc ctaccaagat gtaaaatgtg tacagcattt gaactagcaa ttcagcctcc    25980
aggagccatc cagaagaaac actgacacac acttagactc cggtgaaatt caaggacttc    26040
tgccacagcc tgcttcgtaa tagtgaaaat ctgaaactgc ctcaatgacc gtcaatagga    26100
agttgatttt aaagtgttac agcacatctg tctggagaga tcgcactggc cactcctcct    26160 cacccctct gctggacctc tgagcgtagg tggcctggag ctgggtcctg agccctcttt     26220
ggtctatacc gacactaccc aatatggtag ccaccagtca cgctggacac ttgaaaagtg    26280
gccgatcctg actgagaagg gccacgagtg ggaaaaacac accagacctc agtgacttag    26340
gcagaagtat gttttgttcc agactattga ctgagcccgc agctgagttg gctccagcac    26400
cctggccccc tgctccatcc actcactggg actccccact gcacagggca acctctccag    26460
gggcacttgg gctgcgaagg ggagagtggg tggcatccca ggctgaagct tcctgagcag    26520
ggccagagga ggagccagtc cctgtgggcc tctgttctga cagtgtcaac ctcagccagg    26580
cttgtgtggg ccaggtgtac tgttctggtt cagatttcaa ggagatagtc agggcaggcc    26640
gcgccaaagc cctccgatgg gctcccctac tgcctggcag acctgtccag ctttggactc    26700
tggccctgcg acctggaagt caggctgcca agaggtccag gcagtggcct ccactgtgga    26760
gggtctctgg agagtttaca gccctagata gggggggttag ggatgtgaga tggtcccagg    26820
ggcctgctcc tgagccacgc caagctgcct gctcccttc ctctgcttcc agactcacgg     26880
gatcctctgc tcatcagaac aggagtgtgg gagaccctga cactgcccc caggatctga    26940 acaggtggca aaggcttaac aggctagcgg tcactgtagt gacaaggcga ttgagtggtc    27000
accatggtga tggggatgga ggctctttgc caccagtccc agttttatgc atggcagctc    27060
taatgacagg atggtcagcc ctgctgaggc cactcctggt caccatgaca accacaggcc    27120
ctctcaggag cacagtaagc cctggcagga gaatccccca ctccacacct ggctggagca    27180
ggaaatgccg agcggcgcct gagccccagg gaagcaggct aggatgtgag agacacagtc    27240
acctgcagcc taattactca aaagctgtcc ccaggtcaca gaagggagag gacatttccc    27300
actgaatctg tctgaaggac actaagcccc acagctcaac acaaccagga gagaaagcgc    27360
tgaggacgcc acccaagcgc ccagcaatgg ccctgcctgg agaacatcca ggctcagtga    27420
ggaagggtcc agaagggaat gcttgccgac tcgttggaga acaatgaaaa ggaggaaact    27480
gtgactgaac ctcaaacccc aaaccagccc gaggagaacc acattctccc agggacccag    27540
ggcgggccgt gacccctgcg gcggagaagc cttggatatt tccacttcag aagcctactg    27600
gggaaggctg aggggtccca gctccccacg ctggctgctg tgcagatgct ggacgacaga    27660
gccaggatgg aggccgccaa gaaggagaag gtatctcgcc ctccattggg cattctggga    27720
```

```
gtgtttgctt gcctgtcccc aacattccat ggtttgtttg agcctcagaa tctgatttta   27780
tgcacaggct ctttgagaag ggtcttgcca ggggtgcctt ctggggcagg aaggcccta    27840 ctgcctggca gacccatcca gctttggact ctggtcctgc gacccggaag tcaggctgcc   27900
aagaggtcca ggcagtggcc tccactgggg agggctctg gagagtttag agccctagat    27960 gtggggtta gggacatgag gtcttgtgga caaagcccac tacctgattt tgagacaaca    28020
ctcactagac atggtgacaa gtcaaagatg ccttgcctcc taccaggaat cacttcgcag   28080
ggagcccgag ggctgctgtg gcctgctgag gagtgcaggg cagttacttt ttccaaaaac   28140
aaagagaaat ccaggcatgc tctgagccag ccctgagccc agcagtgagc aaggagagag   28200
ctggagacag gggactttgc tgtgaaacac tgggggaat gtgcctgcat caccccagct    28260
gggggcccag gcagagtggg ggagaagggg taagtgggca gagccagtca ctttgggcat   28320
gcttccctct cgcctctgtg tgaaatgacc aggtcagcat aaaccccggg ctggctgtgc   28380
ttctggcaga gctaatgatg ttaggaggaa acaaccaac ccaagtgaga gggtgcgcag    28440
ccagacagct ggaccggccg aggccccaac caagtcccag atctgcctgt cactggtgct   28500
atggcagcaa tttggatgag aaatcctgcc caaagggccc cttcaggcca cccggggaga   28560
aggaagcggc tgtcttggc atgaccagaa agatggctcg gagctaggga gaggtggaca    28620
tgtgggctgt ggagatctgg cacttcccc aaacaaggag agaaagcata gtgtgcctat    28680
gtgtgaatgt gctatgtgtg catgtttgtg cctgtgcata cctgcatgtg tacatgcatg   28740
tgcacatatg tgtgcacagg gaatcacttt aataaaggcc acagcagagc tgtccctgag   28800
ccccttgcat tcacagtggc atgtgagtga accaccttct taggctgggc atccagtctc   28860
agactctggg gctgcccatg ccccatcctt tatctgctcc acgtgtgagg ggttgctggt   28920
cctgaccagg gccagctgtg aaccccagaa tcctgggaag tcactgacat tcttgtcagg   28980
gccaagagtg gagcaaggca atgcctcggg cacaaacttt aagggtcac cagaaacatc    29040 aatcatcaag atatatgcta ttttaaataa tcaaaatgaa tgcaaaaaaa atttatgatg   29100
gacaacatac caaattctaa acaaaggcag gatgagtatc actggcttct gcacttttct   29160
ccacccagtc tacccctctt ctagtgcctg gatcgcaggg tgccaaggcc tggatgaggg   29220
aagcgtggag ctgcaatggc cactcctgtc tgcctgttct ggctgcacag aggactcagt   29280
ccttgtcttg ggggaaccta tcttggtttt agggtcatcc taaggatctg atgttttcca   29340
agtgagctgg ctgtccaggc ccacccaggt tcagtccagt cctgtgtctc tgggaagtgc   29400
tgcccctacc ccaagccagt gtttgacctt ggagcaatga gcaatgccct ccttccactt   29460
tcaaagttgt ccccaagacg tcagctgtgg ttgtctctgt gcagacaccg aggaggaact   29520
gtcttctttc tccttttggt tgctttggag gaaagtaaag tgttgctggt ttccctcttt   29580
ctacttcttt gattgagagc agccgtcttg ccggtaccaa ccttccagat cttacctgtg   29640
gttgcaggag cctgtggcct cagtcctgtg cccagtgact tctccatgtg gatgtcagct   29700
ccttaggggc aagcctgatt ccactgacac tactcccacc cctcataagc cccttcttac   29760
cagctgcagt tgcctggtac cccaccatcg ctgactcatt cctttggcat caaggttcat   29820
cccttactgg gccaccactt ctgggtggcc tgaaataggg ccctgggcat ccctcttggg   29880 gacctttgg tctatatttt cactctcacc tcactaagga cagatgagta aatctggtta   29940
actttgcctg atagatttgg tgacctttt tcaggaagga gcctggaaag atgagattca    30000
ggtgtattgg tcagcttaga ctgccataag agaataccat ccactgatgg cttagaaaca   30060
acagaaatct atttctcact attctagagg ctggacgtcc aagatcagat gccagcatgg   30120
```

-continued

```
tcaggttgca gggagggctc tcttcctgac ttgcagaccg ccaccttctt gctgtgtcct    30180
cacatcgtgg agagagagtg aaaacaagct ctctggtgtc tcttcttata agaatgctaa    30240
tcctatgatg ggggctcccc ctccttacct catctaaacc taattatctc ccaaaggtct    30300
catctccaga taccatcaca ctggggttag ggctttgaca tatgaatctg gggggacaca    30360
attcaatctg taacaccagg agggcatgcc gggaggaact gaccttcctc cctccagctg    30420
ccctggacac ctttgcccca ttgaaggagc aggctcagaa gtggaatgag gatgaataa    30480 ggtgcactcc atcatgctta cccacatccc tggcaggaat tgtcctgggc cccagcagga    30540
gagatgcccc cccatactgc catggcacct gctctgagac aggtgtgcag agtgcaaagc    30600
tccaggtggc ccccaagcag gtgtgctggg aggaggggcc cgtgtgggag gagcaggcag    30660
cgccaaggcc tagcggagca gtgacaggtc cctgacttca gggaatgggc acgctgtggg    30720
caggcagctg gtgtgggggt gagggctggg gctgcatctg tgggaccagg gctgggccat    30780
ccatcatatg ccgtgtcaca accccagtgc ccctgctgta gccaggacag gaggctgggc    30840
caggctggga ggtgacaaga gtgggggctg tccccaggag aagcactctg ctgcctgtgc    30900
ccaggcctct ggggatgagg accccctcaga aggagtagct atgtctagga agccccaggg    30960
caggagcaag ccaaggggga catcattagt gagatccagg ggatcagtgg gccacagaag    31020
ccccagcgtg agccctctg actgatgcag ctaggcccac acctgcacct gcccacagca    31080 agaccccag gaggagaggg gacagatgga gagaggcaca aagtgcccct ggcctctgcc    31140
ttgaagccac cccaaggcaa gagagatttg agccctgtt tagtgacctc caggggaaca    31200
ttctggccca tctgatgtgg gaagcccctt gtggagtctg tcattcctca gctgagccag    31260
gcctttggag gcagcccagg catgtcccct gtgtgctcct atccctgtgt tgggacacct    31320
ggcccagccc ctccttctgc cttctcttc ccttccttc tcaggagtgg acacttcctc    31380
ctttagcccc ctcacagctg tgtgaacttc tctgtatctc tctctttctg tctcttttctc    31440 cccctctctc tctgtctcat tgtctctctg tgtgtctgtc tgtagtattc tctctctgtc    31500
tctgtcactc tgtctctctc tctctctgtg tctacctttc tgtatttcgc tttgtttctt    31560
tttctctgtg tgtgtgtgtg tgtatctgtt tttctcactc tctctctgtg tctatcttttc    31620 tgtatttcgc tttgtttctt ttctctgtgt gtgtgtgtg tatatctgtt tttctcactc    31680
tctcaatctc tctctctctt tctgtctctc ttttgctggc ctgagcaaag agggagcccc    31740
atcctgatgc tacataaccg tgaaccagca cagacagaat tgtaggaaag tcctgcaagt    31800
agaaggatag aaggatgagg gaagaaacgc catgtgagtc atgacagatc cctttccagg    31860
agccactgac tcaccctgcc tcctgccctc ccactgtgac actattactc acagacaggc    31920
ccggattaaa cctatgttcc aggtgccctg tggttccac agtgtggctc cctgggtctg    31980
gcctcaggct ccacaggtgc ccagccctgc caaagtctcc agagcagctg tccagctggg    32040
gagctgcggg gccccttcac agagcgcatg ggaagaagtt ccatcctaca cattacatcg    32100
agagggacgt gcctgagaag gggagctgga gcccgtgcag cccctgctt gcgtgcagaa    32160 catagtgtac cctgagcatg ccatgaaaaa cacaaacgca caaagttgta aagaaaaaag    32220
aaatgacagg tggctgtaaa atcagttata gcccacgaga ggcccactaa tgagtggtga    32280
tttcagctga ttacaaagaa atgatggtgt ttctgtaatg aactaaacat gcactcgtgc    32340
gtgcacacac gcgcacgtat agtcacataa ctgaccagcc ctatgcatca cttgttaatt    32400
acttagtaac tgtaacaata atagtttcca ataagtgagc cttagtctct gcgcaagggt    32460
cagtttattg agcacacggg ggccttgcag tgggggcagg tgatctgctc ctgggagccg    32520
```

```
ccagcctctc ctctcctgct cttcatcttc ctccgtggtg ggaaattgtc tcactgcttc   32580
tacacctgag gctgaacatc tcccttattt tcagtctgaa acacatgtaa aaatatactg   32640
gaatgaatta aggttgcaat tattgatatc aggcagtgag tacatcaggg tttattatac   32700
tatctccttt acttacttcg aagttctcta ttaccaaaaa attaaaaact ataaaagaaa   32760
gaaaaaggaa atgaggctag attcaacaca gattactctt accaaaccct tcgtagtccc   32820
aggagtcccc taacacaagc acttgtgacc tggagtgata ttcacagcat tccttacctg   32880
gcaatacctg agtattagcc cccccagtgg gatctttgtt gtagacaacc agcaactatc   32940
agcccagcca ataaacaagt aggaaagggg agtgctggag aggccaagaa gtgggatttt   33000
ccatgctcct gggctgtgat ccagagggca cggctgtgag gctgatctca atgaacactc   33060
tgtcttggaa gtacagggat cctctgctac ctgaaaacgt tctgagtatt cactttcatg   33120
gattgcaaag tcatttaccc aaaattcact ctccaaatga aaagtgagta tgatgaatca   33180
gtattcaagt tccacctggg tcctgggaga gggcatggac atcatatccc agctgttccg   33240
acaggaggac ccaatctgag tctcactgcc tgcctgcatc gtttgtctgc tgccagcctg   33300
cacagtagga agggaaaaca tgatttgtat ctgttttagg tcaggttccc aagaagtaga   33360
gcctgagatt ggaattcttg gaaaatggtg tttgcgggag cgctgtcagc agaagctata   33420
aggaagttgg ggggacagaa aacgagaggt aagaagccag tcaaaaaggc aggtccagct   33480
taagtccgcc tcagtctggt tccacaaggg ctctgatgca tgaagaatat cacagggttg   33540
tccctcctgg gagaggggcc agcctattgt acctgtatca aagccaccag ctgagggcca   33600
gtggggaggg aagatcttcc aggcatttcc aggaaactct caggagaagg gtgtagctgt   33660
gagcagtctg cagctgctgc tcactgcggc taaaggctgg gtgtgcaggc cagtcagcca   33720
gtgaggtgcc aacagcaggc actacagtcc accccttgac tgctcagacc tactgctttc   33780
cactttaagc tctctccatc caggcacagc ttcaggaaaa acttacaatt ggagaaacag   33840
agggatgaac tacaatgccc acttctgcat gtgattgtaa actgtcact gatactcacc   33900 atcatgcccc atccccacca tccattctag tgtccccttc cccttggcta acactgctgg   33960
tctaggtgac ttccctagag caggagccaa acccttatcc ctgaggcatc tgaatcctgg   34020
attcctttat caggctattg ttgttgtaag ttgtccattc ccaattacaa ctggacatga   34080
gactaccaag aaacaccctg gcaaatcatc tgagtgcaag ccatattctt cctgctccat   34140
tatgtagcgg tagtcctacc tcctaatgac aagggtaaat tgccacattt tgctccttgt   34200
gccaggatgg taatacctttt ctctacctgc ttggctactg gcacaaggaa gcacagcatg   34260
accaggaggc aattgtagct gtacatttag tgaatgtgtt aatgtatcac ctggtggaag   34320 gacccctct gagaaccagg acttctagac ccacaaaacc taaagttgtg aatggcggaa   34380
gcacaaattt cccaagtgga tcatggagag tgatgaagag ttcttggttc ccaaacccac   34440
atattttacc tttcaggaac atggcctcat cccatagcca ttagagtgca tattgcattc   34500
tggaggagac tgggccctcc tcatgggtgt catcttcaag atgacagctc cactgtgcct   34560
ccaagaggat gctccaccac cctatctgtg attccttggt tagcaggaca ggctgctgca   34620
ctgagggtag gaaaggcaag tccattgatg gctggaatac atgtcaatcc aagtcaagag   34680
aaaatgccgc cctttccagg ttggaagggg cccgatttag ccaacttgtc acccagtagt   34740
ggctggttgg tctcctccag gagcagtgtt ataccaggaa ttcagcacca gtcgctattg   34800
ctggcagttc ttacattcaa cagcagcaaa actaggtcag ccttgatgag agggaatgta   34860
tgcttctggg cacaggcatg gcttccttct ctgactccat gactatctat ttctgagtgc   34920
```

| | | | | | |
|---|---|---|---|---|---|
| atggtggccg | acattcagct | gcctgcccat | cctatccact | tggttattat | tgcctcttcc | 34980 |
| acaagaagtg | gtttctggct | gtcattaatg | tctcatactt | tgtgcccact | cacacaggtt | 35040 |
| tagctctaca | acttttcccc | atgccaccac | ttttccacaa | tcttctaatg | ttgctccttc | 35100 |
| caagctactg | aagaacgagc | taagctattc | accaatgtcc | atgagtctat | atttaccttg | 35160 |
| ggccacatct | ctctccacac | aaagtgaata | agcaggtgca | ccctccaaaa | ctctactaag | 35220 |
| aggatttctt | ctccccagtg | tctttcaggg | ccaccttgag | tggggctgaa | gtacagcaga | 35280 |
| agtccatttc | cagcttgcat | caacattcca | aactaaccta | tccatgatca | atgcatagat | 35340 |
| gggtttttcc | ctcctccagc | agctagacaa | aagacacccc | ccaccaggag | gccatatttg | 35400 |
| catgtgggtg | aaagagaggc | acaggggcca | atattcgtgc | aacagtggta | gatggcaggt | 35460 |
| gggtctgggc | cacctgtccc | tgcagcttat | ctgtgccatc | tggacctgct | caagcctgat | 35520 |
| tccagatata | ccatttccat | cttatgatgg | atggcttatg | acctagtggg | tctgacagca | 35580 |
| ccaaactcat | aatgggcagt | tatgccaca | tggtcactta | atgtcctatg | gtcagacact | 35640 |
| ctgctgagtg | gcatgccagg | aaatgcttta | caagtggtgt | ttggttctct | gctgcagatg | 35700 |
| gcatgacctt | ggtccggagc | cctaggggtt | tggacagtga | ctcctgttgg | ggcctaatct | 35760 |
| cacattccat | gcagagtatc | atcagatttg | ccaatcacat | agcctaaggg | tcaggactga | 35820 |
| tccaaccagt | ttttgcagag | atcaaactgg | agaatgaaag | gttgatatga | tgtgaccatc | 35880 |
| atatcacgtt | tttctctctt | gaaaagtatg | cagatgtctg | aaagagacaa | gtgccccagg | 35940 |
| agaaaatgca | tgccttcctc | aggatcggcc | cccacctccc | ctcctggcca | caaggagggt | 36000 |
| caaatctcag | catggcccaa | cttggacctg | tcaaggaaga | agaaaaaaat | tgtatgccaa | 36060 |
| aggaactcag | tctttggcta | acaagtacta | gacatccttt | aagtctttga | gaatggtaat | 36120 |
| aatttctgcc | atccctccag | atttgtgttt | ttctgttttg | gctgggtggg | aatgcagcat | 36180 |
| tttcactttg | cctttgttat | tacaaatgtt | gcttattcta | taaatcaagg | aaccattgta | 36240 |
| agggctcttc | tgatggttaa | gtatatccat | tccaatgatt | tattcgggat | ccaaggaaat | 36300 |
| gatttctggg | tgaatacaca | gaactagtgg | atccaatttg | agacatacct | gggccagaac | 36360 |
| tatatttgtc | gtcttacccc | aataagcctg | cactctacta | ggacagccat | gacagcactt | 36420 |
| tgggaccccta | gatataagtg | tgaattgctg | gctgggcatg | gtggctcacg | cctgtaatcc | 36480 |
| cagcattttg | ggaggctgag | gcaggtagat | cacctgaggt | caggagttga | agaccagcct | 36540 |
| ggccaacacg | gtgaaacccc | atctctacta | aaaaatacaa | aaattagctg | ggcgtggtgg | 36600 |
| tgggtgcctg | taatcccagc | tactcggag | gctgaggcag | ggagaattgc | ttgaacccag | 36660 |
| gaggcggagg | ttgcagtgag | ccaaaatcac | accactgcac | tccagcctgg | gtgacagagc | 36720 |
| gagattccat | ctcaaaaaaa | gaaaaaaaa | agtgtgaatt | gctatgaaat | cactatcaaa | 36780 |
| agatctgagt | gttacccctta | ctcagtgtgg | tcgaatataa | atagccatag | gttcctgtta | 36840 |
| tacacacttg | ctgtggtgct | acagagtctt | tcctcatggg | aacccagtcc | ctctttcagt | 36900 |
| caatgggttc | tggttcgaga | actggctgag | gtttggaaac | tgtgcctttc | catcataact | 36960 |
| ttccactggg | gtgactgacc | ttggccttct | gttcatcctt | tctagcccct | aagaatccaa | 37020 |
| cactctatta | gccttctcct | tagacccta | taagctaatc | ccttctagtt | gttagtctga | 37080 |
| ccttggtgcc | caatatgata | attattccca | ctttgcttct | gatatgcttc | taagtgctgc | 37140 |
| ccctggtctc | tgcccttaag | tgatctatca | tccccactgc | cattagggg | agaagctctg | 37200 |
| aaaaagagtt | gtctcccatc | aactctggtc | tacaaaggac | agccctactg | agcctcagcc | 37260 |
| atgtgcccga | caccagcaga | ttctttacag | cctgggaagc | agagtgtctt | ccctgccttt | 37320 |

-continued

```
ccagggaaca tagccagctt acaggctttt tgatcttata gagtaggtca gttatatttt    37380
gccccatttc ttttatcctt ttgatcactt cctcttggcc caccatgtaa actcaagcat    37440
ccctgcttca tttaatcgag ctgttgcttt ttctaagcta ccaagagcaa ccccagcaat    37500
atatcagagc cctctcttgg gacccttgct agggtgttaa atcctgcatc ataggagaat    37560
gcccccacat cagcaaagtc cccttatcct cttgatatcc cacctgcccc agtccagcac    37620
cttcaggatc tggtctcaat cacaggatcc agcacctttg ggactgttgc aagcataaga    37680
tccagcactt ttgggatcta gtctcccact tcctgctagt acttgttagc caaagactga    37740
gttcctttgg catacaattt ttttcttctt ccttgacagg tccaagttgg gccatgctga    37800
gatttgaccc tccttgtggc caggagggga ggtagggggcc gatcctgagg aaggcactca    37860
ttttctcctg gggcacttgt ctctttcaga catctgcata cttttcaaga gagaaaaggc    37920
ctccttctca cagcaagact acttctgtag atgcaggtgg ctcgtgggaa tctggcaatt    37980
caaaattctc aagtgtactc actagcacat tagaaaacca gtagtacaca tctctttcca    38040
aatcttcatt cagtgacact atgtcagtag ctggaaatgg gccatggtgg gtgtatttaa    38100
accatgaaaa tcagaaaatg ctacaaacca gggcatcccg catctctaga cagcagattg    38160
ttggccattt cccagcatac cattgtgtat actccttccc atcagggccg tggcttgcct    38220
tggtggagga ctcagccctt gctgaagttc tgctactgct cttacaattg agtcctatgc    38280
ctggtctcca gctctgcctg cctcactaca ggagacaagc atctctttga acactgccga    38340
gaagaccctc tggctctcag gcttggcttt aaatcgatag acctgagcct gccatttcct    38400
cttttccatg catcactcca ctgatccaca ggtctcagtg gcatagtcct tcgggttagc    38460
atctccccca caccctcggt gccagagaca ctgagtaaga aagtacctcc ctgtctaccc    38520
ccatccccgc tccccacagg cagggccttg gcgatccact gctgcaatgt gccagagact    38580
gtcagtactc ctaccaccag tgaggtggca accagctggg aagtgatcca actccagagt    38640
cccgccctca taggctgatt tctaggacca cccctggtat actgtgttag gttcttgaag    38700
cagagcctga gataaggatt ctggcacctg tgattgagtg ggagggtgct ctcaggatga    38760 gatgggtag aaataggcaa aggtacagat tcagcagcag ttgagcctca gtctgaccca    38820
gcagggagct ctcaaatgtg aatgacatca cagagttgtc cctctgaggc aggggccagc    38880 cttttgtgctc ctacatgagt cagtcactgg ctggaggccc ctggggaaag gctagggctg    38940
ccagctttag caaataaaaa attagggcac tcagttaaat tgaatttcag ataaacaaca    39000
```

<210> SEQ ID NO 6
<211> LENGTH: 45980
<212> TYPE: DNA
<213> ORGANISM: Homo sapiens

<400> SEQUENCE: 6

```
actagcacat tagaaaacca gtagtacaca tctctttcca aatcttcatt cagtgacact      60
atgtcagtag ctggaaatgg gccatggtgg gtgtatttaa accatgaaaa tcagaaaatg     120
ctacaaacca gggcatcccg catctctaga cagcagattg ttggccattt cccagcatac     180
cattgtgtat actccttccc atcagggccg tggcttgcct tggtggagga ctcagccctt     240
gctgaagttc tgctactgct cttacaattg agtcctatgc ctggtctcca gctctgcctg     300
cctcactaca ggagacaagc atctctttga acactgccga gaagaccctc tggctctcag     360
gcttggcttt aaatcgatag acctgagcct gccatttcct cttttccatg catcactcca     420
ctgatccaca ggtctcagtg gcatagtcct tcgggttagc atctccccca caccctcggt     480
```

```
gccagagaca ctgagtaaga aagtacctcc ctgtctaccc ccatcccgc tccccacagg    540 cagggccttg gcgatccact gctgcaatgt gccagagact gtcagtactc ctaccaccag    600
tgaggtggca accagctggg aagtgatcca actccagagt cccgccctca taggctgatt    660
tctaggacca cccctggtat actgtgttag gttcttgaag cagagcctga gataaggatt    720
ctggcacctg tgattgagtg ggagggtgct ctcaggatga gatggggtag aaataggcaa    780
aggtacagat tcagcagcag ttgagcctca gtctgaccca gcaggagct ctcaaatgtg     840 aatgacatca cagagttgtc cctctgaggc aggggccagc cttttgtgctc ctacatgagt   900 cagtcactgg ctggaggccc ctggggaaag gctagggctg ccagctttag caaataaaaa    960
attagggcac tcagttaaat tgaatttcag ataaacaaca aattattttt tagtatatgt   1020
cccaaattgt gcataacata atgtgttttc tccgccagcc ctgggaaggg cgtaacttcc   1080
caggtatttc taggtgaagt aactttgtag atcaggagta agtcccagga aagaagtcca   1140
gctcttctct tcagccctgg gcagctgggg gtaggcacag gggcccagca ggcacccata   1200
gcatctccta cagcatctga aatgaacagg gtcatcacgt actacataca aatgtaccca   1260
ctgctgagtt cttcagggat tatatcatta ggtacttggt attttaaata cattacatta   1320
tgcagaagtc ctttgtggat tgctatattt ggagagtttt gtgatattgg ggggattaga   1380
tggagttttc agatgggcat catacggttt ttcatttaaa accctagagt attgtaatcc   1440
tagggagtga tcctgcgatt agtaaattag ctctccaata gattttcaat gtggttgcaa   1500
aggacatgca tgtggttcac cctcccagga aatccagaag ggcagcattg gcctgagtgg   1560
cctgagtttg gctggttggg ctggtaatgc tggacaaaga caatgggtgg aatggtttgc   1620
ttccctcagt cctttcagac acagcccagc ccaccacgtc aagccagtgg gtgcatctgc   1680
aaccaatccc catgagaact gcagcctctc agaggtgggc aagttggccc gggtgggtca   1740
ggaggatcag atgttgagga aatctttgga ttggaggcag gcagagcagg gaagcatcgg   1800
gtgattctat gacagaccca gggctccaag ctgcagttca ggaggggcac tggcacggcc   1860
tctgctcaac tccccttga gtgacatcag gtgaagtgcc gacaacacag aaggcagcaa   1920
atgctgccag tcaggtctgc ttcccaggac agccagttgc taacccttct ccagcacagc   1980
actggatttt ggtcacctgg ctgggagctc cacctcccca gctgctgcct cacctgcttt   2040
tccaaacccc accctgtaaa cggtaactac attttgtgcc cactacgcct cgtttccatc   2100 tcttttggagc acctctcacg tggagctgaa cagaacgacc tgttaagccc accgtgtctg   2160
ttagggttgt ctaggctgta tcagatccc aactaaaact ggattcacca acaggtattg    2220
tcaaagcaca taagaaagag tccagaggca ggcagctctc agcctggtgt caggctctgg   2280
gtcagctttc cagattctct taaccttccc cacatctgcc agatgccgcc acaggcacag   2340
gaggtacaaa caaacccaaa aatgttctgg aaacaagaag ggaagggat ccccaccata    2400 tctccccaga ggccttcctt ctcacatctc actgtactga agccagctct agcagaagac   2460
agcagggtga atttgtccag ggtattcagc ccccagtgct gggtccatta ctacttgacc   2520
cctgaataaa acagaggttc catgagcaag aaggaagggg aactgatgt tagagggcaa    2580 gaatgtatcc atcccacccc taggagcacg catggacaac tgccccattt ttgctcctat   2640
tgcagcccag ggctagccc agagaccttg ccagtgctga gtcacaagat gctgggaaag    2700
tgagaccaga gcctggtctt ggggaacagc tcaaggccgc attggtctgc aggtcataga   2760
gcagctgctg agcagtgaga gcccacgatg ggccaggccc tggtcttgg agacctgaat    2820 gagatagact gggttcctgt tctcctgggc attgcctctt agagggcaaa gacaattaac   2880
```

```
aataaacaaa tagaacatga agtgttttcc gatagtgact gatatacttt ggatatttgt   2940
cctctccaaa tctcatgttg aaatgtaatt ccttatgttg gaggtggggc ctggaaggag   3000
gtgtctgggt catgggggca gatccctcat gaatggttta gtgccatccc cttggtgatg   3060
agtgagttca cgtgagagct ggttgtttga aagagcctgg cccctctca ttctcctgct    3120 cccactcttg catgagacac ctgctccccc ttctccttct gccatgattt taagattcca   3180
gggacttcac aagaagcaaa tgctaacgcc atgcttcttg ttctgtctgc aaaactgtaa   3240
gccaattaaa cctcttttct ttgtaattta ccagtcttg ggtatttctt tataacagca    3300
caagaacagc taatacagt gatgctctcc aagtgacctt tgggctgaga cctgaagaag    3360
aaggggaagc agttaggtct gatagctcat gcctgtaatc ccagctcttt aggaggctga   3420 agtggggagga ctgcttgagc ctaggagttg aagaccagct tggaaaacat agcaagaccc  3480
tggctctaca aaatatttt ttaattggcc aggtgtggtg gtgcacacct gtagtcccac    3540
ctacttggaa ggctgaggca ggagcatctc ttgagcccag gaggttgaga ctgcagtgag   3600
tcatgttcac accactgcac tccagcttgg gtgacagagc aagacctgtc tcgaaaaga   3660 agaaagaaga aagtaggaag aagaagaaga agaagaagaa gaagaagaag aagaagaaga   3720
agaagaagaa gaaggaagaag aagaggaaga ggaacaagaa caagaagaag aacaagaaga  3780
acaagaagaa gaacaaggag aacaagaaga agaataagaa gaagaaggag aagaagaaga   3840
aggagaggaa gaagaagaag aggagagga ggaagaggag gaggaggaag atgaggagga    3900
ggaagcagaa gcagaagaaa aagaagaaa agaaagaaag agaaagaaag aaaagggaag    3960
gagggaagga aggaaggaag gaaaagggga aggaagggga aggagaggga gagggagaag   4020
gaagaacaaa gaagaaagaa ggagaagcag aggcttgtgc tggatagcct tgcttttgcc   4080
aatgaccttg ctgattttca gggggtcctg gtgtcttagt ccatttgtgt tgctgtaaag   4140
gcatacctga ggctgataa tttacagaga aaagaggttt atttggctga gagttctgca   4200
ggctctacaa gaagcatggc accaatgcct acttctgatg agggcctcag tctgcttcca   4260
ctcatggcag aaggtgaagc agagcctgca tgtgcagata tcacatggtg agagaggaag   4320
cacgaggggg cagggaggtg ccagcctctt cctaatagta agctgtcttg agaactaata   4380
gagtaagaaa taactcacac cctgccccca aggaagggca ttaatctatt catgaagtat   4440
ctgcccccat gacccaaaca tctcccatta ggcccccac ctccaacatt gaggatcaaa    4500
tttcaacatg aggttccggt gggcaaacat ccagctataa tactgggcaa tgctgaccag   4560
actcttcccc tctcaggccc agagctcctt ggccctgtaa caacagaaaa ttgcgtttga   4620
gtgtcaagat ttttccttta gtccccatgc agctccttag aatgaggtgg catcttctcc   4680
cttttcatag gtgaagaaac agaagctctg gaggaacgaa tcattcatcc aaggtcaggt   4740
agctagtaag cgtcccacca gctccccaga tctcctgttt cctgtcccaa gtcccactga   4800
gtgagctgga acaatggctt cactggcacc tgccgggaat ggtggcaggt gcctataatc   4860
ccagctactc gggaggctga ggcatgagaa tcacttgaac ccgggaggca gaggttgcag   4920
cgagccaaga tcacaccact gcactccagc ctggataaca aacggagatt ccatttaaaa   4980
aaattaacat ataatataca tacagtaaca ttcacttttt aagtgtacag tttgatgagt   5040
tttatcaaat gtatatggtt atataaccac catcaccatt aaggcagaat cttcccatca   5100
ctcaaataat tccctcagcc ccacctcttg ctgtcaatca cttctcccac cctagccact   5160
ggaaatcatt catctgtttt ctgtccccctt ggttttgcct tttctagaat gttctataca   5220
tgagaccact gagaatatag tcttctgtgt ctggcttctt tcacttaaca taatgcctag   5280
```

```
ctcagcagtg tgtcaatcct ccctcccttg ccattgctga gcagtgagta ttccactgta   5340
tggctgtgct acggtgtgtt catccattta ttcattcacc agctaatggg catttggatt   5400
gtttccaggc tttggctatg atgagtgaag ctgctgtgaa tgttcaagta caagtctttg   5460
tgtagacagg ggttttcaat tggcgggata aatacctagg agtagtatcg tgtggttaag   5520
cgtacgttta aacttagaaa aactgtcaaa ctgttttcca atgtggcctg taccatgttg   5580
catttccatc agcagtgttt gagaattcca attgctccac atcctcctcc cgacacttgg   5640
tttcacccat cttttaaata ttagccactc tggtgactgt gtagtgatat gtcagtgtgg   5700
ttgtaatttg catttctatg attgactaat aataatgttg cagatatttc tgtatgctta   5760
gtgggcattt ttggtgagtt tttaaaaatt gggttgttgt caccgtctta ttgagttgga   5820
agaattcttt atatgttctg gatgtttatt catgtgtgtg tctgctaaga ggtgagactg   5880
gttctaccct ggtcctaaca agcaccctgg gcctgcatcc cttttgtgt ctgtgagctg    5940 ggtctgcagc cctctcctcc cactacctac tgcccagcag tacccctcac ccatcactgt   6000
ggctcctgca atgacatctc agcctgtctc tccctccctc cagctagcca gaggcaggat   6060
ggctcagtga cacagggtgg gccctgaaga cagagtgcca gggtttggac cttgtattag   6120
caagagtcac aagggaaact tactttatct ctccatagct ctgttgtgag gatccaataa   6180
attaatccat agaagagctt aggacagcac ctggcacaaa gtatacatga gctattatga   6240
tgttattctt ccaacccatt gtttctgtgt tgtcataaac atgaatgcag gactcagtgt   6300
cccagctctg tgtccctcgc atacattccc taacagccca caggtcttgc ctgtcaccgc   6360
ctcattcaat aagtgatgac tctgcctctt ccttggctgg ggccttgcat tggacatttc   6420
tgtatccata tttgtttttt aaaaactagc tgttggccgg gcgcggtggc tcacatctct   6480
aatcccagca cttgggaggc agagacaggt ggatcatgag gtcaggagtt caaggccagc   6540
ctggccaaca tggtgaaacc ccatctgtac aaaaaatacg aaaattagct gggcgtggtg   6600
gcatgcacct gtaatcccag ctacttggga ggctgaagca ggagaatcgc ttgaacctgg   6660
gaggcagagg ttgtagtgag ccaatatagc gccactgcac tccagcctgg gcaacacagc   6720
aaaactccat ctcaaaaaaa aaaaaaacaa aaaacaacct agctggactt gacactcttg   6780
ttagaggaag attttttccac atctgttaac ttttcttcta ttgttatcca tctgtgcagg   6840 ttttctgtc ctcctgagtc atttttgataa tttatattat attttgaaaa tcatccattt    6900
cctatagttg tttattagtg tcttctctgt tatatttgat cagattacca aatcttgctc   6960
attgattgcc catttatttt attgtgttta ttttttttgag acagggtctc actcgacagc   7020
ccaggctgaa gtgcagtggt gcaatcatgg ctcactgcag ccttgacctc ctgggctcaa   7080
gcaattctcc cacctcagcc tcctgagtag ctgggacctc aggcacacgc caccacagct   7140
ggctaatatt ttatttattt atttatttat ttattttgt agagatgggg tctcactatg    7200
ttgcccaggc tggtttcaaa ctccttggtt caagtgatcc tcctgcctca gcttcccaaa   7260
gtactgggat tacaggagtg agccaccatg cccagcccct atttacttta tagtaagtgc   7320
cttcatgggc ataaatgttc ctctgagaca gctttggcta ttagccatac ttttaatatt   7380
ttgtacattc atggttattc atttataaat ggtctgtaat gcaatgcaga tttcccctt    7440 ggcccaaatg ccatttacag cagcactttt ctctttctga gcagacagaa tattttggtt   7500
tcccctctgt tgtttatttc tcgtctgcct cgcctcattt gctaggtgtt cccttggtgt   7560
gccttaagta tgagccactc aaatatttgt gtttctctaa acacccctga cactgtcctg   7620
ctggtttctc tatctggaat atccttccct tcttggccag ttccccctag tgcatcaaag   7680
```

```
aaatcctgct cttttgcctt cagaaaacaa aacaaaacga aacctatcag tctccttatg    7740
tccccaaaga catagctttg ctggtatctg gttgtattga gctgttcatt tgtctcttct    7800
gctagatggt aagctccttg gaaactaaaa actaatcact tttctaactt cagactgagc    7860
acaaattagg ttctcaagaa acattgaata atgagtgatc cggtatcccc ttccaacata    7920
tttttggtca ttgataccat cattctgagt agttactagg gaacacttca ctgcagtaac    7980
caatacagca aaacgtgaaa tacagttaca tagtagaatt gtatttcttg cccatataat    8040
agtcaagtgc agttcttcat cagctgggag gttctcctcc acacagtcat ttaggaatcc    8100
agggaacata gcagaggttg ctagctctag acccaaaccc atgtcctctt tgtccacagt    8160
gaggacaatg ccagcaacag ctggccagct gttctgtagt tctcagcctc cctcgcagtg    8220
agatgtctcc atgcaatttc agtggagcaa catataccat ttccatttcc aggtgtaggc    8280
tcctaagaag agggtggctt cttcatgttc tttctcacct ttccgtaggc tagctgcaga    8340
taatgatgag gctttaggga gtgggtggag ccataaagta gaagcctgga ttcctaaatg    8400
acggtgtgaa gtgttcccta atttcacgta attgtttctt aatttcctgt ttgggttatt    8460
tgttgctaag gtataaaaaa accctgattt ttgtgtgttg atatttgtgt gctgcaactt    8520
tgctgaatta gcttattagc tcaatttgat ctcagatatt agctcaaata ttttgggaga    8580
ttatttatgg ttatctacat aagatcatgt catctgaaat aaagatagtt ctatttcctt    8640
ctttctatct tagtccattt gggctgctgt aacaaaatgc cataaattgg aggctgagaa    8700
gtccaagatc aaggcccaag ctaattcact gtctgatgaa ggcctgcttt ctggttcata    8760
catggcacct tctagctgtg tcctcacatg gtggaaaagg caaggtagct ctctgggatt    8820
ccttttttgtt tgtttgtttg ttttgttgtt tttgtttgat ttttttgagac agagtctcac    8880
tctgtcacca ggctggagtg cagtggcaca atctcggctc attgcaacct ctgactccct    8940
ggttcaaacg attctcctgc ctcagcctcc tgagtagctg ggattacagg tacccatcac    9000
catgtccagc tacttttttgt atttttagta gagacagggt ttcaccatgt tggccaggat    9060
ggtctcgatc tcttgacctc gtgatctgcc caccttggcc tcccaaagtg ctgggattac    9120
aggcatgagc caccgtgcct gtcctccggt attctttttta aagggctct ttttctttt    9180
atgtgggctc taccctcatg acctagcacc ttctaaggcc ccacctctta atatcatcac    9240
acagcagatt taatatatga atttttgaggg gacacattct ttccatagca cttttccagta    9300
tggataccct ttatttattt ttcttcccta attgctttgg ttagaaatgt cttccctaat    9360
tgctccacta ctatgttgaa aagaagtggc aaaagtgggg attcttgtct tgctcctctc    9420
ttaggaagaa agtttaagtc ttttgccatt aaatatgacg ttagctatgg ggttttcata    9480
tatgacattt atcatgttga ggaaatttttc ttccttgtttc aatgatgaca gggtgttgag    9540
ttttgtcaga tgcttttttct gcatcaatca atatgaccat gtagtttctt tgttttattc    9600
cattattgta gtacattaca ttaattttttg catgttgaac tattcttgtg ttcctgggat    9660
aaatttcact tggttatggt gtataatcca taaccataac ctgaagatat gctgaagagg    9720
ctaagtgcca tggctcatgc ctgtaattcc aacactttgg gaggctggtg tgggaggatc    9780
acctgaaatc aggagtttta gaagagcctg ggcaagtaaa caagatccca tctctacaaa    9840
aaattgaaaa ttaccgctgg gcatggtggc tcacgcctgt aatcccagca ctttgggtgg    9900
ccgaggcagg cagatcacct gaggtcggga gttctagacc agcctgacca acatagaaaa    9960
accccgtctc tactgaaaat acagaattag ccaggcgtgg tggcacatgc ctgtaatccc    10020
agctactcag gaggctgagg caggaaaatc acttgaacct gggagacgga ggttgcagcg    10080
```

| | | | | | |
|---|---|---|---|---|---|
| agccaagatc | atgccattgc | actccagcct | gggcaacaag | agcaaatctc | cgtctcaaaa | 10140
| aaaaaaaaaa | gaaagaaag | aaagaaagaa | aagaaaagaa | agaaaattag | cttgatgtgg | 10200
| tggttgtgca | cctttagtcc | tagctactca | ggaggctgag | gcaggaggat | tgtttgagcc | 10260
| caggaggttg | aggctgcagt | gagccatgat | tgcaccactg | cactccagcc | tgagcaacaa | 10320
| agtaagacct | catcactaaa | aacaaatttt | ttaatactga | agaattttat | ttgctggtat | 10380
| tttgttgagg | attttgcatc | tatattcaca | agaaatatta | ctctgtagtt | tttcttcttg | 10440
| tagtatcttt | gtctggtttc | agtatcaagg | caatgctggc | ctcatgagat | caatcaggaa | 10500
| gtgttacttc | ctcttttatt | ttttggaaga | atttgagaga | attggtgtta | attcttcttt | 10560
| aaatggttgg | tagaattacc | agtgtagaca | tctggtcctg | ggattttctt | tgttgggagg | 10620
| tttttagta | ctaattccat | ttccttactt | gttattagtc | taatgagatt | ttctgtttct | 10680
| tcttgagcta | gttgtagtag | ctcatgtgtg | gaattttttct | atttcatcta | agttatccaa | 10740
| gtttacctaa | gttaaagttc | cattttatct | aacttgggta | agccaacaaa | caatactaaa | 10800
| ttgttcatag | tattctctca | tagtcctttt | tttctctaaa | gtcagtaata | acgttcactc | 10860
| tttcatttt | tcattcctga | ttttaataat | ctgagttctt | tctctccccc | tccctgcaat | 10920
| tgagagtcat | ttaaaagtgt | cttgattaaa | ttttatatat | ctgtgagttt | tccagtttc | 10980
| cctctgttat | tctcttctag | ttttatttca | tgtgatccaa | aaagatactt | tatatgattt | 11040
| caattttttt | acatttacta | agacttgttt | tgtgactaaa | atatccttga | gaatttccat | 11100
| gcacatttga | gaaaaatgca | cattctgctg | ttgttggaca | gagtgttctg | tatatgtctg | 11160
| ttaggtctaa | ttggtttaga | gtattgttct | agtcctctct | ttccttattg | atcttctgtc | 11220
| tagttgttta | atccattatt | caaagtagtg | gccgggcacg | gtggctcaca | cctgtaatcc | 11280
| cagcactttg | ggaggccgag | gagggtggat | cacaatgtca | ggaggttgag | accagcctgg | 11340
| ccaacatggt | gaaactccgt | ctctactgaa | aatacaaaaa | atttgctgga | catggtggca | 11400
| cacgcctgta | atcccagcta | ctcaggaggc | caaggcagga | gaatcacttg | aacccaggag | 11460
| gcagaagttg | cagtgagctg | agatcgcacc | attgcactgc | agcctgggca | acagagcaag | 11520
| actctgtctc | gagaaacaac | aaaaacaaaa | acaaaaaaca | aagtagtgta | ctaaagtctc | 11580
| caactactat | tgtagaactc | tatttctccc | ttcaatgttg | caaaattttg | tttcatgtat | 11640
| tttggtgttc | tgttctttat | aattttttata | tcttcttaat | ggatgaaaac | ttttatcaac | 11700
| atataatgtt | ctttgtctct | tgagactttt | ttttttaact | taaaatctat | ttgggctgat | 11760
| aatacagcca | ccacaactct | catattggtt | gttattttca | tagaatatct | tcttccatcc | 11820
| ttctacttta | aaattcttct | atctttatat | ctaaagtgag | cctcttgtag | atagcatata | 11880
| ggtggataat | gttctctttta | ttcactctgc | caatatctgc | cttttaactg | gagtttaatc | 11940
| tatttatata | taaaataatt | actgattagg | aaggacttac | ttctaccact | cagctatttt | 12000
| ttttctgtgt | gtcttataca | tttttaagtt | tctcaattcc | tccattactg | gattttttt | 12060
| tttacttctt | gattttgtgt | ctgtgttgtt | acattttgat | tattttctcc | ttttgatagc | 12120
| ggcaggaggc | agccaaatgc | ctggcagata | gaagcttgtc | ccccatgaaa | ccccaccttc | 12180
| aagccaaaaa | atagcctgaa | ggctgaaaga | ccggactgct | ggtcccagat | gaaacccatg | 12240
| atccagagtc | agaacttcca | ttcctgtttg | cctgccctct | aaataatccc | ttttaaccaa | 12300
| tcgaatgttg | ccttttccaa | tactacctat | ggcctgcccc | tcccccattc | tgagcccata | 12360
| aaagccctgg | aatcagccac | attgggggca | ctttgccaac | ttcaggtagg | ggaccacct | 12420
| ctgtatccct | tctctgctga | aagctgtttt | catcactcaa | tgaaactctc | accttgctcc | 12480

```
ctctttgatt gtcagcgtat cctcattttt cttgggtgtg gtacaagaac tcgggaacca   12540
gtgcacaagc cagacttggt ctgggcagca cgggttagtg ggccatctcc cacagcaggt   12600
agcatggcca agtgaggcct gggcagggca tcaccaaggt ccctggcttg caaagtgacc   12660
aaggaaaaaa tcctgtgtca ctttcctttt ctcatatttt ttagttattt tcctaatgat   12720
tgccttgagg atggcaatta acatcttaca cttataagaa gctagtttga ataatagttc   12780
caatagtaca tgaacactct actcctatat atctccatcc ttcttccttt atattgttat   12840
tcccacaaat tatgttttta tacattatat cctcactaac ataaacttat tattattttc   12900
tgcatttgcc ttttaaatca tacaggaaaa caagaatcac aaagaaaaac tacattaata   12960
tttgctgtta tatttaccta tatagtgaca tttaacagtg tattttatg tcttcagatg    13020 tctttgaatt actacttagt gtcttttcat tttagcctca atgtttccct ttagcatttc   13080
ctatagggca ggcctgccgg taattaattc cctttggttt tctttatctg aaatgtctaa   13140
tttctttttt attcttgaag aatagttttg ctggctataa gattcttagt taatagtttt   13200
tttcccagca cttcaattat tattaaagtg ttattattat tattattatt attttgagat   13260
ggagtctccc tctgtcactc aggctggagt gcagtggcgc aatctctgct cactgcaacc   13320
tccgcctccc aggttcaagc aattctcctg cctcagcctc ccgagttagc tgggattaca   13380
ggtgcccgcc accatgccca gctaattttt gtattttag tagagacggg gtttcaccat    13440
gttggtcagg ctgatcttga actcctgacc tcaagtgata cacccacctt ggcctcccaa   13500
agtgctggga ttagaggcat gagccaccat gcctggtcta aagtgtaatt attattacag   13560
ctgccatttg gcctccttgg tttctaatga gaaatcatct gttaaactta ttgcaaatcc   13620
ttggtatgta tgctatgtgt catttctctc ttgctgcttc caagattctc tctctgtctt   13680
tgtcttttga caatttgact ataatgtgtt tcagtgtgaa tttcttagag tttatcccac   13740
ttggatttca ttgagcttct tggatgtgta cgtttgtctt tcaccaaatc tgggaaatta   13800
tttcaccatt tctcaaatat cttttctttc cccttccat ctctcttctt ctggagctcc    13860
cgtatactta gttggcatga ctgatggtat cctactggtc cctcaggttc tgttcatttt   13920
tcttctttct tttttctgc tctgcagact ggataacttc aatcgccttt tcttcaagtt    13980
caatgattat ttcttctgcc tgctcaaatt ggccatttaa cccctccagt gactttttca   14040
tttcagtatt gtacttttca gatccagaat ttctatttgg ttcctctta ataaattctt    14100 tttattgtca ttccccatct gttcatacat tgctctccca atttcctgta gttctttgtc   14160
catggttttc tttagttaat taagcatatt taagacagtt gacttaatgt ctttgactag   14220
taattccaat gtctaaaatt ccttatggat agcttctttt aaattatttt tgtcctgtta   14280
gagagtcata tcttcctctt tatttgcttt gtaatacttt gttgaaaact taacattttg   14340
agtagtaaaa tgtggtaatt ctgaagccag attctccccc tcctttgaga ttggttttgt   14400
tgtttgttga gggctgcagt tgtccatttg tatagtgact tttccaaacg attttttgcaa  14460 agtatgtatt ctctcttgtg tctggtcact gacgtttctg ttctggtgcc tctgcagtca   14520
gcctatgacc tggaagagca ttccttaaat gcatagattt ttttaaaacc caagaaacaa   14580
aaaacctagc atgtatgtac ctttttaaaa atcttctgat agatgccacc tggaaggctg   14640
ctgctgcctg aaggggcaga aacaaaggca agctctactc tgagccctca gggaaccacc   14700
agataaacaa aagaaatttg attctccaaa tttctggaag acaaggtcct ttctgcccac   14760
tcctgctcca gccagctgct ctaggaacac aattactgtc cacatggcca caggaatgtt   14820
gaagaatgca ggatggtagc tggtttgccc acaccactca cttatgagcc atcagcatgc   14880
```

```
ctctcccttc atcgagcact cccatggttg ctgtaagtgt ccaatcaggt tccagaattc   14940
tgaaagagtt gactcttaca ggattttttt cttttctaac ttgctggttg tttagataga   15000
ggaaccaatt cctgaagttt cctacgttgc cagcttcatg aggatcattc cctagtaact   15060
cttttcagac aaaaagcttc attgattttac tgtaggacta gcatcaaaga gtctatgcca   15120
cctagtctgt ctccttaaaa cacagaaata atcagtatgc attggggtag gagtttggca   15180
ttagatctgc cgtaaatcaa gagctgggga cagcccatgt cttaaactct gacccaaggg   15240
ctaaaatatc ctttggtagc aacaacagct acaaactatt gaacaacttg tatgtgccaa   15300
gagccttacc tgcattatcc cattgaatcc tctcaacagc cctgtgaggt agtagaattg   15360
ttgcctgccc cttactgagg cctagaaaca ttaaggaatt tgcccgaggc cctagagcca   15420
gtgagtggca aagccagtct ccagactcag gctggagatc ctacagttct gtgttacccc   15480
agtgttatcc tgcctctcag cacagagtct tggatgattc tcctaacccc tccctaggca   15540
atgcacaggg ctgctccctg cacccttact catgctctgc tcttcaaccc caacagtgct   15600
ggccttaggc tttatccctg acacccagcc ccaggctcca ttccatctgt tgacagaggc   15660
aaacactggg gcaaaactga cctctgtgga taccactgtg tccacctcca ccagcttcag   15720
ctgaagcctc tgaacatctc cagcatggaa gaagccccaa aggatatttc ctgtccccca   15780
gcatatgctt gaccctgaag ccctccccat ctagtcaaga agaccaaaact gttaacaatc   15840 ctggagtcag agtgacccat gggtgaatct tagccaagtc actcatagct gttgcatcct   15900
agtaaatccc ttaactccca taggcttcag tttccctgca tataaaatga cagccttcag   15960
ctcatcggcc agtttcaatc catctaaagg gtctagcaca tccctggca tgtggaagcc    16020 acagggcaca cactagttgt ggtcatttga tcctggcatg ctctgctgtc tctcggctct   16080
cccctggcct cttttccctga tgtcctggcc atcagccact gcctaacacc ctcccactca   16140
ccaggccctt agcctgcccc ttagcacaag agcacagccg gtctcaagtc taccctgctg   16200
taagcaaaca cttgcaacat catgctgacc tccaggccct gttgcatcag cgtgcccaca   16260
cttggtgccc agctggtact gagggtatca gggaacaggc cagtggtgga agggcggaca   16320 cttttgggttc cctggttttcc tggctcccaa tatctttccc aatggcatat ggggtctagc   16380
agcttggctc atttaactgt gaacctctac cctttagaat ctgggcctcc aggcttgctt   16440
ctgtgcaaaa tggcagataa ggctcaacct ttcttttttt aacttcattg ttaaatatta   16500
ctccattaat acccatttac tgcagaaaag gtaggaaata cagataagca aaaggaaaa   16560 taaattaaaa tcctcatacc accatcatca agataattac tgtcaccatt ttggtatatt   16620
tcctcccaat acatatatta tctatatcgt atatacgaca aaaatggatc atactatgtt   16680
tcctgttctt cccctgtgtt agtcatctat tgctgtataa caaactgcct caaaacttag   16740
tggcttcacc tttccgtgta ttatgatgac aagaatgtgg tatgacactg tcttatatct   16800
ggatcatatg ctaaaagata gaaaatggtt tctaaactta tttgttctgt aataacaaaa   16860
ttttatttca taaagtgttt ttaaaaaaaa ccatagtagc ttgaaacaac aaacctttgt   16920
tatctcacac agtttctgta ggtcaagaat tcagaagcag cttagctggg tggtctggct   16980
tggtgtctct cctgaggtca gggttttggc tggggctgca tcacctgaag gcttgactgg   17040
ggccagagga gctgcttcca aagtggtcca ctcacatggc tggcaagttg gagttgcgta   17100
ttggcaagag acttcgcttc ttctcaatgg atcttccag agttcttgta ggcaacctca    17160
tagcatagca gttggcttcc cccagaggga acagtccagg agagaacaag gcagaaacca   17220
cagggtcttt tctggcttag gctccaaagt catactccac catttctgca ttatcatatt   17280
```

```
agttacacag gctagaccta ttctgcatgg aagagactat accatggggt gaataccaga    17340
agcagggcta attgaaggcc agcttcaagg gcggctacac attccctttc aacagtatgt    17400
catgaacatc tttccatgcc aatagagcag atgaatctta ccattttaa tgactacatg     17460 taagtgtagc ataatttatt taaccaacct cctgtagttg ggtatgtggg ttgtgtctcg    17520 tttttgata gtagaattaa tcatcttgaa tatccatcac caaacttgtc atattatttt     17580
cttttgatga atgaaaaga aaatcaagtc atgtctgtca atcagaaccc tgagcaacta    17640
agaaatgggg gtaccactgg gacatagagc aaggtcccctt ctgattctgc tcttgtcttt    17700
ctctccccat gaaatgggga gttcactatc tactgagaca tcctagccca cagctgcaca    17760
gttctgtctt tttagaaagc tctaagcaga aacaatgttc atccatcctc ctcgggacag    17820
cccttgagct actgaagact ctaagcatgt cctggtcatc ctccatgagc catcatctct    17880
gaggccctcc ccttcttggc ccctcttctc tggacaggtt ctggacagtc ttgcccttcc    17940
aaaattcctg gaaagcagga actgttcctg ctacaatgac tctcaactcc agtgcagtac    18000
agactgttgg tgtcacccct tatcctgaag aagaggcact gagacaggac aagggtgggt    18060
gcccaggagg gctggcatga gtcatgagaa tctggtcccg gagaattaga cggtgtgggg    18120
aagtaggggt gttgggccgc tttctggcct catggatgcc aatgaatatc agcaggtggc    18180
tcccagaaag gaactctagg ggatgcctgt tgctctaaat agaggctaga gagggcactg    18240
gcagttcagt caaccaagaa aggggggccca cttgcctcag cttcaggctt tgtacacatc    18300
ctcagccttt cttgagaact gaatttagat tctcctcccc tgtgctgtgt gcttggccca    18360
gaagaagggc aagtctcgct gggtggctgc ttcttggcct ggctgaacca gaaggcccca    18420
gtgccactcc aaacctgggt gtgagccctg cccccatgag caaacagtag ctcagagctg    18480
ggggctgtgg gggtcagtgg cctgtcacat gagatctgat gaggccatct ctgctctata    18540
ttgggaaagg gatcaattgt atcaagggct ttcttgggag tgatcactct ggccattggc    18600
gagagacctg gcattctgac aaggcaccct ccataccctg acccacttgc cagctccagc    18660
taattttagc aggctttggc aggtgccagc aagtacatag catgtggatg tcactcccag    18720
gtgagcccaa ggagaggcct gggccagagc ctggaagtca tggtctatgc ccatggaggc    18780
acccaaagca agcctgaggc ctggactttg cagtcacaaa attaagaatg ataccctgt     18840 tttttgtttg tttttgatca gttggccacc ttcctccacc accccttccc caagttccat    18900
acagacccct ggattgtatg aaatgcaaat cgaacctctc tgcagatgaa aatccactgg    18960
ggatcccctt gcctccaaga gcaagtccag acctgcacca cgcgcgggcca ggccccctta    19020 ggaccccctc cctgtccaag ggcatttcag taagtgttct gtggccaagg cagcctggtg    19080
actttctgcc cgcacaaggc tgaggaatgg aagatgggta ggctggctct gcacaccccc    19140
tcctgctggg cagcaatccc taccccatgt tcacagagtg tggccggctg ccccatggct    19200
ctgtccccgt ggccctgtca actgttaccc acatggccta ccctccctttt ctgccctgcc    19260 tctgacccca tggcagggggg cagagtattt gagcagccgc caggctgagc cctttcagtg    19320
cagaagccct gggctgccag cctcaggcag ctctccatcc aagcagccgt tgctgccaca    19380
ggcgggcctt acgctccaag gctacagcat gtgctaggcc tcagcaggca ggagcatctc    19440
tgcctcccaa agcatctacc tcttagcccc tcggagagat ggcgatggat gtcacaagga    19500
gccaggccca gacagccttg actctggtaa gggtcacacc aaagttaggg actttgcact    19560
gggagagcag cacccagggc agggcccttg gttttgcaga ttaccaaaac taaggctggg    19620
ggcagggaag gcgagcaggc ttggggcacc ttggaaggag gcacatgggc cttgggggtc    19680
```

```
ctggctaggg cagctgtgcc tgccactggc cctctgccca ccaccCctcc tcactgtggc    19740
tatccagtgt ccagcctctc gaggggttct agggtactta ttcctggagc taacggtgac    19800
ccaggacacc agtgtccggg gcctggcctg gggcttttat gggggagct ggctggctgc     19860
ccagggctgt ctggctctct gggggctctg catggcattt ccaggggttg gtggatcagg    19920
gattctgtcc ctcaggagaa tgtgggcact agcccaaggc cactcacttc tgtgtacata    19980
gccacctgag ggcccaggaa tggaggggc caggctacag ctggacatct ggcactcgga     20040
tgggctctgg agccccagg cctgcagcat ctgcccaggg actgccctgg cccttggcca     20100
tttcctcagg gacccacagc tccaccagcc ggccctccc agtgctggaa tagacagttc     20160
ctcagtccac atctgccaaa ggcggcacta gaaggcatcc tgcctttttt actgcgttct    20220
ggaggtgggg tcacaaagca ctgctcactg cataaaaggg acagcatcct gccctggca    20280
gccctgcctg accagctccg cctctcccac tgctatccaa cctgtacacc ctggtgacca    20340
tgtccaggcc agtggcctta aggactgtct ctgtactgat ggctccacat ctacctctcc    20400
agccagactc tcctctgaac tcgggcctca catggccaac tgctacttgg aacaaatcgc    20460
cccttggctg gcagatgtgt taacatgccc agaccaagat cccaactccc acaacccaac    20520
tcccaggtca gatggaacct cttcttccca ggcccttctg ttcctctcct cagcccctcc    20580
cacctccctt cagaataagt ctagactctt atcgctttca ccaagcctgc gcccagcatc    20640
cctgcacagg gattgttagg acagcctgac gccctgcttc caccctgccc caagatgccc    20700
ctgctctgca gccggcgcc tccaggcttc tcacctcctg ctgctcacag ctcagcctca    20760
ctccctccct ccccgcctct gctccagcct cagtgcaggt ccctgctcc catcttctgg    20820
cagcagctgc ccgacctggt ccctcttcat ctgtccccat tccttcaccc ccagcctgt     20880
ccccaacttg actgaggttc tttcctgcag atccccgccc ttgagagggg ttggtcccac    20940
tgtcaactct gcttctgtgc cctgtgccgc acctggcatt cagtgagcat ctgctgaaga    21000
gatgagggtc agatgccctg cagggagtgt ggggcgtcc tcaggcaaga aaagttgtac     21060
gtttggctgt gggccctgat tatgtgtcct gtgacctctt gggtgaggtc agcaagagaa    21120
acctctgcaa gctggctggg gctgcctccc agaggctgcc aggggaggg acaggctctg     21180
tctgtgctct tcttccgagg ctacacctgg ggcgccaggc tctcagggct ccccaggtac    21240
caccacattt cctacactgc ttgggaaagc cctgtaagtt tgcacagaca cccagcatga    21300
ggctcgccag agagatactt gtagctgggg tctgggcacc aggaacagct tggtgctggg    21360
cctgaagtcg ggcaggatgc agcctggcca ggtgagagga aagcttggag ccagtgcctg    21420
ggttcaaaact cctctgtggc ctatggttct gtgggcttgg ggaagggttt gtacctctgt    21480
gtccagtttc ctcacttata aaaaaggag ataataaaag tacccatgtc ccagggtggc     21540
tgtagcaata atagggaggg gtgcccagag caggtctggc acacaggaag tgtgcatcag    21600
cctcagtccc tgccattggg cttgtcctgg gagtctgtga agccaacctc tgctccacaa    21660
tgtgaccccc aggcttgtga gaccaagctg ggtcagagct tcctcctctg ggttgcacc     21720
aggaggggaa cttctgcagg cccagatgca ccctgaggaa agggcttgtt cccaccaaga    21780
acaaggctca ccttttggagg atgctcccca catgagaggt gaaccCccag gtctactggt    21840
gactgcagcc tcggaagctg acagcatcta tcctccaacc catgcccact gggaagtgtg    21900
tgaggggtcc tcataggccc tgcggtgtgg acaatgcaga gaccctgtag catctggcta    21960
gggcggggcc cagataagag ccctgtgcca ggagagcctg gccggttctg ccactgtggg    22020
gagacaggct cccccacccc atgtcccctg cttccctgca gcccacagag aatacagacc    22080
```

```
tacttttaca gaaatccaga tttttgtgta aaagtgtctc tattttaagt agattttaag   22140
tggtggcagc aaatttaagc tttgagaat attatacaga acaaatcaga ttcacaggcc   22200
agatgcaact ttatttacag aaatgggatc aggtcctacc tcaggtccca tctcacgttt   22260
tcacttatgc ctatacgtct ccttcacggg aaaggccaca agaggccctg cggtaagtgt   22320
cccggtgttg atttaaagtc cccaacagtg aatatgaggg tcctcactgt tgcagcaaga   22380
ggataccccc ctgtgtatct tggaaatgcc tgcagccctc ttgctgcaga acagattctt   22440
aggagagaaa ctgtcagatc aaagttaaac ttagagaaac tccaaattgc cctctgaaca   22500
gacggtatca gtttgacatc atccaatacc gggattcctc ggggagaact ttctggccta   22560
gaaggcagta gagccaggac ttcacccagt cagtggcagg gccacacgtg ggccttgata   22620
cagaggggga agacttgagc ctcctcgaca ccctacaggg cccagcctcc caacatgtga   22680
taagagaaac aacagccaac ttgtacctag ctctccttat tctccaaggg ctgggccagt   22740
tctccccaca gccctgcaag ggaggatcac tcaagggccc caactgtctg acaatacagc   22800
cacactctga tcagccacct gggcataggc tccatgccat tgtcctccgc caagacctca   22860
gactgaaatg ttggctcctc ccatgaagaa cctggggcca aaggaccaga gtccaggtcc   22920
gtggctgcca ggatgggcca cttggagaga ggcacaaggg tggtgccagg caggtgtgag   22980
ggctggacct ttgcaagagc agcatcactt ttgttgagag cccacaggta tcttataatt   23040
gggtcctagg acttcctgcc agtagccatt gtgtgcatgg atttgggtgc tggcctcacc   23100
atggtgtgct ggctgcccat gcctgcaata atgacttctg taagcctttc ttcatctgca   23160
agatgggtgc tgctggcacc tcctccccgg tgctgtggtg acagggcata gtgtgtgagg   23220
ctgctatgtg aagcacctaa tgcagggcct ggcatatgga ggaattcagc aaatgacaga   23280
tgccttcaca gttagttcct ggcatcctct acattggtgg gtgtaggaaa gaaagacaga   23340
ggaggcaaaa gttgtagctg tggggcattg aggacagcct ggattgttcc acagagccct   23400
gaggacatct ccagggtgt gctctgcagg ggcagctgga ttggagggtt aggggtcggg   23460
gagggcgtgc actcccaccc atgctcacag cctcggaaca gtgcctgctc agccaacatg   23520
ggtgtttgat tctgtgtctt ttgtcacaga ctttatcagc cccatccctt tctgaccttg   23580
cctcagttta aattttacat gtggggcctc attaagagac atggttctta actaaagatc   23640
tgtatccatt aggaatgctt tgggctgcag gaagacaaac acctgactca ctgtggcata   23700 agtggttgc gtctgctccc ataagctgca cgtggagggt ggatctggca ttactctctc   23760
ttccctacat ttgcagtatg ctaacagctt taacctccag ccttgttct tcatggttgc   23820 agggtggcta tcacagcgct ggccatcaca tccttacaca gctgtgttta caaatttagg   23880
gggacattga agctcctccc ctgctaaaat caggcttccc ttcacctgtc attggccaga   23940
actgggtgaa atgcccaact ctagaccgat catcagtaag aggagtatag aattgctgtg   24000
cccaccttag attaatcatg gcgcaatgtg ctccccatac caacaaaatc tgagttctag   24060
aaactgagga agaagaggaa aatggccgtc ttgcctcctg gctgggattc agagcatctc   24120
caaccctctg agcttatgtg taagactgtg gcaaaagtg tgtgagtttt tgtggaatgg   24180
atccacggct tttatcagag catctttcct tttctttt gattcaagat gaaaatattc   24240
ttatgattat ttttctcacc actgcccaga gataaccagc acattaacat ggcctttct   24300 ccatgaatag cactagggtg cccagtggac agacacatag ctgtccacac accagcttgc   24360
tggggatgca taggcagagt cacatctgca ctcacggcct gtcctcacac tgccatgtgg   24420
agagccagca gccacaccat gggccgtcca tgctcacggg agtggcagta tcagatctga   24480
```

```
gcttcgtgtg cccaggcgtc tctcacatca gtgcataggg accctctttg ttctgtggcc   24540
cagtgtgccc atgccacaga tggcttcagt cagcagacac ctccttctag acactcacac   24600
tcactcctgg ctggcccttc gcacacctgt gcagacaggc ccatttattt tcttgtgtaa   24660
atcccaagta ggaggactgg gtctctctga cagcaatgcc agctgcctgg cacccctccag  24720 acaggtggct caagccccac ctcgccagct ctcccagtta gcccctcctt tccctggctc   24780
tgacctgagg gacgaagcag ggtgctacag gacgctgtgc cacagggata tcgtcaggga   24840
cagaagctac tctgccctct gctgctcacc cctccaacac gctgtgggct gcatttgttg   24900
agtggctggt accagactct gctcttctga cttccagct ggttttacct gtagtaaagt    24960
ttgagaagat gggtcatcct gaccccgggg tcagaagaca aaggaggcc catggcgtgt    25020 gggggagatg ccccgtgagg ccctcggtgt gcagatgcct ggtgacagcc cacctgag    25080 gtccccagcc tacccctcc ccagcccgac tgctcccatc cccctccctg tgcaggtaga    25140
gcagatcctg gcagagttcc agctgcagga ggaggacctg aagaaggtga tgagacggat   25200
gcagaaggag atggaccgcg gcctgaggct ggagacccat gaagaggcca gtgtgaagat   25260
gctgcccacc tacgtgcgct ccaccccaga aggctcaggt accacatggt aaccggctcc   25320
tcatccagaa gcagctgtgg gctcagccct agctgggaga agcaccccag gcactcccag   25380
actcacagcc agcccgagac agaatctcct ggggagcaat gaagtcctcg acttgggcca   25440
gttctcaccc ttggctcctc tggtccggcc ctggggcact cgggctcacc ctggagctgg   25500
caaacctcag gaaaactggc gttttaaatc tcactcctgg ccaggtgcag tggctcaccc   25560
ctgtaacttc aacactttgg gaggccaaag caggcggatc tcttgaggcc aggagtttga   25620
gaccagcctg cccaacatgg tgaaaccccg tctctactaa aaatacaaaa attatccagg   25680
catggtggca cattcctgta gttccagcta ctcgggaggc tgaggcataa gaattgcttg   25740
aacccgggag gccgaggttg cagtgagcca aaatcgcgcc actgcactcc agcctggggt   25800
gacagggtga gacaccatct caaaaaaaaa aaaaaaaaa gacctcactg ctccccatgg    25860
gcacttaggg aactctccca gcccagttct gcagctgggc cattgcacta gatcctcagt   25920
tggtccctgg gctctcggtg actgtccagg gcaggagttt cccattgact tttccctggt   25980
tgacctttga ccccttccac agttgacact ggtgtcccca ggtgtctggt ggccccttgt   26040
ccagctccct tagtcccttg tgccttccct cctcctcttt gtaatatccg ggctcagtca   26100 cctgggccc acccagccca aggccagcct gtgggtgtcc ctgaggctga cacacttctc    26160
tctgtgcctt tagaagtcgg ggacttcctc tccctggacc tgggtggcac taacttcagg   26220
gtgatgctgg tgaaggtggg agaaggtgag gaggggcagt ggagcgtgaa gaccaaacac   26280
cagatgtact ccatccccga ggacgccatg accggcactg ctgagatggt gagcagcgca   26340
ggggccgggg caggggcca aggccatgca ggatctcagg gcccagctag tcctgacggg     26400
aggtgccacc tgtctaccag gggtggggag gcggggggct ggaggaccac ccagcctcag   26460
aggcagctgg aggcctgggt gaacaggact ggccaacatg tccccaagtc ccacagtcac   26520
catctggcca gcattgagag gggaacgggc tgaggaagag ttagtggcaa gaggaacccc   26580
agccagtcac accttgtcca gtttaccaga ggaaaaacca atgtgtaaga acagaaatgt   26640
gacccggcag ccagtgcact gccccctct ccaaaggcca cccctcaccc tccaccagca    26700
tgcacagaaa gtgggtgac agcaatcaca atgtctaccc aggcagcaag gacccctgac    26760
catggggagg actggggtgc agggaacata gaagcagaat gaggcctagg gggagttggg   26820
caaggccaga gccctagctg cagccaagca catggccaag gccagctcct ggaagggcag   26880
```

```
ggctccgagg caggaggcag gaggctgccc gtggctaccc gtcctcacac ccctgcagct    26940
tgctagtctg tctgtgggct gggtgtgaat caaggcagtg ggatggtgtg gggacctccc    27000
tggccccagc agccagtgag gagcctggtc agtcagcaga gcattcagca gtatccagtt    27060
ccatggagag gcccgtgtga ggggagtcgg ggctggtctt cagtaaggat gggtggccag    27120
ggcccctaga agtagaaaag gagactccgg gtgctggaga cagaaatcaa ggatgtgcct    27180
ccatgtggag cctcaggaat agctggccag gcctgaggct gaacctcaca aggttcagct    27240
gggagggcta ggctgacaga gcacagccgg gccagggacc agcctgccct gtgttgcctt    27300
gtcccgaggg ccactgtcag caggtctctg gcatggggga ggcttagggc ctgagcccaa    27360
caagcagcag cggaagagga gagggaaact gtggacaggc ctggcattca gtggccaggt    27420
gttgcagtgt ccctgaggaa tagcttggct tgaggccgtg gggagggctg ccggccagcg    27480 cacccccca tgccagatgg tcaccatggc gtgcatcttc cagctcttcg actacatctc    27540
tgagtgcatc tccgacttcc tggacaagca tcagatgaaa cacaagaagc tgccctggg    27600 cttcaccttc tcctttcctg tgaggcacga agacatcgat aaggtgggcc gggtggaggg    27660
gcagaaggca gatgagggga ggcacaggca ccccagagga actctgcctt caaatgtagc    27720
ccccatacca tgtgctcaga agggagatct ggattcaaat tgtggccatg tcacctgcca    27780
cctctaatgc tgtggaaaag aagcatcaca ttagctaatt ctggctgtgc gccttgtgag    27840
gcaccagcta tgatcacccc actccagtgg aaagagcagc tggcagtagg gtgggctca    27900 aactcaggca gccgggctct gggtcacctg caggccacgg tcatgtcaca ctgcctctag    27960
ctgagtcaga aatgtgaagg aactgagatt ctacccttcc tgcaagctag caaagtggcc    28020
tgccagttac atctgtgcat gcacacacac acacagttat atatgcacac acataaaaca    28080
cgagaccttt gggtcaggga gaaagccaga tcctcactca cggcagaagc agcagccaaa    28140
gcaacatctc atgtggtttt ccaagcccca gtccctacag agacagagag gccaggtgg    28200 cacctgtgca tgcagcgggg taccttgcag gagggaaatc ctgattttac acaaagctgc    28260 tcccccacg ccctgccttg actctgggat gacgtctcag agctgtgcag tacaacattc    28320
ttaaattggc tgggactcag ccctgcagaa atatgatatc ttcaaggaga atcgttccca    28380
aaacctctca aagctatggg gctgctctga gcctgtttcc tcagctgtaa agtagggtgc    28440 atactttat ggccctgtgc aggaggtagt gacaggccct agcaccctgc ctccagtata    28500
tgttagcagc cacgaggcct atctctcccc acagggcatc cttctcaact ggaccaaggg    28560
cttcaaggcc tcaggagcag aagggaacaa tgtcgtgggg cttctgcgag acgctatcaa    28620
acggagaggg gtgaggggc acctgtacct gccgggggg ctgccctggg ccacccaccc    28680
cagcactgcc tgcctttctc cttggcttcc agcactgcag cttctgtgct tcttggcagg    28740
actttgaaat ggatgtggtg gcaatggtga atgacacggt ggccacgatg atctcctgct    28800
actacgaaga ccatcagtgc gaggtcggca tgatcgtggg taagggctcc ttgcacccct    28860
gccccttcca gactgctgag gctccctgtg tacaacaggc ttcaagggcc ctgtggggtg    28920
aggaccaaac tacttaacaa ccggtgatgt cagagcagag cctggtgcta cagcctgggt    28980
ggtcttgggg tatcaagatg gaagcaccgt gtacagtagg aagcatttca cgccatgat    29040 gccacattcc tgcatcagat ggtatgccag ctgcatatcc acctcaccca tcaggattat    29100
aattaaaaca cttatctggt aaattgacca actggacaga ttggtccaag tggaagagga    29160
taagcaaaag tggtaccatc tccacccgaa tggtctttcc acgggcctgc ccctgccct    29220 gccccacccc aaagtgaagg caggtaccag gaaagggagc agcagtccgc ccctcccagc    29280
```

```
agagggggtct tccacaccaa ctcggacctt tctcagaagt tccggaggtc attataacca    29340
gccttcactg aggagcaatc caatcagatc agttatctgc tgtgcgcaca gccgtgtggt    29400
tctatacttc tcttacttcc attttcacct ttcagaagga acgttgtctt taaatccagc    29460
atctaaacgt gagccccagc catccctggc tgtgatcccc ccagccctttt ccaccctatc    29520 ctctggaact gcctggggct ccccaagaca cttccacatg aattcccacc aagccaagct    29580
gcagctgctg ggcccaggca taaccccctcc tggggcagag gtggcaagga gtgacccacc    29640
actcacatct gccccacatc cactcttgac tctgctcagt gttttaaaaac atgtttataa    29700 caattaccaa gatctgaaaa ttaggagaat tcacatcaaa gtctggattt ctgtttgttc    29760
ataaaaaact agaaggcagc caggcaaggt ggctcacgcc agtaatccca cactttggg    29820 aggctaaggc aggcgggtca cttgaggtca ggatttgaag actagctggc caacaaggtg    29880
taacctcgtc tctactaaaa atacaaaaat tagctgggtg tgatggcgca tgcctgtaat    29940
cccaggtact caggagactg aggcaggaga attgcttaaa ccctggaggc agaggttgca    30000
gtgagccaag atcacgccac tgcactccag cctgggtgat ggagtgagtg agactctgtc    30060
tccaaataaa taaataaata aataaaaact ggaagtctaa gcatcactga gccctgattc    30120
ctatgtggca gctcgactga ccagcatttg agttgctgtc cctgacagct ttggggggtgt    30180 gcagcccaca cagtcatgct agcttgaggc tctgctgtca gcagtttgaa actcttaata    30240
acttgtgaac aaaagactcc atgttgtcac tctgcacagg ggccagcaaa ttacaaaatt    30300
ccatatccgg aattgtctac aggagcctct gggctgctcc caagggccca ccatgcct    30360 tactcacttt gggttgccat ccaaacatgt ctcatgacaa agaagctcaa acatgtgcat    30420
ggacagtgcc agaaaacaag ggtcgtacat agacaaaata aaatgataac gtcccacaac    30480
catttctttg atacacactg tttctctcag tcctcccaac cacctaggta acaggcaggg    30540
aaggtgttac tgttgcctgt taggaaagag gacagccctg aaagctgtcc ctggccactg    30600
aagcaaccca ggtcttccag ccccagggag agccgccttt ccattgttcc agacaaagca    30660
gagacaggca tgggggagcg ggagagggac tcctgtgggc aggaaccagg ccctactccg    30720
gggcagtgca gctctcgctg acagtccccc cgacctccac cccaggcacg ggctgcaatg    30780
cctgctacat ggaggagatg cagaatgtgg agctggtgga ggggacgag ggccgcatgt    30840 gcgtcaatac cgagtggggc gccttcgggg actccggcga gctggacgag ttcctgctgg    30900
agtatgaccg cctggtggac gagagctctg caaaccccgg tcagcagctg taaggatgcc    30960
cccctccccc acaacccagg ccctgggccg ctctggtgca gcggcagatg ggagccggc    31020 cattgcagat aatgggcttg ttttttaaaca actctgggga aaagcaaact gacaatccgt    31080
tcgtaagctc catcccttct gctcagtcat gacctgcccc tgtgagagat gaagggttag    31140
tcccagttgt gatgtgataa gcccagacct cttccttcc gacaggtgat cgtgcatgca    31200
gaggaggctc tgagacgccc ccagcaaggt tcctgggttt aacccaacat tccccaaagt    31260
atgtatttgg ccacattcac agaaagaata ttagtctttt gtggaatgct gcgggttgac    31320
agtcacagct tggaaaccaa cccacagaga gctcatcatt aatcatggct atcacttgtt    31380
taccacctac tgtgccaggc ctatgctaat tactttatta gcgtcctctc tgccgctcgc    31440
aggcctctat tattataggt cagtagtatt cgatttattt aaattaaata cggaaggtca    31500
tagattaagc aagaaagtgc cagcaacatg gtgcgtgcct ctgactgggc actaaccctc    31560
caagtcttag ttttcccaac cataactggc caatgaacag cagctctgga tgcagctaaa    31620
ggaagactga agctgtaggt cccgtgctcg gcgcagggcc ccctgcaagg aaggtttcgg    31680
```

```
agggactgga tggggtctttt gaactatctg tctttcccctt tactgcagtg ggcccagggg    31740
caggccaaag ttgctcccgt gattgacttg aacgtgcacg ttcctaatcc ctgacatttc    31800
taaagctctg gctcattaac gagggaaaga cgtgaaccag ctgggggagt ggggatcgca    31860
gtgcccacg tggccgcctc gtgacctcag tggggagcag tggggccggc tcccggcttc    31920
cacctgcatg aggggccctc cctcgtgcct gctgatgtaa tggacctgcc ctatgtccag    31980
gtatgagaag ctcataggtg gcaagtacat gggcgagctg gtgcggcttg tgctgctcag    32040
gctcgtggac gaaaacctgc tcttccacgg ggaggcctcc gagcagctgc gcacacgcgg    32100
agccttcgag acgcgcttcg tgtcgcaggt ggagaggtgt gcggaggagg agggtgggtg    32160
caaagggcag gggctgggga cgcccgggca ctgcagactt ggtctcaggg cgacgctgag    32220
tcccaggccc ggggcgcagg gatgggaaac tagggcctgg ggcgggattc cgggcgtggg    32280
cggggcccgg ggcggggcac aggggcggg ggagtgggcg ggcccgagg ccgggcgctg    32340
gaggcgaggg cggggcaggg acgggtccaa gggcaggagg ctgggacagg acggggatgc    32400
aaagggaggg gcggggcccg agacggggag gagggggagg gcccaagggg aggaggcggg    32460
gtccggacgg ggatgccaag agcagggatg ggagcgagcc tgcgtccggg cactggtccc    32520
catccgtgag tcccctcggt gctccctgcc cgccgtggcc atcctctcac atcactcaca    32580
accccaaggc gcggcatggt tgacaccccc acgttaggac ggagaccctg gcttagtta    32640
gaggggcag tactaaccag tccctggcgg aaacgctttg gctgggtgag gtgagcggga    32700
tcgcccccat ttctccagag aggggtcccg gctcagcgag ggaaagaggc cgccgctggg    32760
gggacggctg gccgggcccc ctccctggag aacgagaggc cgccgctgga gggggatgga    32820
ctgtcggagc gacactcagc gaccgcccta cctcctcccg ccccgcagcg acacgggcga    32880
ccgcaagcag atctacaaca tcctgagcac gctggggctg cgaccctcga ccaccgactg    32940
cgacatcgtg cgccgcgcct gcgagagcgt gtctacgcgc gctgcgcaca tgtgctcggc    33000
ggggctggcg ggcgtcatca accgcatgcg cgagagccgc agcgaggacg taatgcgcat    33060
cactgtgggc gtggatggct ccgtgtacaa gctgcacccc aggtgagccc gcccgctct    33120
ctccctggta aagtggggcc caaaaagcgc gcgctccaag gttccttgcg gttcccaagc    33180
tccaagattt cgtagtcctc ttctcgtccc ccttggccta gatttgggg aagggtcgac    33240
tgcgtgcagg gcgcccggta atgaatgtgg aggatgaggt ggaggaggg acggcagccc    33300
tgcttctctt ctgcccagct tcaaggagcg gttccatgcc agcgtgcgca ggctgacgcc    33360
cagctgcgag atcaccttca tcgagtcgga ggagggcagt ggccggggcg cggccctggt    33420
ctcggcggtg gcctgtaaga aggcctgtat gctgggccag tgagagcagt ggccgcaagc    33480
gcagggagga tgccacagcc ccacagcacc caggctccat ggggaagtgc tccccacacg    33540
tgctcgcagc ctggcggggc aggaggcctg gccttgtcag gacccaggcc gcctgccata    33600
ccgctgggga acagagcggg cctcttcct cagttttcg gtgggacagc ccagggccc    33660
taacggggt gcggcaggag caggaacaga gactctggaa gcccccacc tttctcgctg    33720
gaatcaattt cccagaaggg agttgctcac tcaggacttt gatgcatttc cacactgtca    33780
gagctgttgg cctcgcctgg gcccaggctc tgggaagggg tgccctctgg atcctgctgt    33840
ggcctcactt ccctgggaac tcatcctgtg tggggaggca gctccaacag cttgaccaga    33900
cctagacctg ggccaaaagg gcagccaggg gctgctcatc acccagtcct ggccattttc    33960
ttgcctgagg ctcaagaggc ccaggagca atgggagggg gctccatgga ggaggtgtcc    34020
caagctttga ataccccag agaccttttc tctcccatac catcactgag tggcttgtga    34080
```

```
ttctgggatg accoctcgca gcaggtgcaa gagacagagc ccccaagcct ctgccccaag   34140
gggcccacaa aggggagaag ggccagccct acatcttcag ctcccatagc gctggctcag   34200
gaagaaaccc caagcagcat tcagcacacc ccaagggaca accccatcat atgacatgcc   34260
accctctcca tgcccaacct aagattgtgt gggttttta attaaaaatg ttaaaagttt    34320
taaacatggc ctgtccactg ttctttgact tctgtgcatt aggactgtgg ggacaatcta   34380
taaagagtct gcgtcacatg catgaagaca cttcagtatc tcggcaatgc cctccagaca   34440
gctcctccag ccatctgtgc caggggagt gtgaggagtg acagaccagg ctgtaggaac    34500
aggaatgggg tgtcatgggg gatggcagag cagtggacag tacactgcct ggcccgggcc   34560
cctgcttgcc tgcccatgga atgtgtgcag agggagtgcc aggccaggtg ctgctctgga   34620
gaagtggggg aatgaggctg gtcctgctgc aggtcagtct cagcaccgtc ctgtccagtc   34680
agagtcactt aggtttgcca gtgagtaggg gcccagatac atgttggatt tctaaggtcc   34740
ctccagatgc tcctgtcagt ggaacgccta tttagagtta gccaagcgta ggcataatgc   34800
catctttctg cagcataaaa tacagtgaca tagaaacata tttgtgtgat tttcatgcat   34860
tccttttttg atgagagata ttacccagct aattaggaac aactgttttg tttccttcag   34920
atcataaccc aaagttgtga ttttgaaaag tcatgtcccc cttcagattt cttgttttct   34980
gctacttctc atgtggaatt gctttggctc ttcttagttc tcttgagtct aaattattcc   35040
ttataagttg gtgcaagcat ctgattattt tgttatcatt actgttatgc tcaagcattc   35100
acagagtgga acacatttta atatcaattg cttctatt ctcctttata ttacagttca     35160
ggacattgta ttaattatta aaattctatt cgtaggtagg ttatatgact gaattgaaat   35220
agataaaatg aatttctttt ctagataaca aaggaggtgt cataaaacac ttgttatggg   35280
ccagtgtgat ggctcatgcc tataatctca gtgctttgag aggctgaggt ggaggattgc   35340
ttgaggccag gaatttgaga ccagcctggg caacatagc aagacccat ctcttaaaaa     35400 aaaaagggtg gggcggggg gcactgctgg gcgcggtggc tcatgcctgt aatcccagca    35460
ctttgggaag ccaaagcagg tggatcaaaa ggtcaggagt tcgagatcag cctggccaac   35520
atggtgaaac cccaactcta ctaaaaatac aaaaattagc cgggcatgat ggcgggtgct   35580
tataatccca gctactcagg aggctgaggc agaagaattg cttgaaccca ggaggcggag   35640
gttgcagtga gcagagattg caccactgca ctccagcctg gcaacagag cgaaactctg    35700 tctcaaaaat gaattaatta attaaaaaa gaaaaaaaaa acactgggca gggtggtgtg    35760
cacctgtagt cccaactact ccagaggctg aggcaggaag gagcacttga gcccaggagg   35820
ttgtctgcag tgagctctac tcatgccact gcactccagc ctgggtgaca gagctcagtg   35880
gcttacacct gtaatcctag cactttggga ggctgaagca ggcagatcac ctaagatcag   35940
gagttcgaga ccggctggcc aacatgataa aaccccgtct ttactaaaaa taaaataaaa   36000
taaaaaatat atataaaaat tagctgggtg tggtggcaca tgcctataat cccagctgct   36060
tgggaggctg aggaacaaga atggcttgaa cccgggaggc agaggtggca gtgagctgag   36120
atcgcgccac tgcactccag cctgtgcgag agtgagactc tgtctcaaaa aaaaaaaagg   36180
gaatttaaga aatttaaaag aaaactcttg ttatataaaa agggtattgg gtctgacaga   36240
taagagctcc tgcactctac cagccagcta ctgacagaca taggtctggc tccagtggag   36300
gggcagcagc cagtgagccc agcctggggt ggcccactcc tgctgcctcc aggatgtccc   36360
ctgtttcccc agcccctctg ctgtgccctc ggcccagaa gctggcgaga ctgcttctct    36420
ggaacagcat cacgcaggcc tgcccatcgg cccactgtgc accaggcctt ctgggatac    36480
```

```
agatgtcaac caggtggggt gctcaggagg ggcacagaag ccaggaatga caaacacatc    36540
agccaccagg caaatgggaa atgtgcccca gaagctccct gctgaggatg ttagggagag    36600
cattctgaag tagtgtggtt gagatgaggc ttgaggaagg caaggctcca aacagcaggg    36660
cagactggga gcaaggtaga ctgcatggga gggcagctga tggagctcct taaccctctg    36720
gaattgcccc aaagccaagc aaagtgttct tcttggggtc acagctagct cagggatgcc    36780
ttctgcccct tggtcagagg ggcaaaaggt cagagcctag ggtcaccaaa acctctggga    36840
agccccgggg gtctcaggcc acagaccatc ctcagaacta cacactgccc tcccatgcct    36900
ggcgggggcc ctggactggc cctcaccagc tgtcttcttg cactggccag ggttctggct    36960
ggactggcaa ggaggggtgg tcagatacag gagtaactgg atcccttcat caggacctag    37020
ggtggtgaga gctttgagcc tgctctgctc caggcagaca ttgtgtctgg ccctgccagg    37080
atggatagac agcaggatgt tacacgttga ggacatgaag gtcatcagga atgtggctgg    37140
aatctgttag gcctccccca gcccaggcgg gggctgccaa gtttgggcct atcctctgtt    37200
cctctcctta tttggacctt caggtgataa ggctgagaca taaggaggc tgggccctgc    37260 caccacgaca gcagccacac ctctgcagag agaatggtga gtgcctgctg gggaagaaag    37320
gctagcggtc tcccaggtgc tggcctttgg gctgggggag cagagttttc tgtgcttgtg    37380
ttgggttgag ggtggtcccc agggagagga agaggatcct ggccctggct ctcctgggaa    37440
tgctctggga ctgtgcatga tgggtggggt ggggagactc tgaggagttg gggagaggac    37500
ccctccctac tcacagtgtt gcaggccagc aggaaggcgg ggacccgggg caaggtggca    37560
gccaccaagc aggcccaacg tggttcttcc aacgtctttt ccatgtttga acaagcccag    37620
atacaggagt tcaaagaagt gagtgcccac tcccagtagc ctcagatccc atcctggccc    37680 ccccaccca cccacatac ataccccct tctaccctga ccttgcctct cacaccaccc    37740
aggtctctcc cccacctccc accttcccta gagctggggg ctgctcccac ctgaaggccc    37800
ccatcccaca ggccttcagc tgtatcgacc agaatcgtga tggcatcatc tgcaaggcag    37860
acctgaggga gacctactcc cagctgggtg cgtgcaccca cctcccaccc tgcgcactgg    37920
ggtccctact ctgagctgct gggcgggtgg gagtggctgg ggggacagga ctctgctccc    37980
ctgcttcccc tcctccccgt ctcctcacac tgcccttccc ccttgtcac gccttgcttc    38040 cacttcacct tcccgaccca cagctgcctc tgcccctcca gcccctgtgg ccaggatgga    38100
gggagggcgg cctgggcctt ctgggggaca cccagggtcc ctgtgtgcac ctcatgcccc    38160 accccacca gggaaggtga gtgtcccaga ggaggagctg gacgccatgc tgcaagaggg    38220
caagggcccc atcaacttca ccgtcttcct cacgctcttt ggggagaagc tcaatggtga    38280
gcctgggaca gagctgggca cccttggcca ggcagggagc ctgcaccctg cctgaacccc    38340
acctgaaccc tgcctgaacc ccacctgaac cttacatgaa ccccacctga accctaactg    38400
aaccccacct ggaccacct ggactcttcc tggccatgac ccattccaag cacatcctct    38460
gccccagaat cccatgtgca ctggtcaccc cagtgctgac ttggagccag gaaatgtgcc    38520
ttcagccccc accccaaat tccagtctcc cagccaagct gcccgcctca ggaggatgac    38580
cattcccagc cccactgatc cccgagaaac attttatgtt agggaatacc cccacctctt    38640
ctgggatgtg ggaggctcct catgcagccc agttcctcct gcggggacc tgggatgctg    38700 gagacatgga tgctcacctg gctgcctcgg ccttccaggg acagacccg aggaagccat    38760 cctgagtgcc ttccgcatgt ttgacccag cggcaaggg gtggtgaaca aggatgagta    38820
agtatgggcc cagccagatg aggagcaccg tggtggaagc agagagcggg gtgaggcccc    38880
```

```
tagtgagggg ggctgcctgt gcttcggggc cttacactgc tctttggggt gcagccaacc    38940
cttccctgcg ccatgggagc ctccgtaccc accttccctg tgcagtcact cccccgcagt    39000
ctcctgctca gaccctcctc acccccccagg ttcaagcagc ttctcctgac ccaggcagac   39060
aagttctctc cagctgaggt gaggctgccc agcccccttca atactcatcc ccagcacctt   39120
ctctgggcct tcacccatga cccagagccc agtaccagtg aggcagttgc tggaagggtg    39180
agccgagggc ccttctggag gaggtgccat ctctgttgag acctagaggg taaagatgtg    39240
gagtcagaaa agagggcagg gtgcgccagg cagggagact gtgcacagac ctgggggaa     39300 gtggataggg agaggtttcg tacactcggg gtgggcctgt gcctgtggct ggaggggcgt    39360
cctttgcctc ttggcccaca tttgcactga ctcctcactc tgcccagagt cagccaagag    39420
aaaaacatta acccagagtc tggggtctag ggttgaaaag ctaaggcaaa aagcacagat    39480
gcagggggca gacagaaagg ccacaggact caggtgaggt ctctgccggg ctgggccagg    39540
agccagggga ctgccactca ccagtgtccc ctgcaggtgg agcagatgtt cgccctgaca    39600
cccatggacc tggcggggaa catcgactac aagtcactgt gctacatcat cacccatgga   39660
gacgagaaag aggaatgagg ggcagggcca ggcccacggg ggggcacctc aataaactct    39720
gttgcaaaat tggaattgct gtggtgtctt gtctgtgaca gatggttgg ggaccagcca    39780 agggggatcc cagggtctca gtgcgcacat caccatgatc atggccacca tctacctcct   39840
gggagctggc ccctcgccag ctcaccttga ttcactccca tgatgccaag tgaagtgtga   39900
actatgatca tgcctagttt acagatgagg acactgaggc ccagaaagtg tgagcatctt    39960
accaaggcca gccctctaga agaggagatg gtgggattta caccacctcc accaagccca   40020
ggaatgagcc acaaagtggg cactgcccag ctacttgggg ctgtgcagag aagaggctgc   40080
ttgctgggca ctcagcaaac tctgcccaac agcccagcgg gtgggcagca gccctgggac   40140
ccccacaccc aaccacacag cctccctgg cccactgctc gcacccatc tcaatacact    40200 ggcttgggtg cctccctgca tgggccctttt gtgaaaggca gagaggtacc catttgaaac   40260
acaaccagct tctcattgca aatacaggca aggcactaag acatgaggaa catggacacc   40320
aaagcagggg ccaggtaaca tgcaaatttc tagaggaaat gcccagaacc tggcatcatg   40380
cctcctgagc ccctcatgcg ccgtgagggg taagagggtc agacagctgg agtgtaggga   40440
gacgacttct caggagagaa tagttagtgc tcccgtcacc cttcatctga aacccaaga    40500 gctagaggag aaagtgatcc tcatgagtac cagaggagca gcagggagaca tccaaagcac   40560 cagagagaga aacagagaca gagagacagg cagtgacagc tcaaacctca gccagatcca   40620
gagcatacaa agtctcctgc ctacaggaca gcccagtaag agctctcagc ttgcctcctt   40680
cccctcccac aagcccctgct gcaatccctg tacctggggg tcagtgggaa ggaggtgagc   40740
gagaaaggag gggcacccct tcctgaaggc cccaagagga aaggcgtttt cacccagaca   40800
ggtgttcagt tttgatttta tctggcgcct ggcaatttaa ttactaaatt gaaacttgag   40860
actttctgga attatggcat tttctgttgc ttagagagat tacaaaagtc acgaactgcc   40920
tgagtttcca tcctgaaagc aggccaccag cccactccac tgaccatgct ggaacagtgg   40980
atgaacaaaa tcaagtacca ttaggattct accacatgag tctgcttgtt caacaagctg   41040
atttcataaa gtaagggatc atgttataat ccaagctcta caggggtaaa ttgtgaaaga   41100
ctaaaatgaa ccaaaaagat cataggtgtc cagttatctg atttgatggg gtgtctgaac   41160
cttttgttat ctttgagctg tttcaaaact ctctaaatta ttattattat ttttgagaca   41220
gagtctctct ctgtcaccca ggctggagtg cagtggcatg atctcagctc actgcaacct   41280
```

```
ccacctccca ggttcaagtg attctcatgc ctcaccctcc caagtagcta gtattacaga    41340
tgggcacacc ttgcctggct aattttttgta tttttaatag agacgtggtt tcaccatgtt   41400
agccaggctg gtctcgaact cctgacctcc gttgatccac ctgcctctgc ctcccaaagt    41460
gctgggatta caggggtgag ccaccgtgcc ctgccacaac tctaaattat aactaatagc    41520
aaggcaatgg ttcttctcta ttaacgtgca aataaatgtt gtccagtgga agcacaactg    41580
atttttccct tctctgtgga agaagccaat tttgcatcta ttaagcaaat tcatctgggc    41640
attcctaacc gtctacacat gcaccggctc tttgaattct tctctgaacc aggcccagga    41700
ataagccaca agatgagcac tgcccagctc cttgggctgt cacatcttat tgattcccac    41760
atgaattcac aagtaaataa aatatttggc ggttgttcac ttagtatgca agtcaatatt    41820
ttgctttaaa aatattatcc tttcacactc ctgatatagt tgtctgataa ggttagtcct    41880
tcccacacca aaactgcctg tattagtgtt gtttggaata aactgagggt agaatgtata    41940
tggtgtgtgt atgtggtgtg tgtgtttgtg tgtgtgtgtg tgtgagagag agagagagac    42000
aaaagagaga gacagaagga tagagagaaa cagatgggca cagacccagg acatgagttc    42060
agcctacact gaccaatatg acagccactg gccacttgaa atgtggtgtg agttgggata    42120
tgccaaaagt gtaaaatgca cacaatattt tgaagatttc atacaaaaaa gaatgcaaac    42180
atctcattaa taacttttat atagatcaca tgttgaaatg ataatgttttt ggatattaga   42240 ttattactaa aattaatttc acctatttct tttcactttt taaatgtggc tactagaata    42300
tttagaattc cataagtggc ttgcatttct ggctttcact cctgttggaa agcactgagt    42360
tagactgtgt agtacgtcta tttaagactg cagtttccag gccgaacacc gtggctcacg    42420
cctataatcc cagcactttg ggaggccgag gcgggcagat cacctgaggt caggagtttg    42480
agataagcct ggctaacgtg gtgaaaccct gtctctacta aaaatacaga aattagccag    42540
gtgtggtagt gcatgcctgt agtcccagct actagggagg ctgaggcagg agaatctctt    42600
gaacccagaa ggggaggttg cagtgagcca agatcaagcc actgcactcc agcctagatg    42660
acagagcaag actccatctc aaaaaaaaaa aagtagaata aaaataaata aataaataaa    42720
gactgcagtt tctgggagac tctgaggcag gcattagcct tctctgcaga gagtacttgc    42780
agcagggagc agcagttttg atgtcctcaa aaggagccaa tttcatttgg gtagggttgc    42840
ctctgagtat tctagcagta cagacagaaa ggagagaagg ctgtttccag aaagcagaga    42900
tcatacgaat tacttgtgag accaaacttg ttcctcaggt gaagctcagg catcccttat    42960
gtggagtgtc taacagtcta cacctgagga tgttggacat aaggggggtgt gaggtgggca   43020 tggctgggga gagctctggg aggggaaaaa ccagctccat gttgtccacc cactgaaagg    43080
aaagctccct ctgggggagg tagatgcccc ctggccaggc ctgcagggcc ctgctcactg    43140
tgagccctgt gtggtcctgg cctgggtccc accagccatt gccaggcaac agctcccagt    43200
tggaaaacag agcaaggctc cctcttagaa aaaaaaaaa gaaagaaaga aagaaaaga    43260 aatacaacag gtaactaagc atgacggctc acgcctgaaa tcccagctac ttgggaggcc    43320
aaggcagagg attgcttgag actgggaggt tgaggcagca gtgagccagg attctgcaat    43380
tgcactccag cctgggtgac aaagtgagac cctagtaaaa aaaaaaaaaa tagagacaga    43440
gaaagaaaga catgcaacag ggccaggcgc agtgactcat acctgtgatc ccaacacttt    43500
gggaggcaga gaagggagga ttgcttaaga ccaggagtgc aagaccaacc tgggcaacat    43560
ggcaaaaacc catctcttca aaaaataaaa aaattagcct gttgtggtgg tgcgcaccta    43620
tagtcccaga tattcaggga gcttgaacca ggtccaggct gcagtaagcc atgatcgtgc    43680
```

```
cactgcactc cagcctgggt gacagagcga gaccttgtga gaaagaaaag aaagaaggga    43740
aggaaggaag gagggaagga gggaaggagg gaggaaggga ggaaggaaga atataggacc    43800
caaaggccta aatgcccta ctgtgcccca gttctgcgtg actcaggacc agcctcctcc    43860
acactcccac caccacaacc ctgcacccta cttgttcctg ggggcccaa ggggagcctc    43920
accagaagcc tcctcataaa cccactgccc cttacctttc ctgtctttct agaagcctca    43980
gaagccttgc cactctaagg acacctccat ctgagccaag gcgctcgctc cagatgtccc    44040
agagctcctg gtcctgggtg tccctgccac acaaccccc atggagccct gctctggctc    44100
aagcccctg actgtgcatg agcaggcctg ttgccctcac tgggactgtc cagagccttc    44160
ccatctctct ggagggactt ccatcagttt ctgccccttc tcctctgcca agaactcacg    44220
ttcagtctga tagcagaaga atcatctggc accctcctga atggaaccca gagtacctcc    44280
tttgtggacc ggtctctgga ttttccccac tctctcccct cagccatgct gatggcagag    44340
aaggtaagaa cttccagccc acttctctgg cgagggaac ttgtcatctg ggtctgcaga    44400
gaaggttcca ccttatgctc atagtacatt atctttacta tgtactagga tatcacattt    44460
aaaaggacaa aaaaggccag gcagtggctc atgcttgtaa tcctagcact ttgggaggct    44520
gaggcaggtg gattacctga ggccaggagt tcaagaccag cctgaccaac atggcgaaac    44580
cccatctcta ttaaaaatac aaaaattagc tgggtgtcgt ggcatgtgcc tacaatccca    44640
actactttggg aggctgaagc aagagaatca cttgaaccca ggaggcagag gatgcagtga    44700
gctgagatcg tgccactgca caccagcctg ggcgacaaac cgagactcca tctcaaaaaa    44760
taataataat aaaatacaac aaaataaaag aacaaaaaaa aagaaatgta aaatacttga    44820
aggggcttgt ataacattaa taggattgac agtatctgct ttccaggctg aagtgattca    44880
ttcattattc tagacgtctt tagtcctttg caatttgtgg taattaggct tttcttttta    44940
acattaaaaa tatacaaaaa taaaaggcaa aaaaagcatc atcccattag tctgaccttc    45000
ccctcctcca tccctgcccc aacaccctga agaccctgga tgcaaacaaa ggcccgaggg    45060
agcctcttcc ctcgcagtgc aggcctcacc tggggctcag agtcagaatc tgcattttat    45120
tccctaggac aaccctctagt cagggcagag gccggctgtg ctgcccaagt gccctaaccc    45180
tagctttgag gcaccagaag ggcaaatgca aattaaaaat gagaataagt ttattctcct    45240
tggtgaaaaa aaaaaaaaaa gactttcccc tctccttttt ctttagaaaa tctatcattg    45300
caagttcctt cctggacttt ttttatgtag atctgttcaa aagctaaata agcctctttc    45360
aagtttcaca tcccaggaat gtctccttaa ggacctagga gccaccattt gaagtgtaat    45420
caccaaggga gatacatcct tatctcccag tttccgtggg caaggggag cctaacttta    45480
gcccggtgcc tagctcaagt tgcaaacaca cttccagtct taaaggaatg aatttattt    45540
ttttccttta ggcaaaccca ggtagccacc acagttacct ggggattcac agagaactgt    45600
gtgtgaccac tggtgctgtc aagtcctctt acctgagcac ctgtgacgtt tcccttgaga    45660
acgtgtacgg gatgggttgc acctggttat atacaagcgt gagacttctt tctgcctttg    45720
taatttatta gcagattatc tgtgatgagc atcgcaatct gtttaatgcc tattcaataa    45780
ttaaattttt ctttctcttc ttttgtggaa aggttttctg cattggcagg agattttgt    45840
tttcgattat gtccccaaca tgcctgatgt tccacccctc aagagcctca gccttgccca    45900
ggagggcat gggggtgagt ggcctctccc acagagagtg ctggccaagt tggcccaggt    45960
gcgcagcaag ggctgctgcc                                               45980
```

<210> SEQ ID NO 7

<211> LENGTH: 18999
<212> TYPE: DNA
<213> ORGANISM: Homo sapiens

<400> SEQUENCE: 7

```
ccctcctcca tccctgcccc aacaccctga agaccctgga tgcaaacaaa ggcccgaggg      60
agcctcttcc ctcgcagtgc aggcctcacc tggggctcag agtcagaatc tgcattttat     120
tccctaggac aacctctagt cagggcagag gccggctgtg ctgcccaagt gcctaaccc      180
tagctttgag gcaccagaag ggcaaatgca aattaaaaat gagaataagt ttattctcct     240
tggtgaaaaa aaaaaaaaaa gactttcccc tctccttttt ctttagaaaa tctatcattg     300
caagttcctt cctggacttt ttttatgtag atctgttcaa aagctaaata agcctctttc     360
aagtttcaca tcccaggaat gtctccttaa ggacctagga gccaccattt gaagtgtaat     420
caccaaggga gatacatcct tatctcccag tttccgtggg caaggggag cctaacttta      480
gcccggtgcc tagctcaagt tgcaaacaca cttccagtct taaaggaatg aatttatttt     540
ttttcccttta ggcaaaccca ggtagccacc acagttacct ggggattcac agagaactgt     600
gtgtgaccac tggtgctgtc aagtcctctt acctgagcac ctgtgacgtt tcccttgaga     660
acgtgtacgg gatggggttgc acctggttat atacaagcgt gagacttctt tctgcctttg    720
taatttatta gcagattatc tgtgatgagc atcgcaatct gtttaatgcc tattcaataa     780
ttaaattttt ctttctcttc ttttgtggaa aggttttctg cattggcagg agattttttgt   840
tttcgattat gtccccaaca tgcctgatgt tccaccccctc aagagcctca gccttgccca   900
gggagggcat gggggtgagt ggcctctccc acagagagtg ctggccaagt tggcccaggt     960
gcgcagcaag ggctgctgcc caaaggctcc ctcctggttg gcatgggtcg ggaccctgtt    1020
gtgttgtgtt ttcgctcttt ttcgtagagt tcaaggggt cctgctatgt tgtccagact     1080
ggtcttgaac tgacctcaag ggatcctctc gtctcagcct cccaaagtgc tgggattact    1140
gtgcccagct ttgtgttgta ttttctgatc ttatcctgca acctcttgag cccccaacct    1200
gggcccagt tcctgctgtg ccccagcctg ccagccctct ctctctgcat attctttctt    1260
tagctgagtt aacaccactg ataaggttaa agacaggctc ttaaatttct gccctggcat    1320
gagaaatatg tgacccacat gcttctccag cttagctgtc cagtgtaact gtcagggact    1380
gatgggcgcg tgctggccca cagcccacct cagtcctgac cctccctgac aggctgagag    1440
aggccccagc ctgaacctgg actcccccat gttctgatat tcctgcacaa gagtgcagag    1500
gcctggttaa gctggagaaa cataaggaat aggtaggtct gcacacactc acctcttcct    1560
ttgcagtgaa ccttctagaa tcttctagat ggaaaagctg ggggtgtgga ggtgtaggga    1620
taggacagct gggggaggcc ttggccaagg tcaaggagta ggcccagtct ccctctctgt    1680
gtgcctgtct gggactcggt ttcctgtctg tgaagcaggg ctggacggga tattgacagc    1740
acctgatggt cattgagctc ctctgcccca ggcactcagc tgctgggcac agtgcacacg    1800
tggcagtccg gtgccctctc acgctccgtg atgactgagt ctgtagttac acccctggcc    1860
tcagaataaa gactacactt tctgcctccc tcactggcag gtatgactag gtgtggtggc    1920
agttttctcc ttaagagaca gatgtttgtg cctccctcca acccgctggc taacacctag    1980
ctggcacaca gcctcctggg gctatgaaga tgagggccac agccacaggg tgggggagcc    2040
gtgagctggg tctggctgcg tctctgacat atgggggcat cacacatcac ctctacctcc    2100
catcgaatgc tacacgaaga gaacaaactc cacctgatgg aagctgctgt tgtttgaagt    2160
cttttcatgct cacaacagaa cctaacccca accaatacag tatgagtatt ggccccacgt   2220
```

```
ggttaagcaa gctgtccaag gttacacaca gctgggaggt ggtggagctg ggtttgagcc      2280
tgttattgac ctttgtgcag acagacctca gagcagagca caaggcagca aggctgtggg      2340
tctggggctc cctctccagg agaatcaact ggctgcacac agcctggaga gcccatgggc      2400
aacctgagtc cttgcacctg gaagtttctg tgtcccacac atatccagga gcttaaaatg      2460
aagatgtctg aattacccaa cctcttgata gcaccaaccc aaccttccca gcctcctctt      2520
ctgaggtcag cccagagcaa gccccttgca aagctgattt aactcagaac cactgggcat      2580
acccacaggg cagtgaccct gcagccctcg atcaaatgtg cagatggact gggggtggg       2640 ctggtacccc agatggcctc attctcccag ggttgcagag cccctgaaag ccacagccct      2700
gtgtgcacac cactggggag tcatcacagg atacttcaag aattcagtgc caggcaaggt      2760
ggctcatggc tgtaatccca gcacttcggg aggctgaagc gggcagatca cctgaggtca      2820
ggagctagag accaccctgg tcaacatagg gaaacccat ctctactaaa aatacaaaaa       2880
ttatctgggc gtggtggcgg gtgcctgtaa tcccagctac tcaggaggct gagaccggaa      2940
aatcgcttga gcctgggagg cagaggttgc agtgagctga gattgcactg ctgcactcca      3000
gcttggggga cagagtaaga ctccatctca gaaaaaagag ttctgtgtat catttaatgt      3060
ggagatcctc ccatcacgag gatgaggctg tttctctact ccccagatct gggctggcct      3120
gtggtttgtt gacctcagcc ttgtagttct cactttcctg gaacctgaat gccaccacgc      3180
gacatccata agacaaagcc caggataaaa gatcacttgg agagacaggc ctggcctggc      3240
accaccccgg ctgaggctgg acccctggga aggagactct gatggacctc cagacccagt      3300
caaatgacca cttccaaggt caggcaagaa gggacaaaga gccactggct cagcccacag      3360
catctgagaa ataagaaacc gctgcatttt ttgagccagt aagatttgac aggtttgttt      3420
tgcagcaata gatgagtggt acctcatctt agcccatgtt ctgatgaaga caaacagtag      3480
cattgacaaa gttttaagaa aagttaacca aaaactggga ttcctttctt cattttgacc      3540
ctttgttaca agaaacagag gcccacccca ccagactcac tgttcactgg tccctgagtg      3600
cctgtgagtc tcagtgggag ttaccttgag accagccctt ctgagtggag ggtgctgggt      3660
gctgaggtca agtcgagctc agtccaggct aaaaggagag cagctctggc caggctgtca      3720
gggctgtggc ctccccaaga acctcctacc ctggcccctc caggctttgc tgctatggtt      3780
gtgtgagggg agttgctgtc ccagcattct ggccccttg ccccccagccc ctccctgacc      3840 tccacgggct tcaggcctca gtccagagtc acctcctcta ggaagccatc ccccagtgca      3900
agtctgggca acattcctcc ttgcctggcc cacctgctca ctctcatgct atggctttct      3960
gtaagcaaac acaaagatag gaacaactct gtccctggca cagagcagat gctctggcaa      4020
tatctcatga gtgaatgaag gcacatgaca aacctccaga cctgtggaga ctgaaggctg      4080
agagccttta tagatgctgt ggggccgagg agtttgccaa ctacagcagg tcatgcccag      4140
aggtttctct ctgggtagca aggtgtgtct cccaccaaag gccattggca tggggcccgc      4200
cctgctgacc cgaggcagtg cacagcagag gccagatgca gtgagaagga gcctctcctt      4260
ggcctgctgt ctgctgccat gcctgtgggg gcgtggacac aagtgtgtgg catagaaggt      4320
ggtgtggcag gtgagaggtt gggggtgtgt atgtagcagg tgtctgtgtg tgtatgtgca      4380
tgtgggggtg tgtgtgcatg catgtgtgtg tgtgcatatg cacgtgtgtg catatgcatg      4440
tgtgtgcatg gagagagaag acctcctctt tctggcccct ctcctagctg ccccccctccc      4500 tcctgctgcc aacacactgt caaccccttca ctgtctttt ccttgggact cgttgatctg      4560
tctctaccat cccaggtgtc tggagcagcc tctaaccttc catctgccaa ggtacttcag      4620
```

```
cccacccct cccagctgtg gaatgtcccc taggatgtgc cactgacaca aagagccaca    4680
cagctccaaa atagaatatt atctaaccca ctgctccctt tgctgtcagc aacacctcca    4740
ccatgcttct cccaggaccc cccttgaact ctctgcttcc tccctgaggc caaaggaaag    4800
acaggaaagg ggccaccttc ctgtccttgg gtcccacaga gatgtatcct tgtaatgaaa    4860
cctactttat gcttgagttg tatccagtta gtttctgtgg cttgcaatca agacccacac    4920
ccacctcaac ccaggctcta gagagtagac ccttgttttt gcctggcttg ggtcgacctg    4980
gcacctgcca gggtcccagc ctctgagtca gcccaccttg ccctcatcgg tgccacctcc    5040
aggcggctgt acatagactc tggcttctgc cctggcctgg cctctgggaa ctgcagctgt    5100
ctgcttccat cctatgtgga tggtgcctga aagtgaatag ggatcagtta ccagcccagt    5160
atctgtcccc ttctcaatag cactgattcc tatggggaac tgcttttctt ggactatgta    5220
tgggtttggt gggagggtag ttcctgtaac caaccctaca gggtgtagga acctagactc    5280
tcagcaacat aacaggcagc aggctcccaa gctaagtctg gccagctggg ccacctctcc    5340
cagattctgt ttcatgagag catcatccaa gagcagtggg aacactgggg acggtccagc    5400
ctaggactgg tatgcagatc agagaatccc agatagaagg tgattgctgt tcttccagtt    5460
tcttggccct ccagagcaac catacttccc atctgcccca aaacctgatc ctccaaactc    5520
ccaccatttc tgtgcatccc caatatctaa tagatcaact gcctttcatt tacatttgtc    5580
acaaccaaat gatacacctg cccttcaccc actactgaac tgcagctggg ttagtccaaa    5640
ttcagggccc acgtgtcatt tcaagcctgt cttgaataat gtacaccttc ctgcaatgtg    5700
aggatggcca ccaccttggt cttatacccca cgggtgtcct gagctacatt tctcataatc    5760
aaaaataaac tcaacacatc actccagcct gagcaacaga gcaagacact agctctaaaa    5820
ataaaaaata aaacaaaca aatgaaaaac ccagcaaact tggggaaaga ggaagcacct    5880
gatttccaga gtttccacat catgagatgc aaatgtccag ttttcaacaa caacaacaac    5940
aacaaaaaaa aaatcacaag gcatacaaag aaataggaga ctaagaccca ctcaaaggaa    6000 aagaatataat aagcagaagc cataccagag gaaaaccaga tggctgactt actagacaaa    6060
tactttaaaa caactgtctt aaagatgctt gaagagctaa aggaaaatgt gaacaaagtc    6120
aagaaagtga tggaacaaat ggaaattcca ataaagtgat agaaaacttt ttggagtttt    6180
ttttcttggt agcaaaaaat tatgaagctg aagaatacaa taaattccct agagggcttc    6240
aaaggcagat gtaagcaaac ttggccaggt gcagtggctc atgctcataa tccagcactt    6300
tggaaggctg aggcaggagg attgcttgag cccaggagtt tgaaaccagc ctgggcaaca    6360
tagaaaaacc ctatctttaa aaaaacttat ataaaattta aaattataa aatttattta    6420 aaaaatcagc aatttgaaga ctggacaggg aaattatcaa atttgaggaa cagaaaggaa    6480
aaagatggaa gaaaaataaa cagagcctaa gagacctgcg ggacaccatc aagcagacta    6540
atacccattg tggaaattcc agaaagaaaa gagagtgaag gaccagagag attattagga    6600
gaaataatgg ctgaaaatgt ctcaaatttg atgaatgaca tgaatatgaa cattcaaaaa    6660
tctcgacaaa ctccaagtag gaaaaactca aagatactca tactgagatt catcataatc    6720
aaactgctga aagccaaaga caaggagaca atatcaaaag ctgcaagaga aagtgactc     6780 atcacataca agggatcttc aaaaagatta tcagatatct tggctgggca cggtggctca    6840
cacctgtaat cttagcactt tgggaggccg aggcaggtgg atcacttgag gtcaggagtt    6900
tgagaccagc ctggccaaca tggcaaaaac ccatctccat taaaaataca agattggtg     6960 aggcatggtg gtgcatgcct gtaatcccag ctactcggga ggctgaagca ggagaatcac    7020
```

```
ttgaacctgg gaggcggagg gtgcaccaag ccaagatcgt gccaccactg cactccagcc    7080
tgggtgacag agtgtgacct tgtttcaaaa aaaaaagaaa aagaaaaaga aaaaaaagat    7140
catcagctat ctcatcagaa acctcagagg ccaaaaggca gtagattgat atattcaaag    7200
tgctaaaaga aaaaaataaa tctgtcagct gagaatcctg tatctgtatc tcacttaacc    7260
attattttaa aataagggaa aatgaagaca ttcccagata aacacaagct gagggagttc    7320
attatcacta gatctgccct gcaaagaaag ccaaagaaag cctttcagga tgaaatgaaa    7380
ggatactaga cagtgactca aagctgaata agaggccag gcatagtggc tcacacctgt     7440
aatctcagca ctttgggagg ctgagatggg cggatcacct gaggagttgg agaccagcct    7500
ggctaatatg gtggaacccc atctctacga aaaatacaaa aattagccag gtgtggtggc    7560
acatgcctgt aatcccagct acttgggagg ctgaggcaag agaatcacct gaacccagga    7620
ggcggaggtt gcagtgagcc gagattgtgc caccgcactc cagcctgggt gacagagtga    7680
taccctgtct caaaaaaaaa agccgaataa acgaataaag atctcatcta tggccgtacc    7740
accctgaatg tgtccaatct cagaagctaa gcagagttgg gcctggttag tacttggagg    7800
ggagaaataa cggtctatgc taaaggaaaa ttcaggtgca attaaagtaa aattaattat    7860
ataaaagaga atacattaaa agctagtatt attgtaactt tggtttgtaa ttccaccaag    7920
tggaatttgt tcctgaaatg ctagaatggt tcaacataaa aatcaataaa tgtaatagac    7980
cacattaaca gaaaaaaaac ccacacggtc atctcaattg atgtcaaaaa agtatttgac    8040
aaaattcaac actcttttga agaagaaaaa agctcaacaa actaagaata ggaggaaact    8100
acctcaaata ataaaatcca taggccaaat ccccaaactc acagctagca acatatttaa    8160
tgctaaagac tgaaagcttc cccttttaaga tccggaataa gacaaagatg cccactttca    8220
ccacttctac tcaacatagt atgggaagtt ctagccagag taatcaggta agaaaaaaga    8280
aataaaaagc atctgaattg gaaggaaaa agtaaaatta tttgtttgcc caatacatgt     8340
acaatgtttc aggtgaaggc tcagaacagt acaaccttac cagcaagagt cctgctgtct    8400
ctgtgtgaat cccagctatt actcactagc tacatgatct ctcttgccct ccctgcctca    8460
atttcctcat gtgtaaagtg ggagaaaaat aatagttcat gcttcaaagg ttttttgttt    8520
gtttgcttgc tttgagacag cgtctggctc tgtcgctcag gctgaagtgc agtggtgcaa    8580
tcttaggtca ctgcaacctc agcctcctgg gcttaagcga tcctcccacc tcggcctccc    8640
aaagtgttgg gatacaggcg tgaaccactg tgtctgaccc aaaggattat tgaggagca    8700 gatgaattaa tgtgtcataa cctcaaagca gttgcaaagg cgtttaataa ttaaaatatc    8760
acattttaaa ttaaaatata aggctgggcg tggtggctca tgcctgtaat cccagcactt    8820
tgggaggctg aggtgggagg atcacttgag cccaggagtt ccacactagc ctgggcacca    8880
ttgggagacc ctgtctctac acacacacgc acacacacac acacacacac aaacttaaag    8940
tagccaggcg tggtgctgcg cgcctgttgt cccagctact cggaggctg aggcgggaga     9000 atcactggag cctgggagtt cgaggctgca gtgagccgag atcgcaccac tgcactccag    9060
cctgggccac agagcaagac gctgcctcaa acaaacaaac aaaacaaaa attaaaatat     9120 taagtaataa ttaacgagtg ttaatatcca ctcgttgtgg agacaagacc tggacttagg    9180
aaacaggccc agggaagtag cagaacagta gcgctagagg acgcctggga gaatcagcgc    9240
gcggcgggaa gagcccggga agcttagtgg ggaagcgtct cttgatgggg tgaggaattc    9300
tataaattag tggagatgga aaaaaaaaaa aaaagtatt cccaaagtgg gagacagcac     9360
tcagaaagac gtggtggtaa gaacgagtat gagtaacggg gacaacgagg acactggaga    9420
```

-continued

```
ttggggagtg ttgggctgga agctggtgtg cagctgtggg caagctaggg aggaccccga   9480
aaccgccaat gcgtttcccg gacgcagacg ctggcaggac gggaggaacc ccgagacccc   9540
gcgccatccc ttcaggaaga gttacttctc cccggccaag ttagtgggcc ttgggccttc   9600
tttctgttgg gatcctcctc gcgtgtcgcc atcgctacaa gtgggcagct ctgcggggaa   9660
agctgggacg ctgggggctt caccaaggag gctggcggcc gaccactggg aggtctggcg   9720
gggtgacgac cactgggagg tttgggcagg gcctgacggg gtgacgcggt cagcccactg   9780
gaggccgaca ccccccgtca gcccaacccc tgcacgcgcg ccgccaaacc aaagacccgc   9840
ggcgccggcc tgcgagcccc cgccccgcgt tgcccaggaa accgagggtg tggctccgcg   9900
ttctctgggc gtcccaggga ctgggcgcac agtggtcggc gggatgaggc gcctggtgac   9960
ggacggggcg aggagggcag cgattggtga gattaggcga tgggcgggga agccgcgcgg  10020
ggattagcga gttgcggcga tgggcggggc aggcgcgcgg ggattggcgg gatgcggcgc  10080
gccgcgcgtt gagtgggggtc cagggaaacg gggtcagctg ggggtggcag ttccaggccg  10140
cgaggccggg ctcctgggtc ggtgggctgg tgtcttggcg gacgtccgc agctgccgcg   10200
tggatccgag ccggggcacc cgccgtgact gggacagccc ccaggcgct ctcggcccca   10260
tcccgagtag cgcggcctgg ctgctgccgc catcaagcac gttcgagcca aaagctccta  10320
acgagtcact cgttagacac gtgtgcggag cctgtgtccc aggccagtgc tgtcccgtgg  10380
agatagattg caagccgcta gggaatttttt taactttcta gtaggtgtac gaaaaaagta  10440
aaacgaaaca aatcaattgg agtaaatcca taaatatatt caaactatta tttcaattgt  10500
atgtgaaaaa attattggga tattctttgt actattctta gaaatccatt gtgtgtccaa  10560
cccaaacatc acagttggac tcaccacatc tcctgtactt cgtagcccta ggtggctagt  10620
ggcataagac acaaaaatct cagctctcct ggagcttatg gtctagttgg agcaggcaga  10680
caatacattt aaaatataca gtttgttaga aggtaaatgt tgtaaacaac aataacagtt  10740
gaagtactgg ggagagttgc agttgtaaat cagatgggca gggcacaagg taacatttga  10800
gtaaagatgt aagaacttga aggagatggg caagtgagct ctataagtat acgggagagg  10860
ggcaagcaag agttcagagg ccccttgctg tggggaggga tccaaggtgg aggagtggga  10920
accaggaggg gagaggacca gtggagcaga tctcataggc agttgtaagg acttggggcc  10980
ttattcaatg aaatgaggac actttggaga gttttgaaca gagcagtgac tgatttatgt  11040
tttggttttg gtttagttct attattattt aataataggc ttattatttc acagaagttt  11100
tatttaataa ggcagacctc ttgtctggaa atgagacagg tgccggagag ctggatggag  11160
gcagatcggg aattccattt ggggcaaact gaacttgatt gagaccctgg tagttgtcca  11220
gatgaaacag gacacctgag tctagggttc gggaagaact ccagatggga caaacactcc  11280
tagctttcct tttctctttt tggatgaccg ctacagggtg agacatcggt atccaggcac  11340
gataaatttc caagtggaca caatgtctgg tgtcaactac agctgttctc cttctttttcc  11400
cagtatcctt tgggtgcagt gagacaccag gagagctgct gctttggggg atggacaggg  11460
gcagcaggaa tgcctttgtg ttttcgcagt gaacctcctt ggcctgggcg aagctgtgtg  11520
gaccaagcaa gtcaggagtg tggccatgtt ttctgagcag gctgcccaga gggcccacac  11580
tctactgtcc ccaccatcag ccaacaatgc caccctttgcc cggtgccag tggcaaccta  11640
caccaactcc tcacaacccct tccggctagg agagcgcagc tttagccggc agtatgccca  11700
catttatgcc acccgcctca tccaaatgag acccttcctg gagaaccggg cccagcagca  11760
ctggggtaag tgagagtttg ggaaggtgct tcccccacag catccctgaa cttagaagtg  11820
```

```
ttctgcaaga gaatgggaac agtttatcta attgatccca cttcctgtta ccttgggaaa   11880
attaacctct ttttccctca gtttcttctt aagatagtaa caaggattaa attaagtaat   11940
ttgtgggttt ggagttagtt ttagttcaga ggctggttgg agatgaggac ttagttctgg   12000
cggtgatggc gattacttca ctggcagagg aaaatggttt tcctatcttc agtgcagatt   12060
attcaggtat ttgcctgtgc tgtagccaga gagcccctca gtgtggcaag cctggcgcca   12120
ggcaccagga gccaagactg gtgaggatgc actctctggt ctcgagggga cccctctgt    12180
tcactcatgt ctgtttgcct ctcctcctgg ccccatatt tgctggccat gaattttcct    12240
gtcccttggg ccctctgtct ttcctaataa gtggcctgc ccaacacaac ccttgttctt     12300
tgcccccatt tcttccctgg tgatctctcc tgcagttgga ttactcttgg tggtgaagca   12360
gggacccca tctccccctt tgagtttatt tgagttttag gtgctgctgc attcccccat     12420
tcctaccact tacataagag tggctttcca ggtaattttc aaatccatct cctattatat   12480
ttttaaactg aggatttagt aggtgagacc aggtcttact catttttact gtccttggca   12540
ccaggcaaaa tggatctcag ccctagttgc acattggaat ccctggggga gctttgagaa   12600
gcccatctca tccatgcca agccaagatc aattctcgtt ataggcaggc aggagaaccc    12660
tgggcctaga aatctagcta gaacctcaaa ttcattaggg atatgtatta gtccattttc   12720
acattgctat aaaaaactac ctgagatagg gtaatttata aagaaaagag gtttaattga   12780
ctcacagttc ctcatggctg gggaggcctc aggaaactta acaatcatgg cagaaggtga   12840
agggaaagca aggctctttt acatgatagc aggagagaga gagcaagggg aactgccaac   12900
cattttaaa ccatcagatc gcatgatggc ttgatctcac tcaccatcac aagaacagca    12960
tgggggaaat ccaccccac aatccagtca cctcccacca ggtccctccg tcaacaccgt    13020
gtggattata attccagatg agatgtgggt ggggacacag agccaaatca tatcaggatg   13080
ttttctgttt tgtttacctg agacaaagtc ctgttcacct ctcctctccc acataatcag   13140
gggctccctc ctgcggctcc ggtagctttt cctcactttc ctttcagccc tcgggacacc   13200
ttccttggct cctttcagag ctcagttact acttgggccc aatgtcaatg ccaccttcta   13260
gattcttttcc ggcagcacct cctctggtcg cacatttctc ttccagttat tggagctgtc  13320
aaaaaagctc cccagtgatg gacgatagcg atttcactgt gctcacagac tggtcaggaa   13380
accaaacagc tgccacagtg aatgtgttga tagcagcggg gcagcagtag cactcgctca   13440
caggcctggt ggttggtgct ggccccacc ctgaatacct acatgtggct ctccatgtg     13500
gcctgtgcat cctcactgaa gctcagcctg tctctccaaa ttggtctttc cactccactg   13560
ttccccaaac ctgcccagac cttcctgctg taggcttttc ccttcacttg gcacactctt   13620
tcccttgtct tccatggcc ccatctaagc cccactgtca gctgaagtgt tatattcttt     13680
gaggggccac ctgaagccac cttgcaatga gggcctccgt tttctacctc agctcaccat   13740
ttgttcacag cacttgtcac tgtggcgagt tacttgtcta tggcctgttg tcgttctcct   13800
gcctagaccc agtgggctga gtgggggcaa gtgttggctt ttatgtccag ttttgatctt   13860
ggtgccagca cattgcctgg gtggaagcat gtcctactat cggttacagg gatgtcattc   13920
tgcccagtgc tcagggcat acacttggat cccagttgtg tgcccttgga cacattgctt    13980
aacctctctg tgcatcagtt gggtgataat atctactcct ggcacatttt cagcgttggc   14040
tgagttacat gtacagtgct taggccacct gggggagagt aagagtggga tacgtgagga   14100
tgtggagtct gttgcatttc tgtctgctgc tggcatcctt cttgtcttgt tttgagttgc   14160
tcgcctctgt ctgctcccta gggcgtagat ttgaggaata ttcctggttc ttcccaggca   14220
```

-continued

```
gcaggggctc aggctgtgct ggagtcagct aggctaaggg gctggtctgg catccgcgtt   14280
gtcctgtcac ctccttggtg ttttctccag gcctggatct gtgctgtgtg ggcacctgta   14340
ttcctccctc ctgccctcac tgattctcca tacctttctt ctcgagagtg ccaagcccct   14400
cccatgtgtt cttgttcata cctaggatcc cgggaagggg ctgggaaga cggtgcccag    14460 gtgccctggg taaacaaagc cacctgactc cacgggaatg gaatgggtgg aggggatctg   14520
aggtctgcat tttgagtatc tctggtctca gaggatgaag catttggtgg gggttggggg   14580 tgggggtag ggtggaagaa tctaaagtct taaagaaaa tggcagttat ttgtgggaca     14640
gggctgtgtt gagacttggc atgcttcttt ttaagagtca gtgttgtaat ttaggtataa   14700
gtgaagcagt actttgtatt agtttcctgt aggcgctgta acaaagcacc acaaactggt   14760
tgacttaaaa caacagacat ggccgggcac ggtggctcac gactgtaatc ccagcacttt   14820
gggaggccga ggcgggcaga tcacaaggtc aagagattga gaccatcctg gctaacacgg   14880
tgaaaccctg tctctactaa aaatacaaaa aaaaaaaat tagctgggcg tggtggcaca   14940
cgcctgtagt cccagctact cgggaggctg aggcaggaga atggcgtgaa cccgggaggc   15000
ggagcttgca gtgagctgag atcgcgccac tgcactccag cctggatgac agcgagactc   15060
cgcctcaaaa caaaaacaaa aacagaaaca acaataacag aaaaacacag acatttactc   15120
tctggcagtt ctgaggcca gaagttgaaa tccagatgtc agcaggattg gctccttctg    15180
aaggcccgag ggagggtcc ttcctggcct cctccctggt gttcctgggc ttgtggccgc    15240
atcactccgc tctgcccgtc ttcacactcc ctcttgtctg tgtgtctgtc tctctgttct   15300
catgaggaca cttggcatcc agggcccaac cacacccaga gtccctggtc tcctgtggct   15360
gactcacttt ttactgtcac cgtgaagtcc aggggtcct tgtacttgat gttctctcct    15420
ggcaaggcca gggccctgtg attggcctct catggagtgc tgggcagggc ctccatggcc   15480
tctgtcgggc gggggggcta cttcatctct gagtctgtac ccctcgtgtc ccaggcagtg   15540
gagtgggagt gaagaagctg tgtgaactgc agcctgagga gaagtgctgt gtggtgggca   15600
ctctgttcaa ggccatgccg ctgcagcccc ccatcctgcg ggaggtcagc gaggaggtga   15660
ggcagggtgc tacacagtgg ggccgccagg cagacctggc ctcccactag aacacctccc   15720
tggaggtggg gttgtgggga agcaggttca gagacaatgg actccagagg ggtgggggct   15780
gcggtgccag ctcactaaca ccagagcttt ggtgggctct ggccccaaga ttatacctcc   15840
tgtctctgca ttccagcaca acctgctccc ccagcctcct cggagtaaat acatacaccc   15900
agatgacgag ctggtcttgg aagatgaact gcagcgtatc aaactaaaag gcaccattga   15960
cgtgtcaaag ctggttacgg gtagggagcc caatgagagg atgtgggtga tgcaggtgaa   16020
gagcccagcg gtggtgtgtt agggatggtg tgagtgggga gcctgggggg agtgggggg   16080 tgtggcctgg gcacacgtgt gttcttgagg aggtaggtga ggctccaggc ggtcggaggc   16140
catcagattg ggtgagacct ggctgggaga tgggtctccc cacctccatc caagggcagt   16200
gactccagga agcaggcatg catcctggag tcctaggtga gaattcacca atgtggttgt   16260
ggagaactgg cttgttttgc ccgttgggt gactggaagg agtggtagca cctgggctc     16320 cctgctcagg cctgatgcca ctgctcccca gggactgtcc tggctgtgtt tggctccgtg   16380
agagacgacg ggaagtttct ggtggaggac tattgctttg ctgaccttgc tcccagaag    16440 cccgcacccc cacttgacac agataggtga gcagcagttc tcgggagctg gaaccagctc   16500
atggtcagtg gaatctttga gttgcaccta ggagggctg cctcccttct cggcaccctg    16560
gaggacccca ccttctcccg caggtttgtg ctactggtgt ccggcctggg cctgggtggc   16620
```

```
ggtggaggcg agagcctgct gggcacccag ctgctggtgg atgtggtgac ggggcagctt   16680
ggggacgaag gggagcagtg cagcgccgcc cacgtctccc gggttatcct cgctggcaac   16740
ctcctcagcc acagcaccca gagcagggat tctatcaata aggtatggag cccacctggc   16800
tgcattcagc cccagcccag gagcctgcaa gcctgtaaga ccctccttcc ccagggcgag   16860
tagggtaccc tgtgaggtct cgcaggtcgg tgggaagcgc cctgcagtga ctctggggcc   16920
tcctgcaatg gggctcctca tgcccaggcc ctcgctgagg atggtgggag gcttgaaggg   16980
agtgagggtc tatgggacaa caactgcatc ttccagctgg tggggctcta ctctcctctg   17040
agcctgggac tcgcctgggc ctgatggcct tctgggcttc tattccaggc caaatacctc   17100
accaagaaaa cccaggcagc cagcgtggag gctgttaaga tgctggatga gatcctcctg   17160
cagctgagcg tgagcgagct gggggctgga ggggtgatgg ggattgcagt cttcaaagct   17220
gccactgggc aacagaaggc aggcaggagg gcaggggag tggccggagt tggtgtaggg    17280
ggctccttcg gggccctgtg agctctccct gccctgtgcc ttccaggcct cagtgcccgt   17340
ggacgtgatg ccaggcgagt ttgatcccac caattacacg ctcccccagc agcccctcca   17400
cccctgcatg ttcccgctgg ccactgccta ctccacgctc cagctggtca ccaaccccta   17460
ccaggccacc attgatggag tcaggtagct ggcacagcca cacttcagtc tgacccagcc   17520
ttttgcctca ggaggcacaa agaagggagg ggagggaggg cccaggaagg tggcagggct   17580
gcagaggccc acctagcatc tgttccttct ctctggggca tccccacaag agcgccagat   17640
gagctctggg ctgaccacta tgggtggcac ccaaagccaa gagtcagctg agctttgcct   17700
tgcagatttt tggggacatc aggacagaac gtgagtgaca ttttccgata cagcagcatg   17760
gaggatcact tggagatcct ggagtggacc ctgcgggtcc gtcacatcag ccccacagcc   17820
ccggacactc taggtaacag gctcagccat acagggtggg agcagagggc caggaggcct   17880
ggcaggaccc tgaagtgcac agggtccccc tgtgggtttg cacttgccag cattgctgag   17940
aactgtctga ggagaagttc agaggcttgg cacctgctct ggaagctact ctggaatctt   18000
aattctaagg ccaatggctg cccaccccaa cgggcagcaa cagcagggcc aaggtcttgt   18060
gacaatgtct ggaggtgccc ctattgtcac actgggggtc tcctactggc ctgcaatggg   18120
aggaggggct gcagccccac atcctgtgca gagtgctagt gctgaggcgg aaccctcctc   18180
agagctgccc cttctcctct aggttgttac cccttctaca aaactgaccc gttcatcttc   18240
ccagagtgcc cgcatgtcta cttttgtggc aacaccccca gctttggctc caaaatcatc   18300
cgaggtaatt tttgtcttct gggggcccag gctgatttgc tgatttgctc tcacctgggg   18360
acaaggttca cagagaagaa aacctgcatt gtggagtccc cctggcccct gtgggatgga   18420
cagctgaggt cttctgcaca gctgccattt cactgtggga gccaagctgc ctcgccagct   18480
gggcagggac tggaacggct cccagcctgt gtgcctctca aggctaatct ctggtctcct   18540
attgtcactg ccccactgtg tgccaatggg gactcctgtt tatttctggc agcttctctt   18600
tgaggcagga cttacttgga acctacagtg ggtcctatgt gacttctttg caggtcctga   18660
ggaccagaca gtgctgttgg tgactgtccc tgacttcagt gccacgcaga ccgcctgcct   18720
tgtgaacctg cgcagcctgg cctgccagcc catcagcttc tcgggcttcg gggcagagga   18780
cgatgacctg ggaggcctgg ggctgggccc ctgactcaaa aaagtggttt tgaccagaga   18840
ggcccagatg gaggctgttc attccctgca gtgtcggcat tgtaaataaa gcctggcact   18900
tgctgatgcg agccttgagc cctgggcact ctggctatgg gactcctgca ggggtgccca   18960
cagtgaccat agcccatgca cccaccagcc ggtctccct                          18999
```

<210> SEQ ID NO 8
<211> LENGTH: 16161
<212> TYPE: DNA
<213> ORGANISM: Homo sapiens

<400> SEQUENCE: 8

| | | | | |
|---|---|---|---|---|
| cagcagggcc | aaggtcttgt | gacaatgtct | ggaggtgccc | ctattgtcac actgggggtc | 60 |
| tcctactggc | ctgcaatggg | aggagggggct | gcagccccac | atcctgtgca gagtgctagt | 120 |
| gctgaggcgg | aaccctcctc | agagctgccc | cttctcctcc | aggttgttac cccttctaca | 180 |
| aaactgaccc | gttcatcttc | ccagagtgcc | cgcatgtcta | cttttgtggc aacacccca | 240 |
| gctttggctc | caaaatcatc | cgaggtaatt | tttgtcttct | gggggcccag gctgatttgc | 300 |
| tgatttgctc | tcacctgggg | acaaggttca | cagagaagaa | aacctgcatt gtggagtccc | 360 |
| cctggccctt | gtgggatgga | cagctgaggt | cttctgcaca | gctgccattt cactgtggga | 420 |
| gccaagctgc | ctcgccagct | gggcagggac | tggaacggct | cccagcctgt gtgcctctca | 480 |
| aggctaatct | ctggtctcct | attgtcactg | ccccactgtg | tgccaatggg gactcctgtt | 540 |
| tatttctggc | agcttctctt | tgaggcagga | cttacttgga | acctacagtg ggtcctatgt | 600 |
| gacttctttg | caggtcctga | ggaccagaca | gtgctgttgg | tgactgtccc tgacttcagt | 660 |
| gccacgcaga | ccgcctgcct | tgtgaacctg | cgcagcctgg | cctgccagcc catcagcttc | 720 |
| tcgggcttcg | gggcagagga | cgatgacctg | ggaggcctgg | ggctgggccc ctgactcaaa | 780 |
| aaagtggttt | tgaccagaga | ggcccagatg | gaggctgttc | attccctgca gtgtcggcat | 840 |
| tgtaaataaa | gcctgagcac | ttgctgatgc | gagccttgag | ccctgggcac tctggctatg | 900 |
| ggactcctgc | aggggtgccc | acagtgacca | tagcccatgc | acccaccagc cggtctccct | 960 |
| cctcccatc | cctgacacct | cagaatgtga | gcagtccgtg | ccatgagctt gttttattgg | 1020 |
| agtgaccttg | gctccctccc | tctgccccta | ctccaacact | gcagcaaccc catctcttac | 1080 |
| gagactggca | ggtggagcag | gagcctctac | acagcctctg | gctcttaggt cccagtcatg | 1140 |
| tttgcacccc | ctcaaagggg | caggaccagc | ccttcctttc | agtgtccata ccaggggcct | 1200 |
| tccatgtgct | gatgggtgat | gtgactgtgg | tcagcaggct | tgggaagtgc tgctgctgta | 1260 |
| gcttgagttg | ggctggggtc | ttggtaggac | gctgatctca | gaagtcccca aagttcactg | 1320 |
| tgtaggtctc | tactgttgtg | aaggggaatg | cctggccagt | ggctatctcc tcctctttct | 1380 |
| cctcctcctc | ctcttcctca | aactcgggtt | ccagctgggt | ctcgaactca ggctccaact | 1440 |
| gggtctcaaa | ctcgggctcc | accttggtcc | caaactcggg | ctccacctcg gtcccaaact | 1500 |
| ctgtcaccac | ctctgtgtag | gtctcagtct | ccgactcctc | ccagccagcg gtggttggcg | 1560 |
| gtatgaggcc | ccagggctct | atggtagtgc | tcagggtggt | ggcaggggca gggggcagcg | 1620 |
| tgggaggcac | agtgtggggg | cctagggtgg | tggtggcgtt | gaggcgccgc agccgcatct | 1680 |
| gtgcccgaag | ccgcaggcgg | tgttgtaggc | gtcgctgctg | caggcgtcgc tgttgggggg | 1740 |
| tcatagggcg | cgatgggtct | atgtgtggga | taggccggtt | cccgttcatg gccatgatct | 1800 |
| cccggatgcg | cttccagttg | gagcgagcca | ggatgaagtt | gcactgagtg gccccgatgt | 1860 |
| catagtcaac | attgcaggtc | ttggcgctcg | gggtgtagcc | ctccgcgtgg gctgtcacgc | 1920 |
| ggtactcacc | cgggttcaag | attcgccagt | aatcaccacc | actggctgcg gagggagaac | 1980 |
| gatccggctg | cccagagcg | ccctcccag | gccccaccc | tcccactcag tcctgccccc | 2040 |
| agccccgccc | tcccctctg | agttcccgcc | ccagcaccg | cctccctct ctgaatttcg | 2100 |
| cccccaggct | cccagactc | tacctgctcg | ctgagttcct | caagccccca ccctctctgg | 2160 |

```
cgggtcctcc ctcagaaaga tggggtaaag gtgtgcacac taggtacctg tcttcacgcc   2220
gtgattaatg ccactcacag agatggtggc gttggcaatg gggatgcctt gctcgtccgt   2280
caccaccccc ttaatgccgc ggtgcaccta gggaagcagg tgagggctgc tggtcctcag   2340
gaaggtccaa tgtggtccgc tgctccctcc cgcccatcca ggagcctgtg cagcctcctc   2400
tccccaggca ttgccctagc caccccacct gctccatgaa ggtgagcagc gcctccttgt   2460
tgttctccca ctcgcgggc agctcactct catgagggaa cttgtcacag cccaggtaga   2520
aggagagctc caggcagttg gtatgcaggt aactgaagtc attgatagct ggccggggac   2580
agatacagac ccaaagtcag cccctctccg gaccaggccc cgcccacagc ccctcccagg   2640
ctgactcact cccggtccgg gggttccact tggccccgtt gacgatgccc atgccgccgg   2700
tgtagtcctg ggcttggcag cctccgcggt agggctcggt caaggtgagg tgtgcggagg   2760
cgaaggagat ggcaagccac cggaagatgg cgtggtctgg agtctcctgg gcctcggaga   2820
cctcgtcctc atcctccccc cgggctgctg ccatggctgc ggccagcagc tgctcctggg   2880
taggcgtgcg ggccatatcg taggggtagg atactagccg ctcgccgccg ttcagatttg   2940
ctcccagcac gaaggggttc ttctccatcc aggcaatgat ggcccggacc tccgtggata   3000
cctggagtgg ccagcacgtg tgaggccagg gctgcagctc cggccactat ccccaaccta   3060
gcccgatcac cctccatgaa gcttcacacc agtactcgca cgatcccctg tcccccaacc   3120
cccagagcct cagcgtctgg agttcaggca ccgtcagccc cacccccaag cccagaacac   3180
caggacccca gggtccagct gctccctcct gcccttcag ccaggctgta gcctcaccgt   3240
ggcatctggc gaaaggtagc gttcagggat gggcaagtta ttgttgggga cccggtaggg   3300
gacccatttc ctctcctcag ctccccagag cacagagttg agatccggga aatcttcaaa   3360
gatgtcaaag ccctcctcag tccacagtcc cagcgcccag ttcccaaact ctgagccctg   3420
tggggagcca gcagggtagg catcggctac ccacacccccc acaaccccca gctgcctgga   3480
ccctggccag cctcacccttt caacccacca tctgcgctgc cacctcgtag ccatcagggt   3540
tcagtgaggg caccaggtgg atgcgtgtgt cctgcaccag gctgcgcaca cgtgggttcc   3600
catcgcggta ctctcggcac aggtactgca tgagcagcag caacagctct cggcccagca   3660
cctcgttgcc atggatccca gcagtgtagc ggaactcggg ctcccctgca agggcgggag   3720
cctcagtgag cactcagtct cccgaggccc agggcagctg aggaaggacc cagacccacc   3780
tcatacccga gggtctgggg gacagctggg gctcctaggg ccctgtaaga caagccagaa   3840
tccccagaga ggctccggaa caggcggag gcagtgagct ctgcacatca gcagcagagg   3900
ccagctgctg gcccccacag accctccccc agttcatgct cccagggtt gtctgagatc   3960
tccatggcat agatcttgag gcctcgtgag ctcttgccca ggctgtaagt gcgggtgatg   4020
gtggggcact cctcgttcac caccttcatg agctggcgca gaggggagg acgtggaatc   4080
aatcatgcaa tccgtccccc gctgaccatg ccccttccac ttccaggcc tgctctatgg   4140
cgagggacgg gcatgacccc ttcacgcagc cccaggtac tggcctcctt cctaaggtga   4200
gggacagcca gcatccctgg aaccagtagg gactgggccc agtgacagaa gcaccaggca   4260
cacactcccg tcagccacag acaggtccca ccccagccc caggatatat gctcccaacc   4320
tggcgcatgt ccttgtagct gtggtgccgg aaatccaggt catcggtggc caccacctca   4380
ttctgtgcgt agtagctgta gacagctgca agggaggcgg ggttgtcttt agctgggtgc   4440
cggctggccc accctagcac cccacctcca ctcagagccc ctgccagccc tccacactca   4500
cgggccacag agcacccccag cacctccagg cgcatgcaca ggctgccatt ccaggtgagt   4560
```

```
gggtagatgc ggatgaaacg agccaccacc ggctctggga gctcactcag cacgggtgtg    4620
tccttgtcca cgttcccatg aaaggtctgg ggagaggcag gcctcagagc agtactgcca    4680
gcccctctga gagcccaccc ctcgcccaga caatgggagc agagccaaga gcctgggcat    4740
ggtgcccacc atttcctcat agccgttggt gtacatcacc catgtctggc tgtcattgct    4800
gaagcccacg aagaaggtgg tcacaaaatc gtcactgtgg agtggacagt ggtcagagca    4860
agggtcttcc ccctcccagg ccctcaggtg gcctgagcct ccctcttccg agccccaaga    4920
atttaagagc tagcagggtg gtgctgcacg gcccaggtgt tgagcctggg tcctatgccc    4980
gtcacatagc catgggcagg tgatctgtcc ctaaactcat gtgctatcag gacacagggg    5040
ctgactgacc aggctgagga gtggggatgg gcagggtgag tccctcactg atcttttttgg   5100 ccttctttgg ctgggccaaa gaagggccca ctggaatctc cttaatggga cacagagcca    5160
tgcctatgta gccactcccc tctgccaact atccatgagc ctggccacgc actggatgct    5220
ggagtctctg ccctgggtga tgacgcctgt gaacgggta gtcctcctgg tgtccacctc     5280
tatccactgg gtcctggcat cgtcctcggc acaccacgca ccatcatagt agtcgtcctc    5340
agtggcaccg gtctgtccag ggggcagggg aggctgagca tgggcggagg agtcccttat    5400
cccagttggg agatgggccc atcccaatgc ccacctgcat gttgagccgg ccgcgctgtg    5460
cccccaggcc gtggcgcagc atggaggagg ctcggatctg gttgtcctca atacggtgtg    5520
actccatccc aatgggggga cactctgagg acgcgtaccc cagaatggtg gctcactagc    5580
tccatccttc cctccaccaa acccagaacc aaggagccca gagcccactc ccggcacatc    5640
gggggcacag tcagagggca gctctggtca gctggtggct ccctggtgcc ctgcaccagc    5700
ccacctggaa tcgactcaaa gccaggccag gagctgtttc caatcccagc ctgtgcttcc    5760
cctccctggg cctcagctgc cccatctgga gaacgggctg accatgccca gctctcaggg    5820
gacacacgtg aaatcacagg tagagctccc ccagggcgca gccacagatg tcatccagat    5880
ggggaccgtc tgcacaatgg ccctgcaggg atacctgtga aggtacctga ggtcctcact    5940
ccccaccaag gccccaggtc ctcccctac cacgcccagc cactaggggc cctggggagc     6000
tgccaccctc ctgaagcagg ccagcctggg gtccagggct ggggcagcca agcgaggcta    6060
tcctgggctc ccggggcccc tcccttctgg gtcccaagaa tctgagtagg aaagggttcc    6120
ggggacctgg gtcctgttttg tgacattggg ccagtcactt gtcccagcac cccatcctg    6180 tggcccccac cctcacccc ttgtgcccc cacttactga ctttctccgt aggcgtccac      6240
tcctcctcca actcctcgcc cttccggggc tctaggcgaca atgaagggag gacatggcac    6300
caagggcccg ggaggcaatc aggagtccag atgctgcccc acagggaccc aggcccaag     6360 ccccagccca acacctttgt ggtccttgcc cttctccact gcccacttgt cggtctcctc    6420
cttggggctg ctgtcctcct tttttgggttt ctctggaagg tgcaaggtag gaggggccag   6480
tcagcctggc tctgggcttt gaggaccatg tggggtggat caggcaggcc ccaggtggcc    6540
ttcagggcag gcctggtgtg ggaagtcctt ggtcccactc actcagctcc tccttctctt    6600
cgtccgtctg gcgctcagca tcgggcttct ggggcggagg aggcccaaag taatagtcca    6660
ctatggggag ggagagccag ctgaggctgc cctgaccctg ctgcggggcc tcagctcctg    6720
ggtccacagg agctcagcag acaggaccg cgccagaggg gaggaggacg ggagatgggg     6780
gacagctgag ttgggagagg gtcttgcagg agtcaggagc agcccgagct caggggcagc    6840
tgagcaagac cctgctgaag tcaccagccc ggccttccag gagcatctgg cctggggaaa    6900
ggactcgagg cccagggcat gggaaaggcc tggagggaca actggcacct gtgcctgggg    6960
```

```
ttgcgggctg gggggtgaga tggggagaca ttggaggcac tgatgggac  ctgggggcag    7020 ggaaatggcg atgcacgggc tgccacccag gaggaaaggg aacctgaggg ctccagggac    7080 gcagggcat  gagcaacagg gaggcaaaag ccctcgggct ccctgaagag agtggggcag    7140
tggccacgag ccagcgggaa gccagttaga gcacaggact gggagggctg aacccacat    7200 gggtgacagg gcagagtgtg tgcctaggga caccctgtg  ggggtcacag ccaagcagga    7260
accagggaag cggccaagga aagaccagcc tgagggcaga ggagacaggg cagtggctgg    7320
ggtgggcacg cagggacagc agggacagcg aggtaaccac gggcacaggt ggggttgcaa    7380
ggtgggtgag ttgccccagc tggctcctga ccacacccca gccccgaccc ccacctgcct    7440
atgtccctca gactctgggg tgctgggtac tcactgtcat cgtagttggg gatcacgtaa    7500
ccatcaccat agtcagggg  cagcggggc  agcagaggct tcacaggagg ctctggggag    7560
gcggggaggt taggaggggg ccagagcgcc gtggccatgg cacctcctct cctgccccc     7620 atcctaccaa tcctctcctc cggggctggg gccggggcct tctcctcagg ggctctggc     7680 cagacccgct cgggcctcct ccttctgctt ggggtggcc  tgggttgctt ctggcgccga    7740
atgtactcaa ctgaggggga ggctggctca gagtggggcc caaggctggg atgggcccat    7800
tggcacatcc cccaggccag gggtccgacc caggtgggc  tggcaggacc ctactcaaag    7860
tcctcatagt cctccctctc gatctggtca ttgtagtcca gtgtggttg  ctcggtctcc    7920 tcctccggct ctgaggggaa agcgctggta gctgcctgac aaccccaccc aggcctactc    7980
tggggaagcc ctcagtccaa ccagccaggg cagctggccc caaggccagg cggatgacgg    8040
ccactcacca ggctggtgct cctgtgcctc cacatgggtc tcctctcctg gattctgcca    8100
gttatttgag aggggcgccc ctgcaacaca ggagttccag aagcaggtgg gcggaggcc     8160 tgctctgacc accttgggag cctcaggcca ccagccaccc atagagccca cacagagcct    8220
gtggacaccc tcctgaggcc gagctcactc caaggaggcc tgagctcctc tggccttcag    8280
catcctgctg gcatctcatg gggccagaga gctgggccca ccttctgggg aacctactgt    8340
gctgctggag gccctaccac aaagctgtcc ccagcgggag aaggcaggag ggaactccat    8400
gggctcagag cccagggaca tctgggcagg ggctgagggg acagaggtcc cacccaaaag    8460
gctgccaagc cctctcccta cccaaaagag gctacagcac tgagggagcc caccaatcaa    8520
attgtgaaat ttatagcaaa agtgaggttc ccatccagtg gggagctgaa ggtctatagg    8580
aagcagggcc ccagaaacct gcctcccact ccctgcctcc acccgagcag gcagtcagag    8640
ccccatcacc ccagaggagc ccggcacaaa cctccctcct ggggtagctc ctcggggcca    8700
gggctggggg gtggggcag  tggccactcc agggtttctg agggagccag aatggggggc    8760
ctcttccctg acgggggctt cttggtgcc  ttggtggct  tctctttggg cttcttggtg    8820
gccttgggtg gctcctcctt gggcttcttg gtggcttag  gtggcttctc cttgggcttc    8880
ttggtggcct tgggtggctt ctccttcccc tccttgggcg gcctggggga cccctccaag    8940
gactccttgg gcaccttggg gcctttgtct ttcttgcctt tcttcccttt gtctttggtc    9000
ttttccggag gcactgtcca agatgcagac tcgtgtcaaa tgaacagagc cagctctgtg    9060
cccccatgag gcccctctct agatgcccag aacctgggca cagggactct tgtcagttcc    9120
cagtgcggat cagcaaactg agaggttaag tcatttgccc aagtggcaaa ctgggatccg    9180
gacccagatt ttctgtctgc aagtctgggg ctgtgaccac caatctcaac ctctctaaag    9240
actgagcgta gggttcccag ttcccagggg gaggccctca tcccccacc  tgccaaaacc    9300 tcaataggg  ttccttacta tccactcctc cactattctg ttctgggcac agaaggggca    9360
```

```
gagaggtgac tgagccatcc aggcctggag gagcatctgg tcatccctgc caactgccat    9420
acaaaggaag ggacatgggc ccaagacctt cccctggtct cctacggggc aagaaaagct    9480
tcaaagaaaa gggacacttg gttgagtatt gaagcccaaa gaagaggaag tggtctcctt    9540
tcgagaagta aggggtttgg aattgattgg aaggataggg agtcctgggg ggttcaggga    9600
tcacacagag gacagaaaag acaggtaggg agcttgtggc tgcacactca tttcagagtc    9660
tgggagaggg agcagggact ggttgtgagg attccccatg ggaatcctcc caggacccta    9720
agcaggagct gcaagtgctg ttgagaacct gatgagaggt ggggagcatg agggaagttt    9780
ggcagaaaca caggaaagct accaaatgca gacagccagg ggacgcaggg ctgctagagc    9840
ggtgccccag agccaggaga gcaagcctgg aaggagagcc agaggcagga ggggcacagg    9900
cagcccaggg tgtgggaagc agccaggaaa gatctagagc tggggtggca ggggagggge    9960 tgctgacatc aggaatgttg gatggtgcct tggaatctcc tgggagacag ggatcacaag   10020
accctctgcc accttccaga gggccacgat gaaaacagct aagatttact gacaactgat   10080
tatgcaagag gccgtgggtt aaatgcttca gtgatgcatc acctcatcta atttcctgta   10140
ctaatgtagg accacccatt gctcaccacc acctgaagcc ctgtgctcac caccacctga   10200
aactctctca cctacgtgag acctcctgga gtaggagggc aaaggcagga gggagggacg   10260
acgtgaagct gtgccaccaa cagggagagt ggtcccatta gtatggcagg gggtgacaca   10320
gcacagtccc ctgtggctca agcctagtac ctgtcgcgta ctggaggaat ggggataagc   10380
gacccgtaca accacagcac caaccctaga gccaccggcc cccaaaagcg ccctgccgc    10440 ccgggtgctg gatgtgcctc cacgccagcg ctgacctcgg cctagcacag ggtccctcca   10500
ggcatctggg ctcgcgtgcg cattagtaag ccagccattc ctcccctagc agactgggga   10560
gtggccagac cctaccgaat cccctgttc  ccacctgaga tgccagcccc ccacaccccc   10620
gccctgccct gggctcttac cttctgcggc cgtccctggc cgcttccctg gcttgccccc   10680
cgcctgggct tttcggaccc gcggggtggg ctcgggaggc ggcggggcct ccacgtcgtc   10740
ctcccggggc tcaggttcta gctctgacag gaagccctcg aggaactcct cgatctcgtc   10800
gtcggtcagc accgtctgcg ggcgcccccc agggcacagg gccagcaacg ccaggaggca   10860
gctgagcagg ggcgccccgc gcacggccgc catggccgcg gcacgcgcgg ggggctccgg   10920
ggagggcgcg ggggtcagg  ggctctgggt ctctgggaaa gggcggagag gggatcgaga   10980
cgggtgaggg aatccaggaa ggggcgggag agaggatggg gtgagcgagg gaatccggga   11040
aagggaggga gagtggatta gggtgggcga ggggaccccg gaaggggtgc tgggggggctc  11100 cgaagccaga ggggctcagg ggtggtcggg gcgctccgag gtctggcggc taataggcgc   11160
tccgcccccg cgtggcgcac tcccgcgcgg atagccgtct ccaaagcgct ggcggggccc   11220
ggggcggggg cgccggggct tccggagccg gctccccacc cccggggagg aggaggagga   11280
agagaaggag gagccgagag tggacggagg ggctgcgggg gggcggggg cggggggcgg    11340 ggggctaggg gcgggcagg cgggcggccg ctggcggcga gcgtcccaag cccggagact    11400
tgcgcctagg acagaggggc aggggcggg gcgactggga agacagaggg cctgaggaa     11460 ggaaaggtgg tggggagggc ctgggggtgcg ggtctgaggg ggccgacatc cctcctcctt   11520
ctgccctagg caccccccctt aaggcgggac cccgagtcca ccggggctct gagccctccg   11580
cgggtgacca ggaaccctgg acggaaagcc gtggtgtcag gcctctgaga cctctctcaa   11640 ttcgagggc  cacagaaagg ccaccccatc cttcccaggc tctggagcct ctgcccatgg   11700
gccctgctgc atcccagcgt caattcattc agtcatccta ccaacctctt caggtcggtg   11760
```

```
tggggccggg ccccgtgctg ggccccaggg agggacagca cagtgggaac tcactttcca   11820
gccaggaggc aggtgcaaaa ctgccctcag agtggccagc tgccccgctg ggggtaggag   11880
tcccatgtaa gggcatgcca tccctcccct ccgggtccca acgtggacaa atagccattt   11940
atcaccttct tcttaccaga actcattttt taaaaagtgt ctaccatacc tccagctgcc   12000
acatggaccc agagggccca gaggacccag aaggcaggtg gattgagtgt caactgatcc   12060
caggatccat cagggatgtg caccttggtg cctggtgttt gccataaggc ttctccaggg   12120
caaatgttgg ctgccctaca acggccatca acaggcagag tggtcccatt agtatggcag   12180
ggcgtgacac agcacagtcc cccgtgactc aagcctagtc cctgtctcat actggaggaa   12240
tggggagcta aggacagagc tccgaggaca ttcccctta aaggaatgag gacacaagag   12300
aaagctcaca ggtagtccat gggccaagtg cagaggcaga cagccctaag ccacgattgt   12360
ctgcggggtt tggccccagt gaagtagtca ggtagggaag cctaggagcc cctgggatga   12420
ttgacagggc agagtttgga cctggggtca aaggaaaga ggaaaagtgg gtcaggaagc   12480
acctgggtcc ccagagcagc cccgagtgag ttggagcagg cagcagccgg ggaggccaca   12540
gtggaggctg ctgggcctgg gatacatgcc accccctggg agcaggacca caaggaggcc   12600
ttgcctcctc tcacacctgg tcctgccaag accctgcctt tgctttctca ctgcatctcc   12660
ttgaaaaagc agtgggactg tgtcaggttc tggctctacc tcccaggcac cacatctcgg   12720
caggtagcct cagtgccgtc cacctgtgtc cctgttctcc ttgtcgttca tacaggatca   12780
tgcatgtgct gtgcctagca cacattcttg gcactcacac tgctgccttt tagctctcat   12840
catttgccct cagagatcaa cctgagctgt gcccactggg gcgctcagag cagaccctga   12900
gccccaacac ccaggctccc tgtgcacctg agcctgcctc tgcctgccac gtgccccag   12960 gccagtcctg gtggcagcaa ggatccgcaa gctctcccct ttcctcatcc tctgcaaagc   13020
tctgaatcat cttcttcaaa acttgttctg ggaatttgct ccgttgcccc agttgagcat   13080
gtcaagcccg gcggcccaag gctggggtga agcagcgtgg cacgtcactt ccctgggaac   13140
aactcacaca tggattggat ttgggtccaa catcctctgc cagggaaaat agaagccata   13200
agaaaacaaa aaaggaacag aaggaggctt ttcttcagtc acagcgagtc accaacaaaa   13260
acatgtgcaa aagctctcat ggagagctgg gccacaagga gggccatgat gttgggggcc   13320
ctctgacacc aagggtgtgg gcaggtggat gggaggcagc tgccctccat gccaggctga   13380
tgtgcctccc tttgggtggt ggggctggga ctcccactcc acttgaagac ctgcaccaaa   13440
aagtccttta gccctgtgcc caggctctgc cacggggccg tgagggggac ttctcccctc   13500
tgctgccaga gtgaagccag tcaggggat gggaggcttg tagccaagag cacctagtgg   13560
ctttcagggt cccttacccc tgccacttag cagggtctgc acctgcatcc aagtgttctc   13620
ctgggctaca gtgggggct ggtagacact ctggtgatcc actttcagct tcccacatgg   13680
atgtggcagg gactgctttg gcatttccct accccaaggg acagccactg cggcaggact   13740
gggctgggga gggtggggcc tgcgctgggg agggtgcccc ctgtcccttg ctgctgctgg   13800
aatgggaagg agagttgttg agagagccag aactgtccaa gggtggaagc tggcgaaact   13860
gacctgcagg gaacagggag acagggagca tggcccagtg agtaggtcct atgtagctct   13920
gaggccatca accctgccat gagggctgag accccaagag agaagttgag gttgggtcag   13980
gggcctgtta gtgccagctg aggaggggga caggccagcc tcctcccact gggacccaag   14040
ctatagctcc tgagcctcca gagctgcctg tgcctcaac ctggtcagag gtggaaactc   14100
acctgccagc aggcccagtg tgcctgagtt ctgactgtgg ggatctgcag ggcacagaag   14160
```

```
gataagaggt catcagggcc tggggacagg caggagtggc agggtctggg aggctgggag    14220
cagaccctcc caacctgccc catggcctcc gtggccccca ggaccccat ggcagcagct    14280 cagacacggg ttgtgcctca gaaggaagtg aagctgtgtg taccgagatg gcccagcaaa    14340 cccttgtat gtaaacttcc gccacagcc agctgtccag caccagcatg tgtatctggg    14400 ggaggggat aaatagaagg tctgggaggc ctgggatctg gccagcaggc tactgggatc    14460
acagatgcca gcccctccat atctccgctt gagtcctgga tctgcctcct gggaccaaag    14520
gggaaaggac caggctaggc tccttccttt ttgttcttcc ctcttggggg aggctcctag    14580
aaactccccc ttctctgccg cccaagtgcc tggatattac cagtgggtt agcctgtttg    14640 ggcccacaag atgggatggc tcccagagcc atgggacctg aggtctccca gacagtgtct    14700
agccaccctc acaactggca gaacaatttc cttggttttc aacaacttga aaaacatatg    14760
tgattttcca cagtccggtg cttctcaggc ctggctgctg agtgagcaga gttcatgctg    14820
aattccttcc actcaccaca gggcagacag caagcccagc tgtggggact cggttggggt    14880
gggggtcacc acagcaaggc gcggggagtg gggaggggg caggcttcca gcactgatga    14940
gtaattctgc tgcccgaaga tctgggaaga gggcatgtga caacttagtg caacaatctg    15000
cccagtgtta ggtcagaagg aaggagaggt cgttcaaaat ggagtctggt ggaaaaaata    15060
atgtttggcc ccacctcata cctccctcaa aattaactcc agattaatga ggtagatgtt    15120
agaagaggaa ccagggaagg actacaagaa aatatggagt ctttatttac attgtgaggt    15180
tttctttagg ttttgtttgt ttttgttttt gatatggagt ctcactctgt cacccaggct    15240
ggagtgcagt ggtgcgatcc cggctaactg caacctccgc ctcccaggtt caagagattc    15300
tcctgcctca gcctcccaag tatctgggga ttacaggcac atgccaccat gcccggcttt    15360
tttttttttt tttttttttt gtattttag tagagatggg gtttcaccat gttgaccagg    15420
cagatctcaa actcctgacc tcaagtgatc cacccgcctc agcctcccaa agtgctgggc    15480
gcccggcatg tgtgcccagc ctatattgac attcttgatg gagaagtctc ttaaggaagg    15540
acagagaagt ttggttgcat aaaagttttt accttctgta catcaaaata tactgaaaat    15600
gaaaataaag agcaaacaaa atactgagaa agaatgcagt gcttagagag cgaacattcc    15660
tggcctcctg tagttttagg aagcagctgt ggcctcagac ccatctgctg tgaacctcta    15720
ctccatattt attgcacttt ctgtctgtga gcgtcggttt ctctcctcta taacaatagg    15780
ataataatga cactaccatg ccttgcaaaa atgctacaag ggttcactga gataaatctg    15840
gagagtcatg cctgaaaaat agtaagtcgt tgataaaggg aagctgctat taataaataa    15900
agctttttct tttttttttt tttgagatgg aatctcactc tggcgcctag gctggagtgc    15960
agtgatgcaa tcttggctca ctgcaacctc cgcctcctgt gttcaagcaa tcctcctact    16020
tcagcatcct cagtagctgg gactacaggt gcgcaccacc atgcccggct agtttttac    16080 atttttaaag ctattaatag gccagccaca gtggctcatg cctataatcc cagcactttg    16140
ggaagctgag gcaggtggat c                                              16161
```

US 8,323,884 B2

ISOLATED SNARE YKT6 GENOMIC POLYNUCLEOTIDE FRAGMENTS FROM CHROMOSOME 7 AND THEIR USES

PRIORITY CLAIM

This application claims priority under 35 U.S.C. §19(e) to provisional application Ser. No. 60/234,422, filed Sep. 21, 2000 and is a divisional of application Ser. No. 10/642,946, filed Aug. 18, 2003, which is a continuation of application Ser. No. 09/957,956, filed Sep. 21, 2001, now abandoned, the contents of which all are incorporated herein by reference.

FIELD OF THE INVENTION

The invention is directed to isolated genomic polynucleotide fragments that encode human SNARE YKT6, human glucokinase, human adipocyte enhancer binding protein 1 (AEBP1) and DNA directed 50 kD regulatory subunit (POLD2), vectors and hosts containing these fragments and fragments hybridizing to noncoding regions as well as antisense oligonucleotides to these fragments. The invention is further directed to methods of using these fragments to obtain SNARE YKT6, human glucokinase, AEBP1 protein and POLD2 and to diagnose, treat, prevent and/or ameliorate a pathological disorder.

BACKGROUND OF THE INVENTION

Chromosome 7 contains genes encoding, for example, epidermal growth factor receptor, collagen-1-Alpha-1-chain, SNARE YKT6, human glucokinase, human adipocyte enhancer binding protein 1 and DNA polymerase delta small subunit (POLD2). SNARE YKT6, human glucokinase, human adipocyte enhancer binding protein 1 and DNA polymerase delta small subunit (POLD2) are discussed in further detail below.
SNARE YKT6

SNARE YKT6, a substrate for prenylation, is essential for vesicle-associated endoplasmic reticulum-Golgi transport (McNew, J. A. et al. J. Biol. Chem. 272, 17776-17783, 1997). It has been found that depletion of this function stops cell growth and manifests a transport block at the endoplasmic reticulum level.
Human Glucokinase Human glucokinase (ATP:D-hexose 6-phosphotransferase) is thought to play a major role in glucose sensing in pancreatic islet beta cells (Tanizawa et al., 1992, Mol. Endocrinol. 6:1070-1081) and in the liver. Glucokinase defects have been observed in patients with noninsulin-dependent diabetes mellitus (NIDDM) patients. Mutations in the human glucokinase gene are thought to play a role in the early onset of NIDDM. The gene has been shown by Southern Blotting to exist as a single copy on chromosome 7. It was further found to contain 10 exons including one exon expressed in islet beta cells and the other expressed in liver.
Human Adipocyte Enhancer Binding Protein 1

The adipocyte-enhancer binding protein 1 (AEBP1) is a transcriptional repressor having carboxypeptidase B-like activity which binds to a regulatory sequence (adipocyte enhancer 1, AE-1) located in the proximal promoter region of the adipose P2 (aP2) gene, which encodes the adipocyte fatty acid binding protein (Muise et al., 1999, Biochem. J. 343: 341-345). B-like carboxypeptidases remove C-terminal arginine and lysine residues and participate in the release of active peptides, such as insulin, alter receptor specificity for polypeptides and terminate polypeptide activity (Skidgel, 1988, Trends Pharmacol. Sci. 9:299-304). For example, they are thought to be involved in the onset of obesity (Naggert et al., 1995, Nat. Genet. 10:1335-1342). It has been reported that obese and hyperglycemic mice homozygous for the fat mutation contain a mutation in the CP-E gene.

Full length cDNA clones encoding AEBP1 have been isolated from human osteoblast and adipose tissue (Ohno et al., 1996, Biochem. Biophys Res. Commun. 228:411-414). Two forms have been found to exist due to alternative splicing. This gene appears to play a significant role in regulating adipogenesis. In addition to playing a role in obesity, adipogenesis may play a role in osteopenic disorders. It has been postulated that adipogenesis inhibitors may be used to treat osteopenic disorders (Nuttal et al., 2000, Bone 27:177-184).
DNA Polymerase Delta Small Subunit (POLD2)

DNA polymerase delta core is a heterodimeric enzyme with a catalytic subunit of 125 kD and a second subunit of 50 kD and is an essential enzyme for DNA replication and DNA repair (Zhang et al., 1995, Genomics 29:179-186). cDNAs encoding the small subunit have been cloned and sequenced. The gene for the small subunit has been localized to human chromosome 7 via PCR analysis of a panel of human-hamster hybrid cell lines. However, the genomic DNA has not been isolated and the exact location on chromosome 7 has not been determined.

OBJECTS OF THE INVENTION

Although cDNAs encoding the above-disclosed proteins have been isolated, their location on chromosome 7 has not been determined. Furthermore, genomic DNA encoding these polypeptides have not been isolated. Noncoding sequences can play a significant role in regulating the expression of polypeptides as well as the processing of RNA encoding these polypeptides.

There is clearly a need for obtaining genomic polynucleotide sequences encoding these polypeptides. Therefore, it is an object of the invention to isolate such genomic polynucleotide sequences.

SUMMARY OF THE INVENTION

The invention is directed to an isolated genomic polynucleotide, said polynucleotide obtainable from human chromosome 7 having a nucleotide sequence at least 95% identical to a sequence selected from the group consisting of:

(a) a polynucleotide encoding a polypeptide selected from the group consisting of human SNARE YKT6 depicted in SEQ ID NO:1, human glucokinase depicted in SEQ ID NO:2, human adipocyte enhancer binding protein 1 (AEBP1) depicted in SEQ ID NO:3 and DNA directed 50 kD regulatory subunit (POLD2) depicted in SEQ ID NO:4;

(b) a polynucleotide selected from the group consisting of SEQ ID NO:5 which encodes human SNARE YKT6 depicted in SEQ ID NO:1, SEQ ID NO:6 which encodes human glucokinase depicted in SEQ ID NO:2, SEQ ID NO:8 which encodes human adipocyte enhancer binding protein 1 depicted in SEQ ID NO:3 and SEQ ID NO:7 which encodes DNA directed 50 kD regulatory subunit (POLD2) depicted in SEQ ID NO:4;

(c) a polynucleotide which is a variant of SEQ ID NOS:5, 6, 7, or 8;

(d) a polynucleotide which is an allelic variant of SEQ ID NOS:5, 6, 7, or 8;

(e) a polynucleotide which encodes a variant of SEQ ID NOS:1, 2, 3, or 4;

(f) a polynucleotide which hybridizes to any one of the polynucleotides specified in (a)-(e);

(g) a polynucleotide that is a reverse complement to the polynucleotides specified in (a)-(f) and (h) containing at least 10 transcription factor binding sites selected from the group consisting of AP1FJ-Q2, AP1-C, AP1-Q2, AP1-Q4, AP4-Q5, AP4-Q6, ARNT-01, CEBP-01, CETS1P54-01, CREL-01, DELTAEF1-01, FREAC7-01, GATA1-02, GATA1-03, GATA1-04, GATA1-06, GATA2-02, GATA3-02, GATA-C, GC-01, GFII-01, HFH2-01, HFH3-01, HFH8-01, IK2-01, LMO2COM-01, LMO2COM-02, LYF1-01, MAX-01, NKX25-01, NMYC-01, S8-01, SOX5-01, SP1-Q6, SAEBP1-01, SRV-02, STAT-01, TATA-01, TCF11-01, USF-01, USF-C and USF-Q6
as well as nucleic acid constructs, expression vectors and host cells containing these polynucleotide sequences.

The polynucleotides of the present invention may be used for the manufacture of a gene therapy for the prevention, treatment or amelioration of a medical condition by adding an amount of a composition comprising said polynucleotide effective to prevent, treat or ameliorate said medical condition.

The invention is further directed to obtaining these polypeptides by (a) culturing host cells comprising these sequences under conditions that provide for the expression of said polypeptide and (b) recovering said expressed polypeptide.

The polypeptides obtained may be used to produce antibodies by (a) optionally conjugating said polypeptide to a carrier protein;

(b) immunizing a host animal with said polypeptide or peptide-carrier protein conjugate of step (b) with an adjuvant and (c) obtaining antibody from said immunized host animal.

The invention is further directed to polynucleotides that hybridize to noncoding regions of said polynucleotide sequences as well as antisense oligonucleotides to these polynucleotides as well as antisense mimetics. The antisense oligonucleotides or mimetics may be used for the manufacture of a medicament for prevention, treatment or amelioration of a medical condition.

The invention is further directed to kits comprising these polynucleotides and kits comprising these antisense oligonucleotides or mimetics.

In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to diagnose a pathological condition in a subject comprising (a) determining the presence or absence of a mutation in the polynucleotides of the present invention and (b) diagnosing a pathological condition or a susceptibility to a pathological condition based on the presence or absence of said mutation.

DETAILED DESCRIPTION OF THE INVENTION

The invention is directed to isolated genomic polynucleotide fragments that encode human SNARE YKT6, human glucokinase, human adipocyte enhancer binding protein 1 and DNA directed 50 kD regulatory subunit (POLD2), which in a specific embodiment are the SNARE YKT6, human glucokinase, human adipocyte enhancer binding protein 1 and DNA directed 50 kD regulatory subunit (POLD2) genes, as well as vectors and hosts containing these fragments and polynucleotide fragments hybridizing to noncoding regions, as well as antisense oligonucleotides to these fragments.

As defined herein, a "gene" is the segment of DNA involved in producing a polypeptide chain; it includes regions preceding and following the coding region, as well as intervening sequences (introns) between individual coding segments (exons).

As defined herein "isolated" refers to material removed from its original environment and is thus altered "by the hand of man" from its natural state. An isolated polynucleotide can be part of a vector, a composition of matter or could be contained within a cell as long as the cell is not the original environment of the polynucleotide.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand.

The human SNARE YKT6 polypeptide has the amino acid sequence depicted in SEQ ID NO:1 and is encoded by the genomic DNA sequence shown in SEQ ID NO:5. The genomic DNA for SNARE YKT6 gene is 39,000 base pairs in length and contains seven exons (see Table 4 below for location of exons). As will be discussed in further detail below, the SNARE YKT6 gene is situated in genomic clone AC006454 at nucleotides 36,001-75,000.

The human glucokinase is depicted in SEQ ID NO:2 and is encoded by the genomic DNA sequence shown in SEQ ID NO:6. The human glucokinase genomic DNA is 46,000 base pairs in length and contains ten exons (see Table 3 below for location of exons).

The human adipocyte enhancer binding protein 1 has the amino acid sequence depicted in SEQ ID NO:3 and is encoded by the genomic DNA sequence shown in SEQ ID NO:8. The adipocyte enhancer binding protein 1 is 16,000 base pairs in length and contains 21 exons (see Table 2 below for location of exons). As will be discussed in further detail below, the human AEBP1 gene is situated in genomic clone AC006454 at nucleotides 137,041-end.

POLD2 has an amino acid sequence depicted in SEQ ID NO:4 and a genomic DNA sequence depicted in SEQ ID NO:7. The POLD2 gene is 19,000 base pairs in length and contains ten exons (see Table 1 below for location of exons). As will be discussed in further detail below, the POLD2 gene is situated in genomic clone AC006454 at nucleotides 119,001-138,000.

The polynucleotides of the invention have at least a 95% identity and may have a 96%, 97%, 98% or 99% identity to the polynucleotides depicted in SEQ ID NOS:5, 6, 7 or 8 as well as the polynucleotides in reverse sense orientation, or the polynucleotide sequences encoding the SNARE YKT6, human glucokinase, AEBP1, or POLD2 polypeptides depicted in SEQ ID NOS:1, 2, 3, or 4 respectively.

A polynucleotide having 95% "identity" to a reference nucleotide sequence of the present invention, is identical to the reference sequence except that the polynucleotide sequence may include on average up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identify, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 95 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 5% of the sequence (number of bases at the 5' and 3' ends not matched/total numbers of bases in the query sequence) so 5% is subtracted from the percent identity score calculated by the FASTDB program. If the remaining 95 bases were perfectly matched the final percent identity would be 95%. In another example, a 95 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for purposes of the present invention.

A polypeptide that has an amino acid sequence at least, for example, 95% "identical" to a query amino acid sequence is identical to the query sequence except that the subject polypeptide sequence may include on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutlag et al. (Com. App. Biosci. (1990) 6:237-245). In a sequence alignment, the query and subject sequence are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

The invention also encompasses polynucleotides that hybridize to the polynucleotides depicted in SEQ ID NOS: 5, 6, 7 or 8. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5× SSC, 0.1% SDS, 0.25% milk, and no formamide; or 40% formamide, 5× SSC, 0.5% SDS). Moderate stringency hybridization conditions correspond to a higher temperature of 55° C., e.g., 40% formamide, with 5× or 6× SCC. High stringency hybridization conditions correspond to the highest temperature of 65° C., e.g., 50% formamide, 5× or 6× SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the variant polypeptides may differ from the amino acid sequences depicted in SEQ ID NOS:1, 2, 3 or 4 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the SNARE YKT6, AEBP1, human glucokinase and POLD2 genes. These include but are not limited to an intron, a 5' non-coding region, a 3' non-coding region and splice junctions (see Tables 1-4), as well as transcription factor binding sites (see Table 5). The polynucleotide fragments may be a short polynucleotide fragment which is between about 8 nucleotides to about 40 nucleotides in length. Such shorter fragments may be useful for diagnostic purposes. Such short polynucleotide fragments are also preferred with respect to polynucleotides containing or hybridizing to polynucleotides containing splice junctions. Alternatively larger fragments, e.g., of about 50, 150, 500, 600 or about 2000 nucleotides in length may be used.

TABLE 1

Exon/Intron Regions of Polymerase, DNA directed, 50 kD regulatory subunit (POLD2) Genomic DNA

| EXONS | LOCATION (nucleotide no.) (Amino acid no.) |
|---|---|
| 1. | 11546 . . . 11764 |
|    | 1            73 |
| 2. | 15534 . . . 15656 |
|    | 74           114 |
| 3. | 15857 . . . 15979 |
|    | 115          155 |
| 4. | 16351 . . . 16464 |
|    | 156          193 |
| 5. | 16582 . . . 16782 |
|    | 194          260 |
| 6. | 17089 . . . 17169 |
|    | 261          287 |
| 7. | 17327 . . . 17484 |
|    | 288          339 |
| 8. | 17704 . . . 17829 |
|    | 340          381 |
| 9. | 18199 . . . 18303 |
|    | 382          416 |
| 10. | 18653 . . . 18811 |
|     | 417          469 |

'tga' at 18812-14
Poly A at 18885-90

TABLE 2

AEBP1 (adipocyte enhancer binding protein 1), vascular smooth muscle-type. Reverse strand coding.

| EXONS | LOCATION (nucleotide no.) (Amino acid no.) |
|---|---|
| 21. | 1301 . . . 1966 |
|     | 1158          937 |
| 20. | 2209 . . . 2304 |
|     | 936           905 |
| 19. | 2426 . . . 2569 |
|     | 904           857 |

TABLE 2-continued

AEBP1 (adipocyte enhancer binding protein 1), vascular smooth muscle-type. Reverse strand coding.

| EXONS | LOCATION (nucleotide no.) (Amino acid no.) | |
|---|---|---|
| 18. | 2651 ... 3001 | |
| | 856 | 740 |
| 17. | 3238 ... 3417 | |
| | 739 | 680 |
| 16. | 3509 ... 3706 | |
| | 679 | 614 |
| 15. | 3930 ... 4052 | |
| | 613 | 573 |
| 14. | 4320 ... 4406 | |
| | 572 | 544 |
| 13. | 4503 ... 4646 | |
| | 543 | 496 |
| 12. | 4750 ... 4833 | |
| | 495 | 468 |
| 11. | 5212 ... 5352 | |
| | 467 | 421 |
| 10. | 5435 ... 5545 | |
| | 420 | 384 |
| 9. | 6219 ... 6272 | |
| | 383 | 366 |
| 8. | 6376 ... 6453 | |
| | 365 | 340 |
| 7. | 6584 ... 6661 | |
| | 339 | 314 |
| 6. | 7476 ... 7553 | |
| | 313 | 288 |
| 5. | 7629 ... 7753 | |
| | 287 | 247 |
| 4. | 7860 ... 7931 | |
| | 246 | 223 |
| 3. | 8050 ... 8121 | |
| | 222 | 199 |
| 2. | 8673 ... 9014 | |
| | 198 | 85 |
| 1. | 10642 ... 10893 | |
| | 84 | 1 |

Stop codon 1298-1300
Poly A-site 1013-18

TABLE 3

Glucokinase

| EXONS | LOCATION (nucleotide no.) (Amino acid no.) | |
|---|---|---|
| 1. | 20485 ... 20523 | |
| | 1 | 13 |
| 2. | 25133 ... 25297 | |
| | 14 | 68 |

TABLE 3-continued

Glucokinase

| EXONS | LOCATION (nucleotide no.) (Amino acid no.) | |
|---|---|---|
| 3. | 26173 ... 26328 | |
| | 69 | 120 |
| 4. | 27524 ... 27643 | |
| | 121 | 160 |
| 5. | 28535 ... 28630 | |
| | 161 | 192 |
| 6. | 28740 ... 28838 | |
| | 193 | 225 |
| 7. | 30765 ... 30950 | |
| | 226 | 287 |
| 8. | 31982 ... 32134 | |
| | 288 | 338 |
| 9. | 32867 ... 33097 | |
| | 339 | 415 |
| 10. | 33314 ... 33460 | |
| | 416 | 464 |

Stop codon 33461-3

TABLE 4

SNARE YKT6. Reverse strand coding.

| EXONS | LOCATION (nucleotide no.) (Amino acid no.) | |
|---|---|---|
| 7. | 4320 ... 4352 | |
| | 198 | 188 |
| 6. | 5475 ... 5576 | |
| | 187 | 154 |
| 5. | 8401 ... 8466 | |
| | 153 | 132 |
| 4. | 9107 ... 9211 | |
| | 131 | 97 |
| 3. | 10114 ... 10215 | |
| | 96 | 63 |
| 2. | 11950 ... 12033 | |
| | 62 | 35 |
| 1. | 15362 ... 15463 | |
| | 34 | 1 |

Stop codon at 4817-19
Poly A-site: 4245-4250

TABLE 5

TRANSCRIPTION FACTOR BINDING SITES

| BINDING SITES | SNARE YKT6 | GLUCOKINASE | POLD2 | AEBP1 |
|---|---|---|---|---|
| AP1FJ-Q2 | 11 | | | 11 |
| AP1-C | 15 | 15 | 7 | 6 |
| AP1-Q2 | 9 | | | 5 |
| AP1-Q4 | 7 | | | 4 |
| AP4-Q5 | 36 | | 5 | 43 |
| AP4-Q6 | 17 | | | 23 |
| ARNT-01 | 7 | | | 5 |
| CEBP-01 | 7 | | | |

TABLE 5-continued

TRANSCRIPTION FACTOR BINDING SITES

| BINDING SITES | SNARE YKT6 | GLUCOKINASE | POLD2 | AEBP1 |
|---|---|---|---|---|
| CETS1P54-01 | 6 | | | |
| CREL-01 | 7 | | | |
| DELTAEF1-01 | 64 | 12 | 5 | 50 |
| FREAC7-01 | | 4 | | |
| GATA1-02 | 19 | | | |
| GATA1-03 | 12 | | | 6 |
| GATA1-04 | 25 | 6 | | |
| GATA1-06 | 8 | 5 | | |
| GATA2-02 | 10 | | | |
| GATA3-02 | 5 | | | |
| GATA-C | 11 | 6 | | |
| GC-01 | | | | 4 |
| GFII-01 | 6 | | | |
| HFH2-01 | 5 | | | |
| HFH3-01 | 10 | | | |
| HFH8-01 | 4 | | | |
| IK2-01 | 49 | | | 29 |
| LMO2COM-01 | 41 | 6 | | 27 |
| LMO2COM-02 | 31 | 5 | | 7 |
| LYF1-01 | 10 | 13 | 6 | |
| MAX-01 | 4 | | | |
| MYOD-01 | 7 | | | |
| MYOD-Q6 | 32 | 19 | 7 | 12 |
| MZF1-01 | 99 | 40 | 15 | 94 |
| NF1-Q6 | 5 | | | 7 |
| NFAT-Q6 | 43 | 8 | 7 | 8 |
| NFKAPPAB50-01 | | 4 | | |
| NKX25-01 | 13 | 14 | 5 | |
| NMYC-01 | 12 | | | 8 |
| S8-01 | | 30 | 4 | |
| SOX5-01 | 21 | 20 | 4 | 4 |
| SP1-Q6 | | | | 8 |
| SAEBP1-01 | | 4 | | |
| SRV-02 | 5 | | | |
| STAT-01 | 6 | | | |
| TATA-01 | 8 | | | |
| TCF11-01 | 47 | 28 | 5 | 19 |
| USF-01 | 12 | 8 | 6 | 8 |
| USF-C | 16 | 12 | 12 | 8 |
| USF-Q6 | 6 | | | |

In a specific embodiment, such noncoding sequences are expression control sequences. These include but are not limited to DNA regulatory sequences, such as promoters, enhancers, repressors, terminators, and the like, that provide for the regulation of expression of a coding sequence in a host cell. In eukaryotic cells, polyadenylation signals are also control sequences.

In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. A transcriptional control sequence is "operatively linked" to a polynucleotide encoding a heterologous polypeptide sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the DNA sequence under the control of the expression control sequence and production of the desired product encoded by the polynucleotide sequence. If a gene that one desires to insert into a recombinant DNA molecule does not contain an appropriate start signal, such a start signal can be inserted upstream (5') of and in reading frame with the gene.

Expression of Polypeptides
Isolated Polynucleotide Sequences

The human chromosome 7 genomic clone of accession number AC006454 has been discovered to contain the SNARE YKT6 gene, the human glucokinase gene, the AEBP1 gene, and the POLD2 gene by Genscan analysis (Burge et al., 1997, J. Mol. Biol. 268:78-94), BLAST2 and TBLASTN analysis (Altschul et al., 1997, Nucl. Acids Res. 25:3389-3402), in which the sequence of AC006454 was compared to the SNARE YKT6 cDNA sequence, accession number NM_006555 (McNew et al., 1997, J. Biol. Chem. 272:17776-177783), the human glucokinase cDNA sequence (Tanizawa et al., 1992, Mol. Endocrinol. 6:1070-1081), accession number NM_000162 (major form) and M69051 (minor form), AEBP1 cDNA sequence, accession number NM_001129 (accession number D86479 for the osteoblast type) (Layne et al., 1998, J. Biol. Chem. 273:15654-15660) and the POLD2 cDNA sequence, accession number NM_006230 (Zhang et al., 1995, Genomics 29:179-186).

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) or long chain PCR may be used. In a specific embodiment, 5' or 3' non-coding portions of each gene may be identified by methods including but are not limited to, filter probing, clone enrichment using specific probes and protocols similar or identical to 5' and 3' "RACE" protocols which are well known in the art. For instance, a method similar to 5' RACE is available for generating the missing 5' end of a desired full-length transcript. (Fromont-Racine et al., 1993, Nucl. Acids Res. 21:1683-1684).

Once the DNA fragments are generated, identification of the specific DNA fragment containing the desired SNARE YKT6 gene, the human glucokinase gene, the AEBP1 gene, or POLD2 gene may be accomplished in a number of ways. For example, if an amount of a portion of a SNARE YKT6 gene, the human glucokinasegene, the POLD2 gene or AEBP1 gene, or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in SEQ ID NOS:5, 6, 7 or 8. Preferably, a fragment is selected that is highly unique to the encoded polypeptides. Those DNA fragments with substantial homology to the probe will hybridize. As noted above, the greater the degree of homology, the more stringent hybridization conditions can be used. In one embodiment, low stringency hybridization conditions are used to identify a homologous SNARE YKT6, the human glucokinase, the AEBP1, or POLD2 polynucleotide. However, in a preferred aspect, and as demonstrated experimentally herein, a nucleic acid encoding a polypeptide of the invention will hybridize to a nucleic acid derived from the polynucleotide sequence depicted in SEQ ID NOS:5, 6, 7 or 8 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the SNARE YKT6, the human glucokinase, the AEBP1, or POLD2 polynucleotide.

A gene encoding SNARE YKT6, the human glucokinase, the AEBP1, or POLD2 polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the SNARE YKT6 gene (nucleotides 4320-15463 of SEQ ID NO:5), human glucokinase gene (nucleotides 20485-33460 of SEQ ID NO:6), AEBP1 gene (nucleotides 1301-13893 of SEQ ID NO:8) or POLD2 gene (nucleotides 11546-18811 of SEQ ID NO:7) operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The invention is further directed to a nucleic acid construct comprising expression control sequences derived from SEQ ID NOS: 5, 6, 7 or 8 and a heterologous polynucleotide sequence.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences which regulate the expression of the polynucleotide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the prokaryotic beta-lactamase gene (Villa-Komaroff et al., 1978, *Proc. Natl. Acad. Sci. USA* 75: 3727-3731), as well as the tac promoter (DeBoer et al., 1983, *Proc. Natl. Acad. of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8: 423-488.

Eukaryotic promoters may be obtained from the genomes of viruses such as polyoma virus, fowlpox virus, adenovirus, bovine papilloma virus, avian sarcoma virus, cytomegalovirus, a retrovirus, hepatitis-B virus and SV40. Alternatively, heterologous mammalian promoters, such as the actin promoter or immunoglobulin promoter may be used.

The constructs of the invention may also include enhancers. Enhancers are cis-acting elements of DNA, usually from about 10 to about 300 bp that act on a promoter to increase its transcription. Enhancers from globin, elastase, albumin, alpha-fetoprotein, and insulin enhancers may be used. However, an enhancer from a virus may be used; examples include SV40 on the late side of the replication origin, the cytomegalovirus early promoter enhancer, the polyoma enhancer on the late side of the replication origin and adenovirus enhancers.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region, which codes for an amino acid sequence linked to the amino terminus of the polypeptide which can direct the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the polynucleotide of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. An example of suitable selectable markers for mammalian cells are those that enable the identification of cells competent to take of the nucleic acids of the present invention, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980).

The vectors of the present invention preferably contain an element(s) that permits stable integration of the vector into the host cell genome or autonomous replication of the vector in the cell independent of the genome of the cell.

For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional polynucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAM§1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a polynucleotide sequence of the present invention may be inserted into the host cell to increase production of the gene product. An increase in the copy number of the polynucleotide sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, or a *Streptomyces* cell, e.g., *Streptomyces lividans* or *Streptomyces murinus*, or gram negative bacteria such as *E. coli* and *Pseudomonas* sp.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian cell (e.g., human cell), an insect cell, a plant cell or a fungal cell. Mammalian host cells that could be used include but are not limited to human Hela, embryonic kidney cells (293), lung cells, H9 and Jurkat cells, mouse NIH3T3 and C127 cells, Cos 1, Cos 7 and CV1, quail QC1-3 cells, mouse L cells and Chinese Hamster ovary (CHO) cells. These cells may be transfected with a vector containing a transcriptional regulatory sequence, a protein coding sequence and transcriptional termination sequences. Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). The fungal host cell may also be a yeast cell. OYeastO as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980). The fungal host cell may also be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182-187, Academic Press, Inc., New York; Ito et al., 1983, *Journal of Bacteriology* 153: 163; and Hinnen et al., 1978, *Proc. e Natl Acad. f Sci.s USA* 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. In a specific embodiment, an enzyme assay may be used to determine the activity of the polypeptide. For example, AEBP1 activity can be determined by measuring carboxypeptidase activity as described by Muise and Ro, 1999, Biochem. J. 343:341-345. Here, the conversion of hippuryl-L-arginine, hippuryl-L-lysine or hippuryl-L-phenylalanine to hippuric acid may be monitored spectrophotometrically. POLD2 activity may be detected by assaying for DNA polymerase_ activity (see, for example, Ng et al., 1991, J. Biol. Chem. 266:11699-11704).

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing, differential solubility (e.g., ammonium sulfate precipitation), SDS-PAGE, or extraction (see, e.g., *Protein Purification*, J.-C. Janson and Lars Ryden, editors, VCH Publishers, New York, 1989).

Antibodies

According to the invention, the SNARE YKT6, human glucokinase, AEBP1 or POLD2 polypeptides produced according to the method of the present invention may be used as an immunogen to generate any of these polypeptides. Such antibodies include but are not limited to polyclonal, monoclonal, chimeric, single chain, Fab fragments, and an Fab expression library.

Various procedures known in the art may be used for the production of antibodies. For the production of antibody, various host animals can be immunized by injection with the polypeptide thereof, including but not limited to rabbits, mice, rats, sheep, goats, etc. In one embodiment, the polypeptide or fragment thereof can optionally be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the SNARE YKT6, human glucokinase, AEBP1 or POLD2 polypeptide, any technique that provides for the production of antibody molecules by continuous cell lines in culture may be used. These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for the SNARE YKT6, human glucokinase, AEBP1 or POLD2 polypeptide together with genes from a human antibody molecule of appropriate biological activity can be used; such antibodies are within the scope of this invention.

According to the invention, techniques described for the production of single chain antibodies (U.S. Pat. No. 4,946,778) can be adapted to produce polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for the SNARE YKT6, AEBP1, human glucokinase or POLD2 polypeptides.

Antibody fragments which contain the idiotype of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2, fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a particular polypeptide, one may assay generated hybridomas for a product which binds to a particular polypeptide fragment containing such epitope. For selection of an antibody specific to a particular polypeptide from a particular species of animal, one can select on the basis of positive binding with the polypeptide expressed by or isolated from cells of that species of animal.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Uses of Polynucleotides
Diagnostics

Polynucleotides containing noncoding regions of SEQ ID NOS:5, 6, 7 or 8 may be used as probes for detecting mutations from samples from a patient. Genomic DNA may be isolated from the patient. A mutation(s) may be detected by Southern blot analysis, specifically by hybridizing restriction digested genomic DNA to various probes and subjecting to agarose electrophoresis.

Polynucleotides containing noncoding regions may be used as PCR primers and may be used to amplify the genomic DNA isolated from the patients. Additionally, primers may be obtained by routine or long range PCR, that can yield products containing more than one exon and intervening intron. The sequence of the amplified genomic DNA from the patient may be determined using methods known in the art. Such probes may be between 10-100 nucleotides in length and may preferably be between 20-50 nucleotides in length.

Thus the invention is thus directed to kits comprising these polynucleotide probes. In a specific embodiment, these probes are labeled with a detectable substance.

Antisense Oligonucleotides and Mimetics

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

The antisense oligonucleotides or mimetics of the present invention may be used to decrease levels of a polypeptide. For example, SNARE YKT6 has been found to be essential for vesicle-associated endoplasmic reticulum-Golgi transport and cell growth. Therefore, the SNARE YKT6 antisense oligonucleotides of the present invention could be used to inhibit cell growth and in particular, to treat or prevent tumor growth. POLD2 is necessary for DNA replication. POLD2 antisense sequences could also be used to inhibit cell growth. Glucokinase and AEBP1 antisense sequences may be used to treat hyperglycemia.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50 as found to be effective in in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, SNARE YKT6 is necessary for cell growth, POLD2 is involved in DNA replication and repair, AEBP1 is involved in repressing adipogenesis and glucokinase is involved in glucose sensing in pancreatic islet beta cells and liver. Therefore, the SNARE YKT6 gene may be used to modulate or prevent cell apoptosis and treat such disorders as virus-induced lymphocyte depletion (AIDS); cell death in neurodegenerative disorders characterized by the gradual loss of specific sets of neurons (e.g., Alzheimer's Disease, Parkinson's disease, ALS, retinitis pigmentosa, spinal muscular atrophy and various forms of cerebellar degeneration), cell death in blood cell disorders resulting from deprivation of growth factors (anemia associated with chronic disease, aplastic anemia, chronic neutropenia and myelodysplastic syndromes) and disorders arising out of an acute loss of blood flow (e.g., myocardial infarctions and stroke). The glucokinase gene may be used to treat diabetes mellitus. The AEBP1 gene may be used to modulate or inhibit adipogenesis and treat obesity, diabetes mellitus and/or osteopenic disorders. POLD2 may be used to treat defects in DNA repair such as xeroderma pigmentosum, progeria and ataxia telangiectasia.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," *Science*, 247, 1465-1468, 1990; and Wolff, Jon A, "Human dystrophin expression in mdx mice after intramuscular injection of DNA constructs," *Nature*, 352, 815-818, 1991. As used herein, vectors are agents that transport the gene into the cell without degradation and include a promoter yielding expression of the gene in the cells into which it is delivered. As will be discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes:

a) Biological agents derived from viral, bacterial or other sources.

b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous poly A addition signals.

Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN[108]™ and LIPOFECTACE™, which are formed of cationic lipids such as N-[1-(2,3 dioleyloxy)-propyl]-n,n, n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, Nature 337:387 (1989)). Intravenous injection of cationic lipid-plasmid complexes into mice has been shown to result in expression of the DNA in lung (Brigham et al., Am. J. Med. Sci. 298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J-P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is N4-spermine cholesteryl carbamate (GL-67) disclosed in U.S. Pat. No. 5,767,099. Additional preferred lipids include N4-spermidine cholestryl carbamate (GL-53) and 1-(N-4-spermind)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class I molecule complexed to §2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

What is claimed is:

1. An isolated acid molecule, said nucleic acid molecule selected from the group consisting of:

(a) a nucleic acid molecule 39,000 nucleotides in length which is at least 99% identical to SEQ ID NO:5 which encodes a polypeptide that has human SNARE YKT6 activity, wherein SEQ ID NO: 5 consists of a 5'-noncoding region shown in sequence segment 39000-15464 of SEQ ID NO:5, a 3'-non coding region shown in sequence segment 4319-1 of SEQ ID NO:6, exons regions shown in sequence segments 15463-15362, 12033-11950, 10215-10114, 9211-9107, 8466-8401, 5576-5475, 4352-4320 of SEQ ID NO:5 and intron regions shown in sequence segments 15361-12034, 11949-10216, 10113-9212, 9106-8467, 8400-5577, 5474-4353, of SEQ ID NO:5;

(b) a fragment of (a), comprising at least nucleotides 15463-4320 of SEQ ID NO:5 which encodes a polypeptide having human SNARE YKT6 activity and;

(c) a nucleic acid molecule which is a complement of the nucleic acid molecules specified in (a)-(b).

2. A nucleic acid construct comprising the nucleic acid molecule of claim 1.

3. An expression vector comprising the nucleic acid molecule of claim 1.

4. A recombinant host cell comprising the nucleic acid molecule of claim 1.

5. A method for obtaining a polypeptide having human SNARE YKT6 activity comprising:
   (a) culturing the recombinant host cell of claim 4 under conditions that provide for the expression of said polypeptide and
   (b) recovering said expressed polypeptide.

6. A composition comprising the nucleic acid molecule of claim 1 and a carrier.

7. A kit comprising the nucleic acid molecule of claim 1.

8. The kit according to claim 7, in which the nucleic acid molecule is labeled with a detectable substance.

9. A method of detecting the presence of a nucleic acid sequence of SEQ ID NO:5, its complementary sequence or unique fragment thereof in a sample, said method comprising contacting the sample with the nucleic acid molecule of claim 1 and determining whether the nucleic acid molecule binds to said nucleic acid sequence in the sample.

10. An isolated nucleic acid molecule consisting of a 5'-noncoding region shown in sequence segment 39000-15464 of SEQ ID NO:5, or a full complement of said isolated nucleic acid molecule.

11. An isolated nucleic acid molecule consisting of at least 2000 contiguous nucleotides in sequence segments of a 5'-noncoding region shown in sequence segment 39000-15464 of SEQ ID NO:5 or a full complement of said isolated nucleic acid molecule.

12. The isolated nucleic acid molecule of claim 1, wherein said isolated nucleic acid molecule is an RNA or DNA molecule.

13. The isolated nucleic acid molecule of claim 10, wherein said isolated nucleic acid molecule is an RNA or DNA molecule.

14. The isolated nucleic acid molecule of claim 11, wherein said isolated nucleic acid molecule is an RNA or DNA molecule.

15. A kit comprising the nucleic acid molecule of claim 10.

16. A kit comprising the nucleic acid molecule of claim 11.

\* \* \* \* \*